United States Patent
Lapido et al.

(10) Patent No.: US 11,773,083 B2
(45) Date of Patent: Oct. 3, 2023

(54) SOLID STATE FORMS OF BELUMOSUDIL AND BELUMOSUDIL SALTS

(71) Applicant: TEVA PHARMACEUTICALS INTERNATIONAL GMBH, Jona (CH)

(72) Inventors: Polina Lapido, Rishon Lezion (IL); Inbal Shumacher, Kadima (IL); Ofir Shaul, Hod Hasharon (IL)

(73) Assignee: TEVA PHARMACEUTICALS INTERNATIONAL GMBH, Jona (CH)

( * ) Notice: Subject to any disclaimer, the term of this patent is extended or adjusted under 35 U.S.C. 154(b) by 0 days.

(21) Appl. No.: 18/075,513

(22) Filed: Dec. 6, 2022

(65) Prior Publication Data

US 2023/0117059 A1   Apr. 20, 2023

Related U.S. Application Data

(63) Continuation of application No. PCT/US2021/070924, filed on Jul. 22, 2021.

(60) Provisional application No. 63/137,212, filed on Jan. 14, 2021, provisional application No. 63/104,329, filed on Oct. 22, 2020, provisional application No. 63/075,368, filed on Sep. 8, 2020, provisional application No. 63/054,918, filed on Jul. 22, 2020.

(51) Int. Cl.
*C07D 403/12* (2006.01)

(52) U.S. Cl.
CPC ........ *C07D 403/12* (2013.01); *C07B 2200/13* (2013.01)

(58) Field of Classification Search
CPC ..................................................... C07D 403/12
See application file for complete search history.

(56) References Cited

FOREIGN PATENT DOCUMENTS

| CN | 106916145 A | 7/2017 |
|---|---|---|
| EP | 3875078 A1 | 9/2021 |
| WO | 2006105081 A2 | 10/2006 |
| WO | 2008054599 A2 | 5/2008 |
| WO | 2012040499 A2 | 3/2012 |
| WO | 2014055996 A2 | 4/2014 |
| WO | 2015157556 A1 | 10/2015 |
| WO | 2021129589 A1 | 7/2021 |
| WO | 2022170864 A1 | 8/2022 |

OTHER PUBLICATIONS

Public summary of opinion on orphan designation 2-(3-(4-(1H-Indazol-5-ylamino)quinazolin-2-yl)phenoxy)-Nisopropylacetamide-methane sulfonic acid salt for the treatment of graftversus-host disease, Jan. 9, 2020 (5 pages).

Mino R. Caira, "Crystalline Polymorphism of Organic Compounds", Topics in Current Chemistry, Jan. 1, 1998 (Jan. 1, 1998), vol. 198, p. 163-208.

International Search Report and Written Opinion of the International Searching Authority issued in corresponding application PCT/US2021/070924 dated Oct. 15, 2021 (15 pages).

*Primary Examiner* — Brian E McDowell
(74) *Attorney, Agent, or Firm* — Carter, DeLuca & Farrell LLP

(57) ABSTRACT

The present disclosure encompasses solid state forms of Belumosudil, in embodiments crystalline polymorphs of Belumosudil or salts thereof, processes for preparation thereof, and pharmaceutical compositions thereof.

10 Claims, 33 Drawing Sheets

SOLID STATE FORMS OF BELUMOSUDIL AND BELUMOSUDIL SALTS

CROSS REFERENCE TO RELATED APPLICATIONS

This application is a Continuation of, and claims priority to and the benefit of, International Patent Application No. PCT/US2021/070924, filed Jul. 22, 2021, which, in turn, claims the benefit of and priority to, U.S. Provisional Application No. 63/054,918, filed Jul. 22, 2020; U.S. Provisional Application No. 63/075,368, filed Sep. 8, 2020; U.S. Provisional Application No. 63/104,329 filed Oct. 22, 2020; and U.S. Provisional Application No. 63/137,212, filed Jan. 14, 2021, the entire disclosures of each of which are incorporated by reference herein.

FIELD OF THE DISCLOSURE

The present disclosure encompasses solid state forms of Belumosudil, in embodiments crystalline polymorphs of Belumosudil or salts thereof, processes for preparation thereof, and pharmaceutical compositions thereof.

BACKGROUND OF THE DISCLOSURE

Belumosudil, 2-(3-(4-((1H-Indazol-5-yl)amino)quinazolin-2-yl)phenoxy)-N-isopropylacetamide, has the following chemical structure:

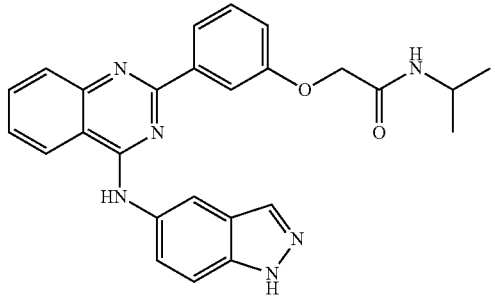 [SMILES: CC(C)NC(=O)COc1cccc(-c2nc(Nc3ccc4[nH]ncc4c3)c3ccccc3n2)c1]

Belumosudil is a ROCK2 inhibitor, and it is developed for the treatment of Graft-Versus-Host Disease including Chronic Graft-Versus-Host Disease, Systemic Sclerosis including Diffuse Cutaneous Systemic Sclerosis, Fibrosis including Idiopathic Pulmonary Fibrosis, Plaque Psoriasis, and Systemic Scleroderma.

The compound is described in International Publication No. WO 2006/105081. Crystalline forms of Belumosudil are disclosed in International Publication No. WO 2021/129589.

Polymorphism, the occurrence of different crystalline forms, is a property of some molecules and molecular complexes. A single molecule may produce a rise to a variety of polymorphs having distinct crystal structures and physical properties like melting point, thermal behaviors (e.g., measured by thermogravimetric analysis ("TGA"), or differential scanning calorimetry ("DSC")), X-ray diffraction (XRD) pattern, infrared absorption fingerprint, and solid state ($^{13}$C) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also produce a rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, including a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Belumosudil, and Belumosudil salts.

SUMMARY OF THE DISCLOSURE

The present disclosure provides crystalline polymorphs of Belumosudil and salts thereof, including Belumosudil Mesylate, Belumosudil Tosylate and/or Belumosudil Besylate, processes for preparation thereof, and pharmaceutical compositions thereof. These crystalline polymorphs can be used to prepare other solid state forms of Belumosudil, Belumosudil salts and their solid state forms.

The present disclosure also provides uses of the said solid state forms of API or salts thereof, including Belumosudil Mesylate, Belumosudil Tosylate and/or Belumosudil Besylate, in the preparation of other solid state forms of Belumosudil or salts thereof.

The present disclosure provides crystalline polymorphs of Belumosudil or salts thereof, including Belumosudil Mesylate, Belumosudil Tosylate and Belumosudil Besylate, for use in medicine, including for the treatment of Graft-Versus-Host Disease including Chronic Graft-Versus-Host Disease, Systemic Sclerosis including Diffuse Cutaneous Systemic Sclerosis, Fibrosis including Idiopathic Pulmonary Fibrosis, Plaque Psoriasis, Systemic Scleroderma. Particularly, the present disclosure provides crystalline polymorphs of Belumosudil or salts thereof, including Belumosudil Mesylate, Belumosudil Tosylate and Belumosudil Besylate, for use in medicine, including for the treatment of Chronic Graft-Versus-Host Disease and/or Systemic Sclerosis.

The present disclosure also encompasses the use of crystalline polymorphs of Belumosudil, or salts thereof, including Belumosudil Mesylate, Belumosudil Tosylate and Belumosudil Besylate of the present disclosure for the preparation of pharmaceutical compositions and/or formulations.

In another aspect, the present disclosure provides pharmaceutical compositions comprising crystalline polymorphs of Belumosudil or salts thereof, including Belumosudil Mesylate, Belumosudil Tosylate and Belumosudil Besylate according to the present disclosure.

The present disclosure includes processes for preparing the above mentioned pharmaceutical compositions. The processes include combining any one or a combination of the crystalline polymorphs of Belumosudil or salts thereof, including Belumosudil Mesylate, Belumosudil Tosylate and Belumosudil Besylate with at least one pharmaceutically acceptable excipient.

The crystalline polymorphs of Belumosudil or salts thereof, including Belumosudil Mesylate, Belumosudil Tosylate and Belumosudil Besylate as defined herein and the pharmaceutical compositions or formulations of the crystalline polymorph of Belumosudil or salts thereof, including Belumosudil Mesylate, Belumosudil Tosylate and Belumosudil Besylate may be used as medicaments, such as for the treatment of Graft-Versus-Host Disease including Chronic Graft-Versus-Host Disease, Systemic Sclerosis including Diffuse Cutaneous Systemic Sclerosis, Fibrosis including Idiopathic Pulmonary Fibrosis, Plaque Psoriasis, Systemic Scleroderma. Particularly, the crystalline polymorphs of Belumosudil or salts thereof, including Belumosudil Mesylate, Belumosudil Tosylate and Belumosudil Besylate as defined herein and the pharmaceutical compositions or formulations of the crystalline polymorph of Belumosudil or salts thereof, including Belumosudil Mesylate, Belumosudil Tosylate and/or Belumosudil Besylate may be used as medicaments, for the treatment of Chronic Graft-Versus-Host Disease and/or Systemic Sclerosis.

The present disclosure also provides methods of treating Graft-Versus-Host Disease including Chronic Graft-Versus-Host Disease, Systemic Sclerosis including Diffuse Cutaneous Systemic Sclerosis, Fibrosis including Idiopathic Pulmonary Fibrosis, Plaque Psoriasis, Systemic Scleroderma, by administering a therapeutically effective amount of any one or a combination of the crystalline polymorphs of Belumosudil or salts thereof, including Belumosudil Mesylate, Belumosudil Tosylate and Belumosudil Besylate of the present disclosure, or at least one of the above pharmaceutical compositions, to a subject suffering from Graft-Versus-Host Disease including Chronic Graft-Versus-Host Disease, Systemic Sclerosis including Diffuse Cutaneous Systemic Sclerosis, Fibrosis including Idiopathic Pulmonary Fibrosis, Plaque Psoriasis, Systemic Scleroderma, or otherwise in need of the treatment. Particularly, the present disclosure provides methods of treating Chronic Graft-Versus-Host Disease and/or Systemic Sclerosis, by administering a therapeutically effective amount of any one or a combination of the crystalline polymorphs of Belumosudil or salts thereof, including Belumosudil Mesylate, Belumosudil Tosylate and Belumosudil Besylate of the present disclosure, or at least one of the above pharmaceutical compositions, to a subject suffering from Chronic Graft-Versus-Host Disease and/or Systemic Sclerosis, or otherwise in need of the treatment.

The present disclosure also provides uses of crystalline polymorphs of Belumosudil or salts thereof, including Belumosudil Mesylate, Belumosudil Tosylate and/or Belumosudil Besylate of the present disclosure, or at least one of the above pharmaceutical compositions, for the manufacture of medicaments for treating e.g., Graft-Versus-Host Disease including Chronic Graft-Versus-Host Disease, Systemic Sclerosis including Diffuse Cutaneous Systemic Sclerosis, Fibrosis including Idiopathic Pulmonary Fibrosis, Plaque Psoriasis, Systemic Scleroderma, and particularly for treating Chronic Graft-Versus-Host Disease and/or Systemic Sclerosis.

DETAILED DESCRIPTION OF THE DISCLOSURE

Figure 1:
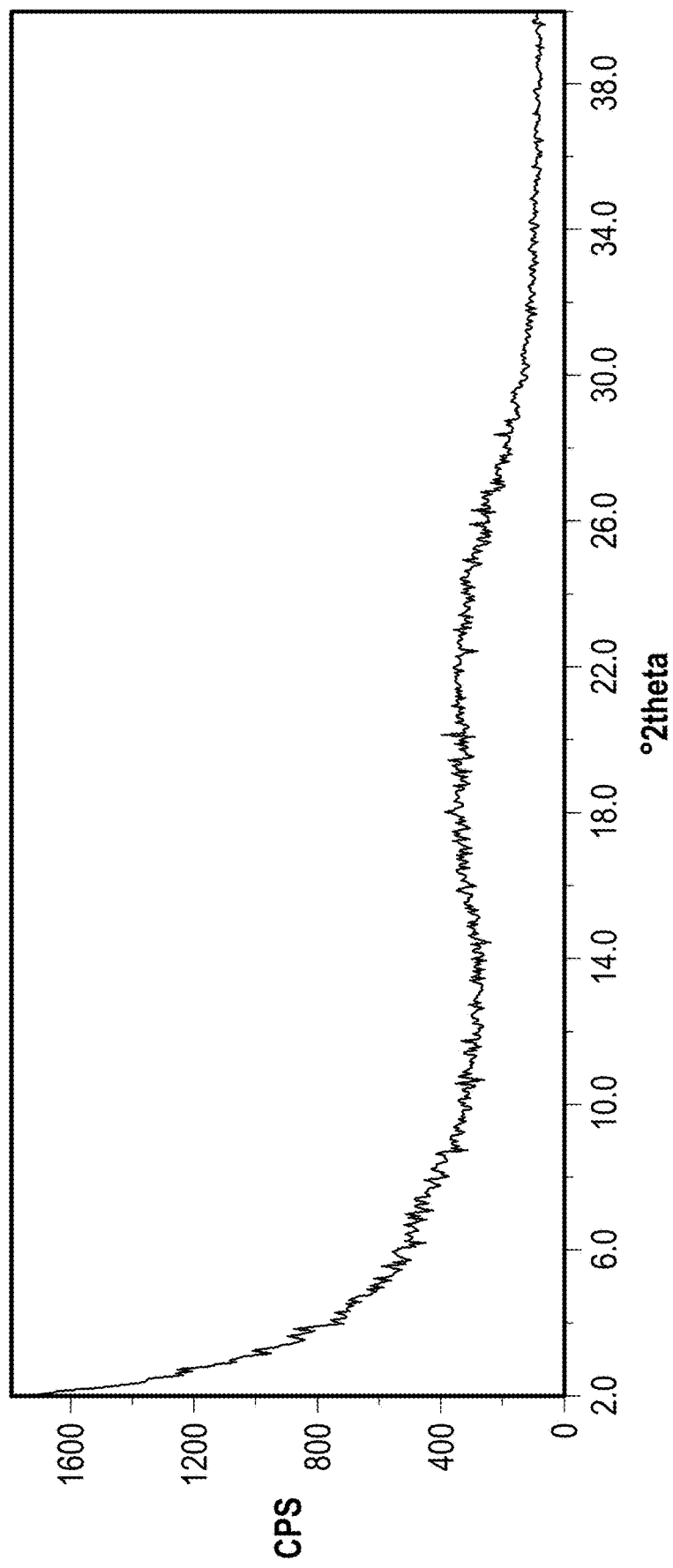
FIG. 1 shows an X-ray powder diffraction pattern (XRPD) of amorphous Belumosudil.

The present disclosure encompasses solid state forms of Belumosudil and salts thereof, including crystalline polymorphs of Belumosudil and salts thereof, including Belumosudil Mesylate, Belumosudil Tosylate and/or Belumosudil Besylate processes for preparation thereof, and pharmaceutical compositions thereof.

Solid state properties of Belumosudil, Belumosudil salts, and crystalline polymorphs thereof can be influenced by controlling the conditions under which Belumosudil and Belumosudil salts, and crystalline polymorphs thereof are obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of Belumosudil or Belumosudil salt, described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of Belumosudil or Belumosudil salt. In some embodiments of the disclosure, the described crystalline polymorph of Belumosudil or Belumosudil salt, may contain from about 1% to about 20% (w/w), from about 5% to about 20% (w/w), or from about 5% to about 10% (w/w) of one or more other crystalline polymorph of the same Belumosudil or Belumosudil salt. Similarly, a crystalline polymorph of Belumosudil salt (e.g. Belumosudil Mesylate, Belumosudil Tosylate or Belumosudil Besylate) described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of the Belumosudil salt (e.g. Belumosudil Mesylate, Belumosudil Tosylate or Belumosudil Besylate). In some embodiments of the disclosure, the described crystalline polymorph of Belumosudil salt (e.g., Belumosudil Mesylate, Belumosudil Tosylate or Belumosudil Besylate) may contain from about 1% to about 20% (w/w), from about 5% to about 20% (w/w), or from about 5% to about 10% (w/w) of one or more other crystalline polymorph of the same Belumosudil salt (e.g., Belumosudil Mesylate, Belumosudil Tosylate or Belumosudil Besylate).

Depending on which other crystalline polymorphs a comparison is made, the crystalline polymorphs of Belumosudil and Belumosudil salts (e.g. Belumosudil Mesylate, Belumosudil Tosylate or Belumosudil Besylate) of the present disclosure may have advantageous properties selected from at least one of the following: chemical purity, flowability, solubility, dissolution rate, morphology or crystal habit, stability, such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Belumosudil or Belumosudil salt, referred to herein as being characterized by graphical data "as depicted in" or "as substantially depicted in" a Figure will thus be understood to include any crystal forms of Belumosudil or Belumosudil salt, characterized with the graphical data having such small variations, as are well known to the skilled person, in comparison with the Figure.

As used herein, and unless stated otherwise, the term "anhydrous" in relation to crystalline forms of Belumosudil, Belumosudil Mesylate, Belumosudil Tosylate and/or Belumosudil Besylate, relates to a crystalline form of Belumosudil or Belumosudil salt which does not include any crystalline water (or other solvents) in a defined, stoichiometric amount within the crystal. Moreover, an "anhydrous" form would generally not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, the term "isolated" in reference to crystalline polymorph of Belumosudil, or Belumosudil salt (e.g., Belumosudil Mesylate, Belumosudil Tosylate and/or Belumosudil Besylate) of the present disclosure corresponds to a crystalline polymorph of Belumosudil or Belumosudil salt, that is physically separated from the reaction mixture in which it is formed.

As used herein, unless stated otherwise, the XRPD measurements are taken using copper Kα radiation wavelength 1.5418 Å. XRPD peaks reported herein are measured using CuKα radiation, λ=1.5418 Å, typically at a temperature of 25±3° C.

As used herein, $^{13}$C NMR spectra are preferably measured at 125 MHz at magic angle spinning (MAS) frequency ωr/2π=11 kHz As used herein, unless stated otherwise, TGA analysis is preferably carried out at a heating rate of 10° C./min to 250° C., preferably with a nitrogen flow of 40 ml/min.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in some cases about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

Figure 2:
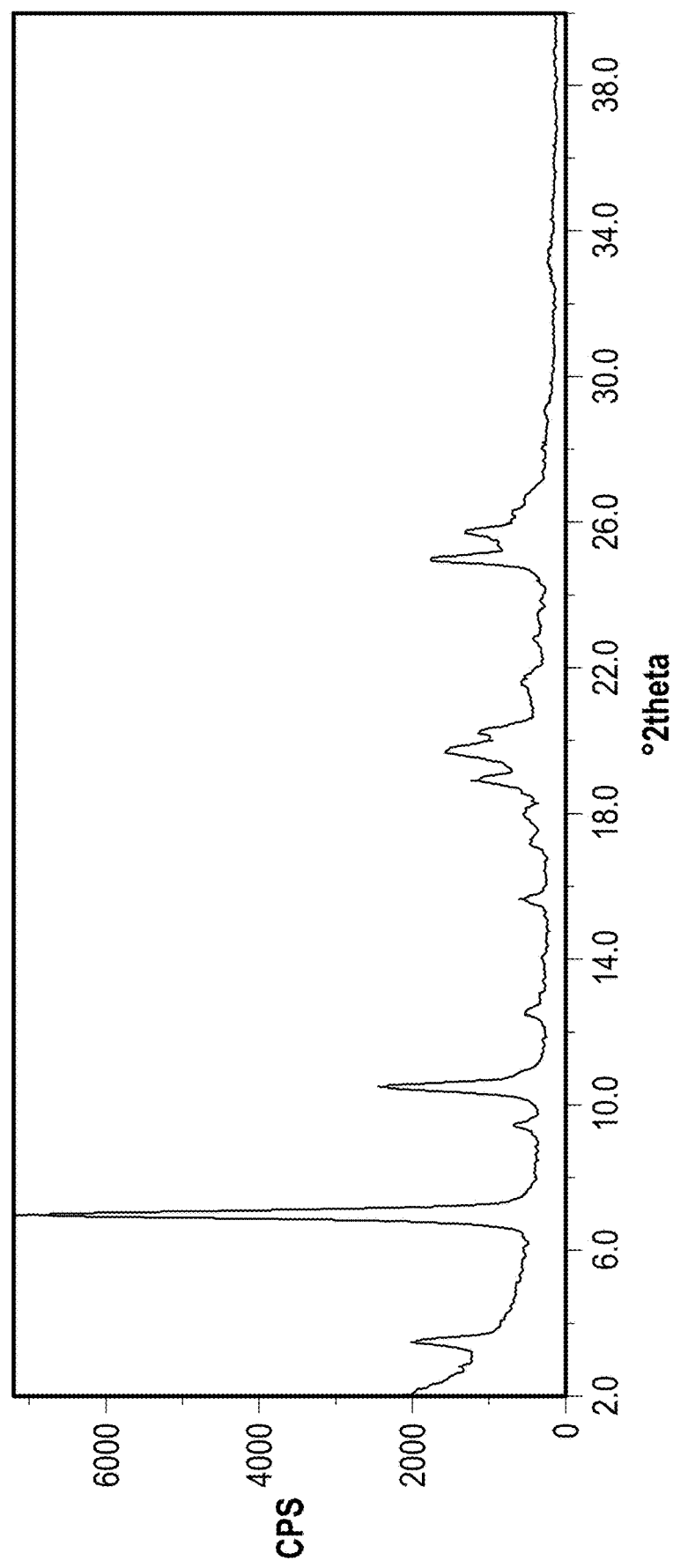
FIG. 2 shows a characteristic X-ray powder diffraction pattern (XRPD) of Belumosudil Form B1.

The present disclosure includes a crystalline polymorph of Belumosudil, designated form B1. The crystalline Form B1 of Belumosudil may be characterized by data selected from one or more of the following: an X-ray powder diffraction pattern substantially as depicted in FIG. 2; an X-ray powder diffraction pattern having peaks at 3.5, 6.9, 10.5, 24.9 and 25.7 degrees 2-theta±0.2 degrees 2-theta; and combinations of these data.

Crystalline Form B1 of Belumosudil may be further characterized by an X-ray powder diffraction pattern having peaks at 3.5, 6.9, 10.5, 24.9 and 25.7 degrees 2-theta±0.2 degrees 2-theta, and also having any one, two, three, four or five additional peaks selected from 9.4, 12.5, 15.7, 18.9 and 19.7 degrees 2-theta±0.2 degrees 2-theta.

Crystalline Form B1 of Belumosudil may be alternatively characterized by an X-ray powder diffraction pattern having peaks at 3.5, 6.9, 9.4, 10.5, 12.5, 15.7, 18.9, 19.7, 24.9, and 25.7 degrees 2-theta±0.2 degrees 2-theta.

In one embodiment of the present disclosure, crystalline Form B1 of Belumosudil is isolated.

Crystalline Form B1 of Belumosudil may be characterized by each of the above characteristics alone/or by all possible combinations, e.g., an XRPD pattern having peaks at 3.5, 6.9, 10.5, 24.9 and 25.7 degrees 2-theta±0.2 degrees 2-theta; an XRPD pattern as depicted in FIG. 2, and combinations thereof.

Figure 3:
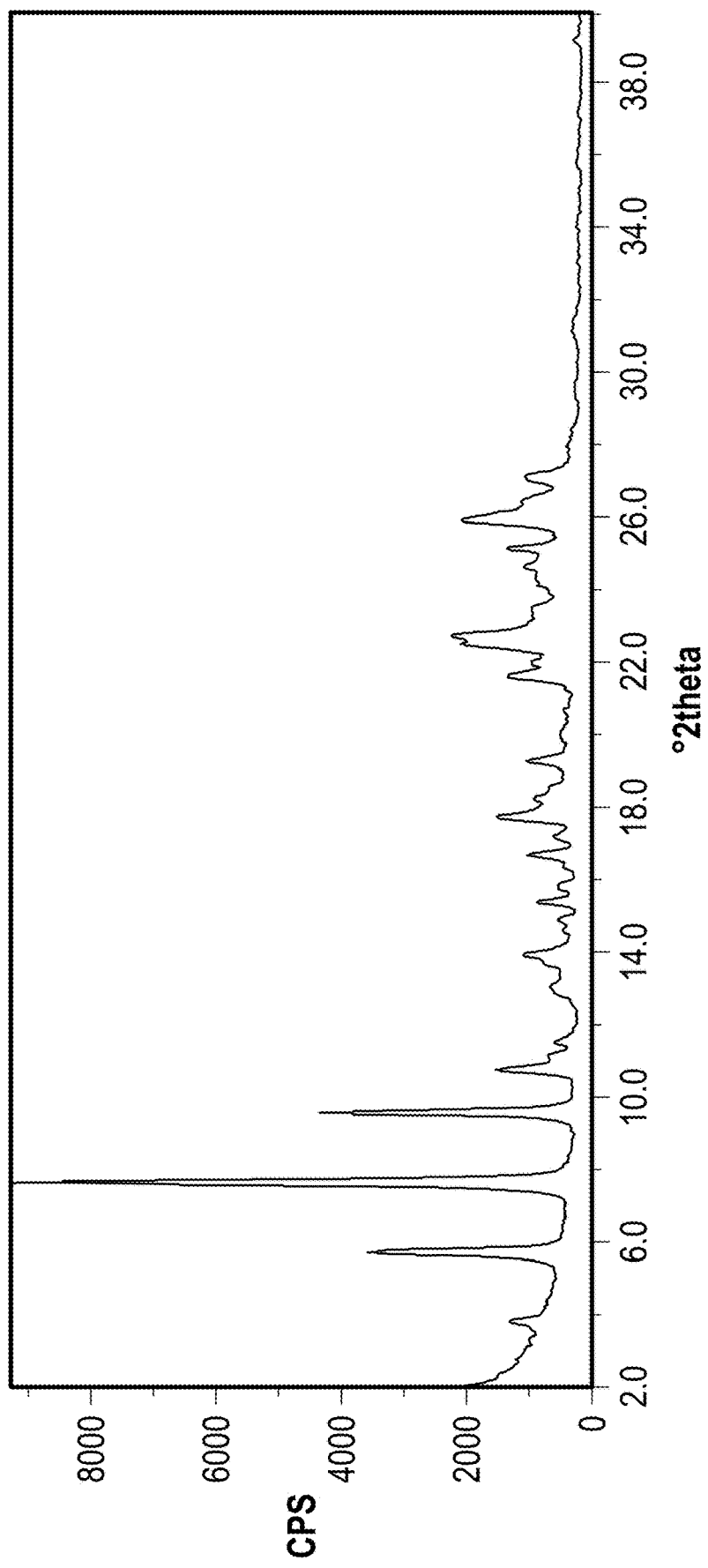
FIG. 3 shows a characteristic X-ray powder diffraction pattern (XRPD) of Belumosudil Form B2.

The present disclosure includes a crystalline polymorph of Belumosudil, designated form B2. The crystalline Form B2 of Belumosudil may be characterized by data selected from one or more of the following: an X-ray powder diffraction pattern substantially as depicted in FIG. 3; an X-ray powder diffraction pattern having peaks at 3.8, 5.7, 7.6, 9.6 and 25.9 degrees 2-theta±0.2 degrees 2-theta; and combinations of these data.

Crystalline Form B2 of Belumosudil may be further characterized by an X-ray powder diffraction pattern having peaks at 3.8, 5.7, 7.6, 9.6 and 25.9 degrees 2-theta±0.2 degrees 2-theta, and also having any one, two, three, four or five additional peaks selected from 10.7, 15.4, 16.6, 17.8 and 19.3 degrees 2-theta±0.2 degrees 2-theta.

Crystalline Form B2 of Belumosudil may be alternatively characterized by an X-ray powder diffraction pattern having peaks at 3.8, 5.7, 7.6, 9.6, 10.7, 15.4, 16.6, 17.8, 19.3 and 25.9 degrees 2-theta±0.2 degrees 2-theta.

In one embodiment of the present disclosure, crystalline Form B2 of Belumosudil is isolated.

Crystalline Form B2 of Belumosudil may be characterized by each of the above characteristics alone/or by all possible combinations, e.g., an XRPD pattern having peaks at 3.8, 5.7, 7.6, 9.6 and 25.9 degrees 2-theta±0.2 degrees 2-theta; an XRPD pattern as depicted in FIG. 3, and combinations thereof.

Figure 4:
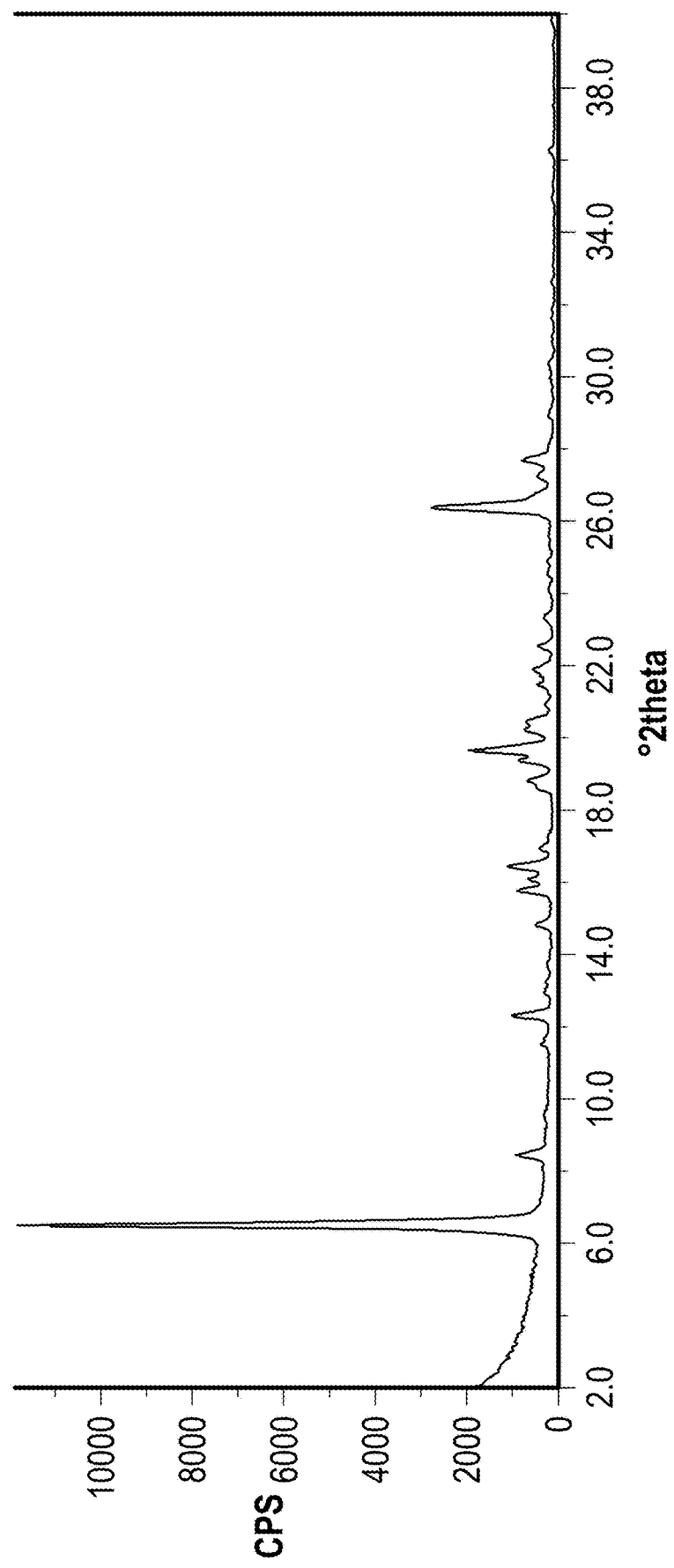
FIG. 4 shows a characteristic X-ray powder diffraction pattern (XRPD) of Belumosudil Form B3.

The present disclosure includes a crystalline polymorph of Belumosudil, designated form B3. The crystalline Form B3 of Belumosudil may be characterized by data selected from one or more of the following: an X-ray powder diffraction pattern substantially as depicted in FIG. 4; an X-ray powder diffraction pattern having peaks at 6.5, 8.4, 12.2, 19.6 and 26.3 degrees 2-theta±0.2 degrees 2-theta; and combinations of these data.

Crystalline Form B3 of Belumosudil may be further characterized by an X-ray powder diffraction pattern having peaks at 6.5, 8.4, 12.2, 19.6 and 26.3 degrees 2-theta±0.2 degrees 2-theta, and also having any one, two, three, four or five additional peaks selected from 14.7, 15.4, 16.4, 18.8 and 22.5 degrees 2-theta±0.2 degrees 2-theta.

Crystalline Form B3 of Belumosudil may be alternatively characterized by an X-ray powder diffraction pattern having peaks at 6.5, 8.4, 12.2, 14.7, 15.4, 16.4, 18.8, 19.6, 22.5, and 26.3 degrees 2-theta±0.2 degrees 2-theta.

In one embodiment of the present disclosure, crystalline Form B3 of Belumosudil is isolated.

Crystalline Form B3 of Belumosudil may be characterized by each of the above characteristics alone/or by all possible combinations, e.g., an XRPD pattern having peaks at 6.5, 8.4, 12.2, 19.6 and 26.3 degrees 2-theta±0.2 degrees 2-theta; an XRPD pattern as depicted in FIG. 4, and combinations thereof.

Figure 6:
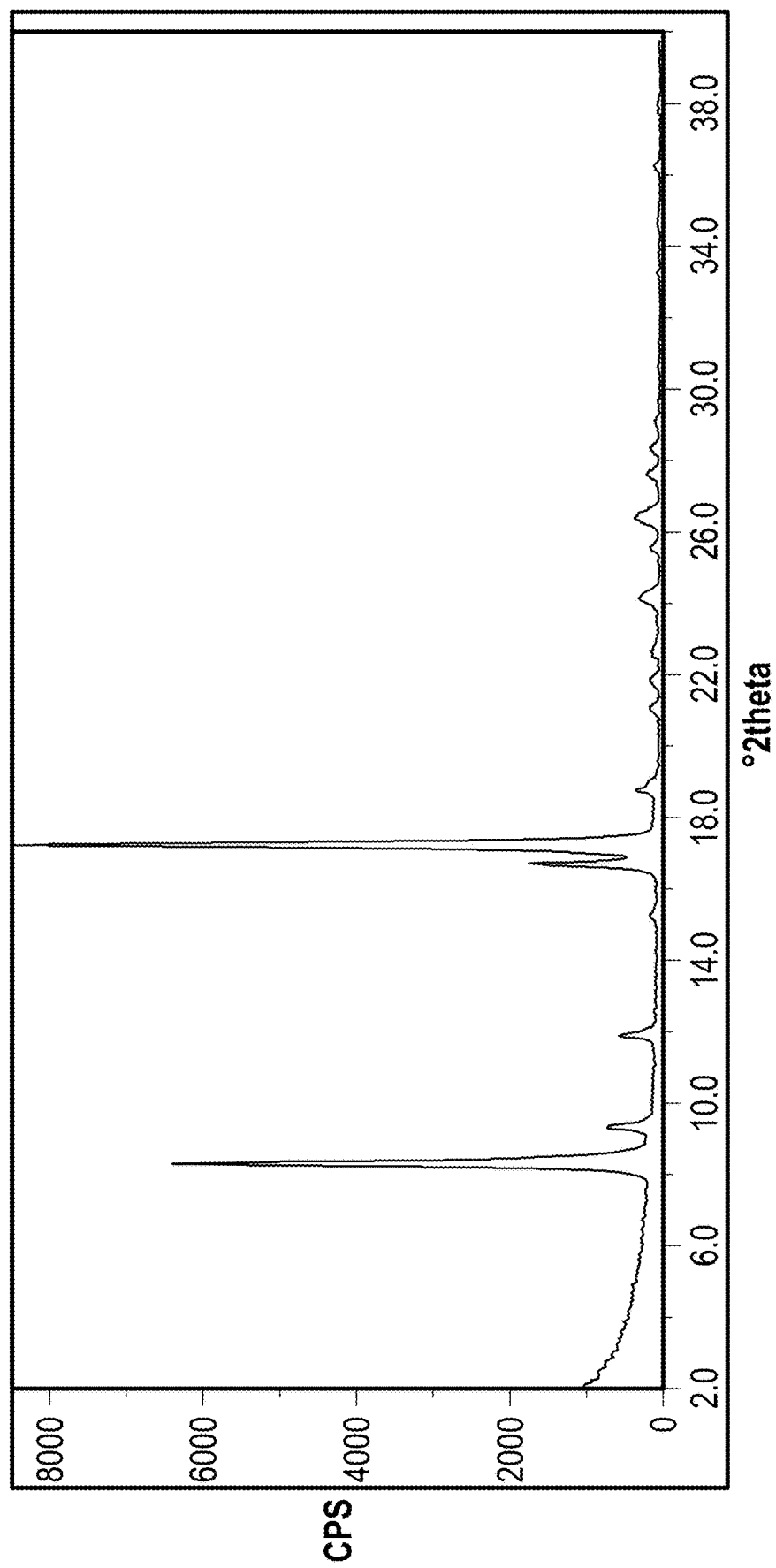
FIG. 6 shows a characteristic X-ray powder diffraction pattern (XRPD) of Belumosudil form B4.

The present disclosure includes a crystalline polymorph of Belumosudil, designated form B4. The crystalline Form B4 of Belumosudil may be characterized by data selected from one or more of the following: an X-ray powder diffraction pattern substantially as depicted in FIG. 6; an X-ray powder diffraction pattern having peaks at 8.3, 9.3, 11.9, 16.7 and 17.2 degrees 2-theta±0.2 degrees 2-theta; and combinations of these data.

Crystalline Form B4 of Belumosudil may be further characterized by an X-ray powder diffraction pattern having peaks at 8.3, 9.3, 11.9, 16.7 and 17.2 degrees 2-theta±0.2 degrees 2-theta, and also having any one, two, three, four or five additional peaks selected from 15.2, 18.7, 24.1, 25.6 and 26.2 degrees 2-theta±0.2 degrees 2-theta.

Crystalline Form B4 of Belumosudil may be further characterized by an X-ray powder diffraction pattern having peaks at 8.3, 9.3, 11.9, 16.7 and 17.2 degrees 2-theta±0.2 degrees 2-theta, and also having any one, two, three, four or five additional peaks selected from 15.2, 18.7, 24.1, 25.6 and 26.2 degrees 2-theta±0.2 degrees 2-theta.

Crystalline Form B4 of Belumosudil may be alternatively characterized by an X-ray powder diffraction pattern having peaks at 8.3, 9.3, 11.9, 15.2, 16.7, 17.2, 18.7, 24.1, 25.6, and 26.2 degrees 2-theta±0.2 degrees 2-theta.

In one embodiment of the present disclosure, crystalline Form B4 of Belumosudil is isolated.

Crystalline Form B4 of Belumosudil may be characterized by each of the above characteristics alone/or by all possible combinations, e.g., an XRPD pattern having peaks at 8.3, 9.3, 11.9, 16.7 and 17.2 degrees 2-theta±0.2 degrees 2-theta; an XRPD pattern as depicted in FIG. 6, and combinations thereof.

Figure 9:
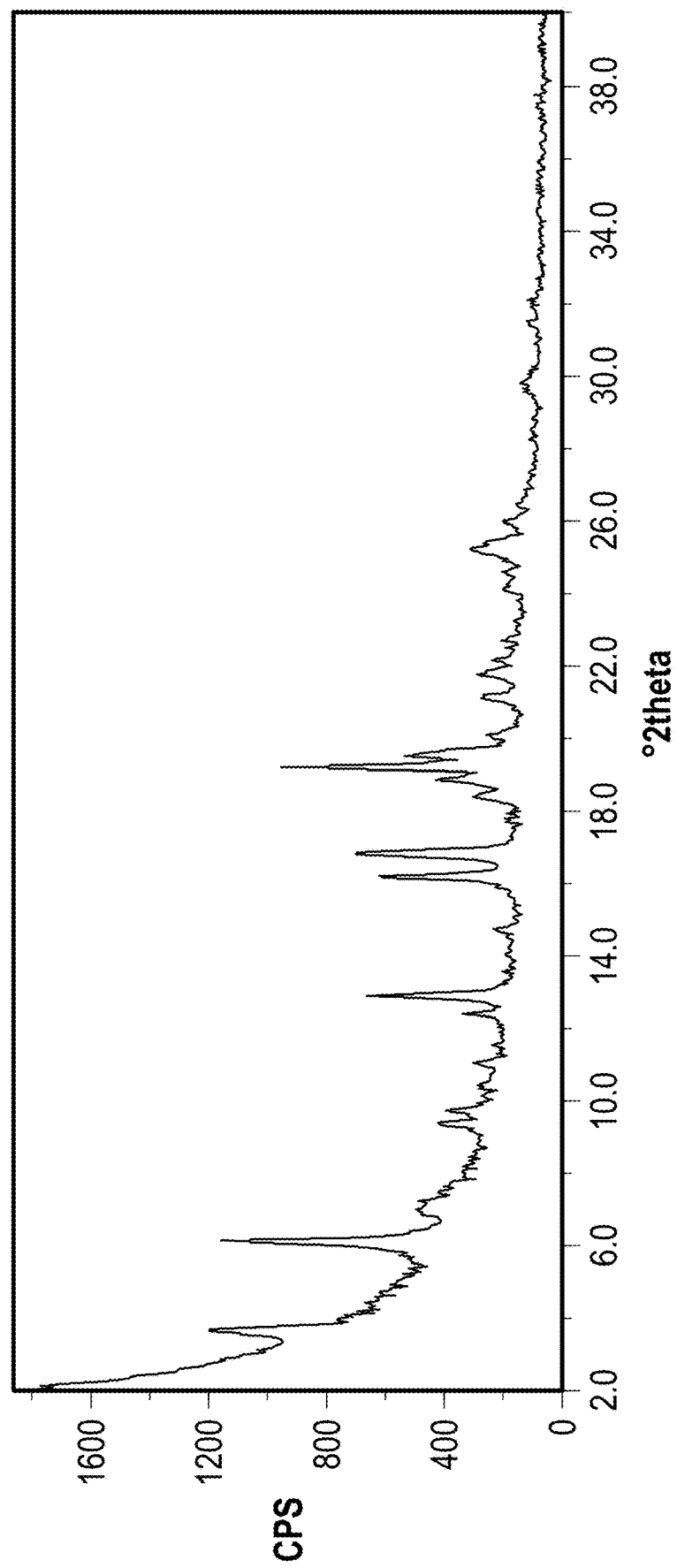
FIG. 9 shows a characteristic X-ray powder diffraction pattern (XRPD) of Belumosudil form B5.

The present disclosure includes a crystalline polymorph of Belumosudil, designated form B5. The crystalline Form B5 of Belumosudil may be characterized by data selected from one or more of the following: an X-ray powder diffraction pattern substantially as depicted in FIG. 9; an X-ray powder diffraction pattern having peaks at 6.1, 12.9, 16.2, 16.8 and 19.2 degrees 2-theta±0.2 degrees 2-theta; and combinations of these data.

Crystalline Form B5 of Belumosudil may be further characterized by an X-ray powder diffraction pattern having peaks at 6.1, 12.9, 16.2, 16.8 and 19.2 degrees 2-theta±0.2 degrees 2-theta, and also having any one, two, three, four or five additional peaks selected from 3.7, 9.4, 9.8, 12.4 and 18.4 degrees 2-theta±0.2 degrees 2-theta.

Crystalline Form B5 of Belumosudil may be alternatively characterized by an X-ray powder diffraction pattern having peaks at 3.7, 6.1, 9.4, 9.8, 12.4, 12.9, 16.2, 16.8, 18.4, and 19.2 degrees 2-theta±0.2 degrees 2-theta.

In one embodiment of the present disclosure, crystalline Form B5 of Belumosudil is isolated.

Crystalline Form B5 of Belumosudil may be characterized by each of the above characteristics alone/or by all possible combinations, e.g., an XRPD pattern having peaks at 6.1, 12.9, 16.2, 16.8 and 19.2 degrees 2-theta±0.2 degrees 2-theta; an XRPD pattern as depicted in FIG. 9, and combinations thereof.

Figure 5:
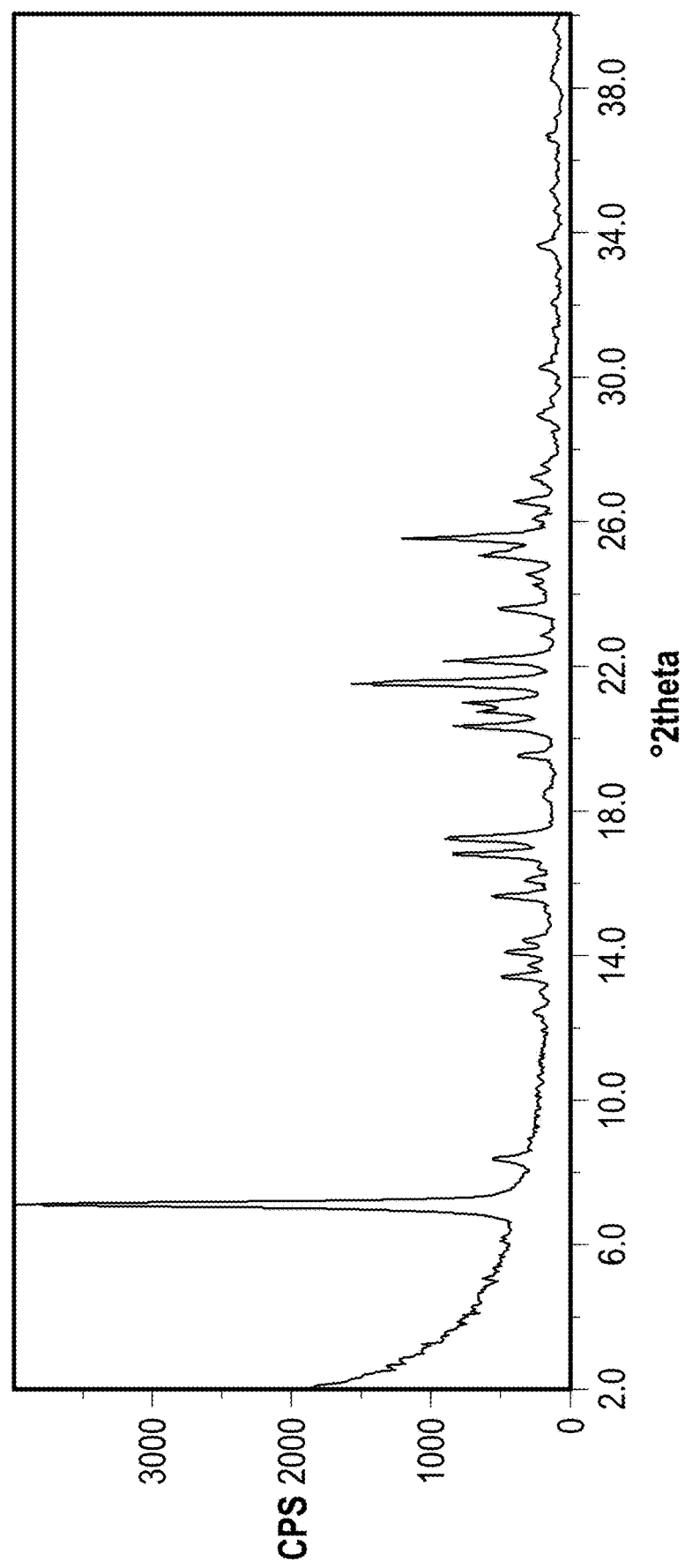
FIG. 5 shows a characteristic X-ray powder diffraction pattern (XRPD) of Belumosudil Mesylate Form M1.

The present disclosure includes a crystalline polymorph of Belumosudil Mesylate, designated form M1. The crystalline Form M1 of Belumosudil Mesylate may be characterized by data selected from one or more of the following: an X-ray powder diffraction pattern substantially as depicted in FIG. 5; an X-ray powder diffraction pattern having peaks at 7.1, 17.2, 20.3, 21.5 and 25.5 degrees 2-theta±0.2 degrees 2-theta; a solid state $^{13}$C NMR spectrum with characteristic peaks at 137.8, 133.8, 122.5, 118.3 and 111.6 ppm±0.2 ppm; a solid state $^{13}$C NMR spectrum having the following chemical shift absolute differences from reference peak at 167.2 ppm±1 ppm: 29.4, 33.4, 44.7, 48.9 and 55.6 ppm±0.1 ppm; a solid state $^{13}$C NMR spectrum substantially as depicted in any of FIGS. 16, 17 and 18; and combinations of these data.

Crystalline Form M1 of Belumosudil Mesylate may be further characterized by an X-ray powder diffraction pattern having peaks at 7.1, 17.2, 20.3, 21.5 and 25.5 degrees 2-theta±0.2 degrees 2-theta, and also having any one, two, three, four or five additional peaks selected from 8.4, 15.5, 16.8, 19.5 and 22.1 degrees 2-theta±0.2 degrees 2-theta.

Crystalline form M1 of Belumosudil Mesylate may be alternatively characterized by X-ray powder diffraction pattern having peaks at 7.1, 8.4, 15.5, 16.8, 17.2, 19.5, 20.3, 21.5, 22.1 and 25.5 degrees 2-theta±0.2 degrees 2-theta.

According to any aspect or embodiment as described herein, crystalline form M1 of Belumosudil Mesylate may be an anhydrous form, as can be determined by TGA. According to any aspect or embodiment as described herein, crystalline form M1 of Belumosudil Mesylate may contain 0.5% w/w or less, or 0.2% w/w or less, or 0.1 wt % or less, of total residual solvent. The residual solvent may be one or more polar solvents, preferably water, alcohols (particularly $C_{1-4}$ alcohols, especially methanol, ethanol, isopropanol, 1-propanol, or n-butanol) or halogenated solvents (particularly 2,2,2-trifluoroethanol or dichloromethane), or DMSO, or mixtures thereof. Particularly, crystalline form M1 of Belumosudil Mesylate according to any aspect or embodiment of the disclosure may contain 0.5% w/w or less, or 0.2% w/w or less, or 0.1 wt % or less, of total residual solvent, wherein the residual solvent is: ethanol, water, or DMSO, or a combination of ethanol, water and DMSO and water, or a combination of ethanol and DMSO. Alternatively, crystalline form M1 of Belumosudil Mesylate according to any aspect or embodiment of the disclosure may contain 0.5% w/w or less, or 0.2% w/w or less, or 0.1 wt % or less, of ethanol, or 0.5% w/w or less, or 0.2 w/w or less, or 0.1 wt % or less, of a mixture of ethanol and DMSO.

In one embodiment of the present disclosure, crystalline Form M1 of Belumosudil Mesylate is isolated. Particularly, crystalline form M1 of Belumosudil Mesylate according to any aspect or embodiment of the disclosure may be isolated.

According to any aspect or embodiment of the present disclosure, crystalline Form M1 of Belumosudil Mesylate is non-hygroscopic. Particularly, Form M1 of Belumosudil Mesylate according to any aspect or embodiment is polymorphically stable at up to 100% relative humidity at room temperature for at least 7 days.

Crystalline Form M1 of Belumosudil Mesylate may be characterized by each of the above characteristics alone/or by all possible combinations, e.g., an XRPD pattern having peaks at 7.1, 17.2, 20.3, 21.5 and 25.5 degrees 2-theta±0.2 degrees 2-theta; an XRPD pattern as depicted in FIG. 5, and combinations thereof.

Crystalline form M1 of Belumosudil Mesylate may be prepared by crystallisation from a mixture comprising Belumosudil Mesylate and one or more polar solvents, preferably a polar organic solvent, and particularly wherein the polar solvent is an alcohol or halogenated solvent, or mixtures thereof. Examples of suitable solvents include, but are not limited to, methanol, ethanol, isopropanol, 1-propanol, n-butanol, dichloromethane, and combinations thereof; and preferably ethanol, isopropanol, n-butanol or 1-propanol. In any aspect or embodiment of the present disclosure for preparing form M1, the process may comprise:

(a) providing a mixture of Belumosudil Mesylate in at least one polar solvent, optionally with heating;
(b) optionally stirring the mixture, optionally at elevated temperature;

(c) optionally cooling the mixture, preferably to room temperature;
(d) optionally stirring the cooled mixture; and
(e) optionally isolating crystalline form M1 of Belumosudil Mesylate from the mixture.

The mixture in step (a) may be prepared by:
(i) providing a mixture of Belumosudil free base in a polar solvent;
(ii) combining the mixture with Methanesulfonic acid;
(iii) optionally heating the mixture; and
(iv) optionally adding a further polar solvent.

Preferably, the process for preparing Form M1 of Belumosudil Mesylate according to any embodiment described herein is carried out in the absence of water or substantially in the absence of water, particularly 2 wt % or less, 1 wt % or less, 0.5 wt % or less, 0.2 wt % or less, or 0.1 wt % or less of water.

According to any embodiment of the process for preparing form M1, the solvent in step (i) is preferably an organic solvent, particularly comprising an alcohol, a halogenated solvent, or mixtures thereof. Preferably the solvent is selected from the group consisting of methanol, ethanol, isopropanol, 1-propanol, n-butanol, and dichloromethane or mixtures thereof, and particularly, ethanol, isopropanol, 1-propanol, n-butanol.

In step (i), the ratio of solvent to Belumosudil may be: about 10 to about 40 ml per gram of Belumosudil, about 14 to about 35 ml per gram of Belumosudil or about 16 to about 20 to about 32 ml per gram of Belumosudil, or about 18 to about 24 ml per gram of Belumosudil, and optionally about 20 ml per gram of Belumosudil. The mixture in step (i) may be a solution or a slurry.

In step (ii) of the process for preparing form M1, combining of methanesulfonic acid to Belumosudil may be in any order. Preferably, methanesulfonic acid may be added to the mixture of Belumosudil in the solvent. The addition may be carried out portion-wise or dropwise. The methanesulfonic acid is optionally added in an amount of: about 0.7 to about 1.5 molar equivalents, about 0.9 to about 1.3 molar equivalents, about 1.0 to about 1.2 molar equivalents, or about 1.1 molar equivalents relative to Belumosudil. Preferably, step (ii) comprises adding Methanesulfonic acid to the mixture of Belumosudil and solvent.

In step (iii) of the process for preparing form M1, the mixture may be optionally heated. The heating may be to a temperature of about 30° C. to about 70° C., about 40° C. to about 60° C., about 45° C. to about 55° C., or about 50° C.

In step (iv), a further polar solvent may be added to the reaction mixture. The further solvent may be any solvent which is a poor solvent for Belumosudil Mesylate, i.e., a solvent in which Belumosudil Mesylate has low solubility. The further polar solvent may be the same solvent as that used in step (i)) or may be different. The further solvent is preferably selected from the group consisting of methanol, ethanol, isopropanol, 1-propanol, n-butanol, and dichloromethane or mixtures thereof. Preferably, the further polar solvent in step (iv) is selected from methanol, ethanol, isopropanol, 1-propanol, and n-butanol. More preferably, the further polar solvent in step (iv) is ethanol. The further polar solvent in step (iv) can be added in any suitable amount. Preferably, the v/v ratio of the further polar solvent to the solvent in step (i) may be from: about 5:1 to about 1:5, or about 2:1 to about 1:2, or about 1.5:1 to about 1:1.5, or about 1.3:1 to about 1:1.3, and preferably about 1:1.3.

Alternatively, according to any embodiment of the process for preparing Form M1, the mixture in step (a) may be prepared by:

(i-a) combining Belumosudil Mesylate with a polar solvent, optionally with heating, to form a solution; and optionally
(ii-a) adding an organic antisolvent.

The polar solvent in step (i-a) is preferably an organic solvent, more preferably selected from the group consisting of, 2,2,2-Trifluoroethanol (TFE), and DMSO or mixtures thereof. Particularly, the solvent is selected from the group consisting of TFE and DMSO. In step (i-a), the ratio of solvent to Belumosudil Mesylate may be from: about 5 to about 50 ml, about 7 to about 40 ml, about 9 to about 35 ml, or about 10V to about 30 ml per gram of Belumosudil Mesylate.

The organic antisolvent in step (ii-a) can be any organic solvent in which Belumosudil Mesylate is poorly soluble. Preferably the organic antisolvent in step (ii-a) is selected from the group consisting of acetonitrile, dioxane, methyl ethyl ketone, methyl t-butyl ketone, ethanol, isopropanol, 1-propanol, n-butanol, and more particularly, ethanol.

In any embodiment of the process for preparing form M1, the mixture in step (a) may be a solution or a slurry. The mixture in step (a) is preferably in the form of a slurry. The mixture in step (a) may be at room temperature, or may be heated. The heating may be to a temperature of about 30° C. to about 70° C., about 40° C. to about 60° C., about 45° C. to about 55° C., or about 50° C. Alternatively, the mixture may be at room temperature.

In any embodiment of the process for preparing Form M1, step (b) is carried out, preferably by stirring at a temperature of: about 30° C. to about 70° C., about 40° C. to about 60° C., about 45° C. to about 55° C., or about 50° C. Alternatively, step (b) may be carried out at room temperature. The stirring may be carried out for any suitable time. Typically, the stirring may be carried out over a period of about 10 minutes to about 2 hours, about 20 minutes to about 1 hour, or about 45 minutes.

In any embodiment of the process for preparing Form M1, step (c) is carried out. Preferably, the cooling is to room temperature. After cooling, step (d) can be carried out, preferably by stirring the cooled mixture for a suitable time to prepare Belumosudil Mesylate Form M1. The stirring may be carried out for any suitable time, preferably for about 6 to about 96 hours, about 20 to about 80 hours, about 30 to about 50 hours, or about 40 hours.

In any embodiment of the process, step (e) may be carried out by any suitable method, for example by filtration, decantation or by centrifuge. Preferably the isolation of the solid is by filtration or by centrifuge, and more preferably by centrifuge.

In any embodiment the process may further comprise washing and/or drying steps.

Figure 7:
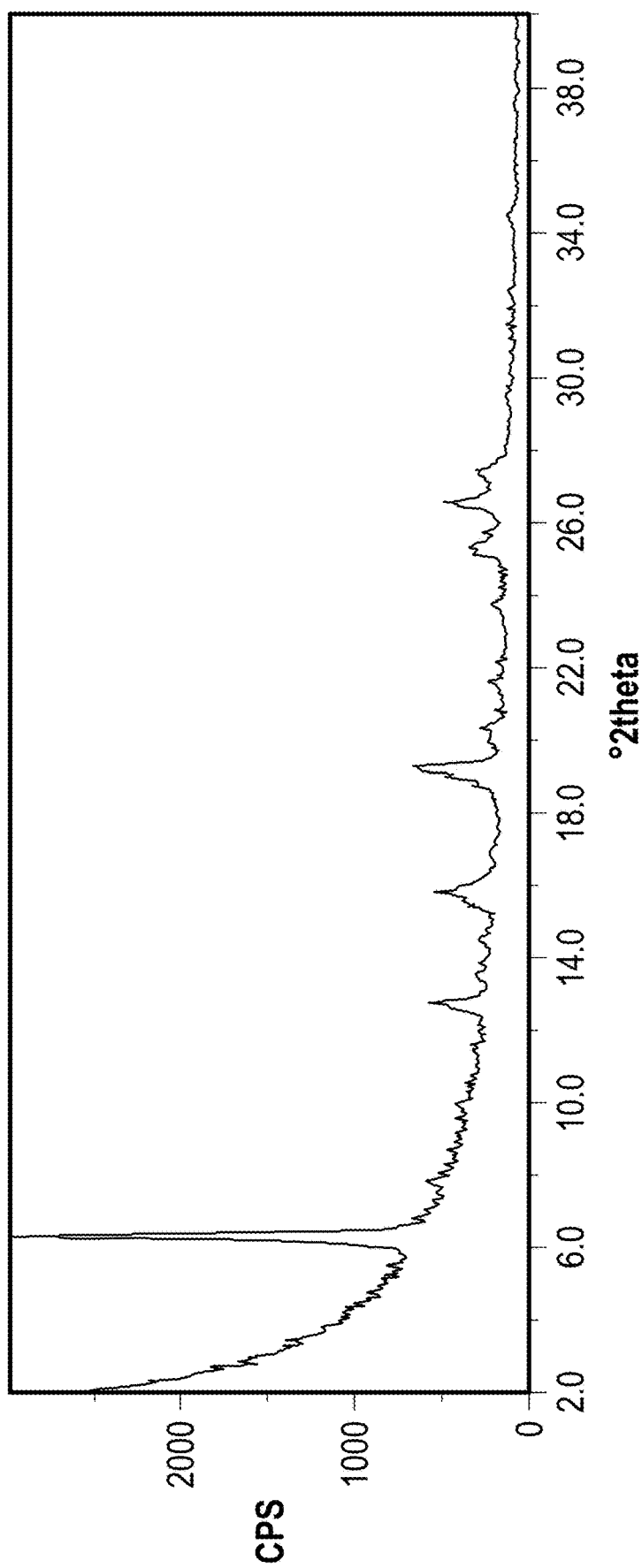
FIG. 7 shows a characteristic X-ray powder diffraction pattern (XRPD) of Belumosudil Mesylate form M2.
Figure 19:
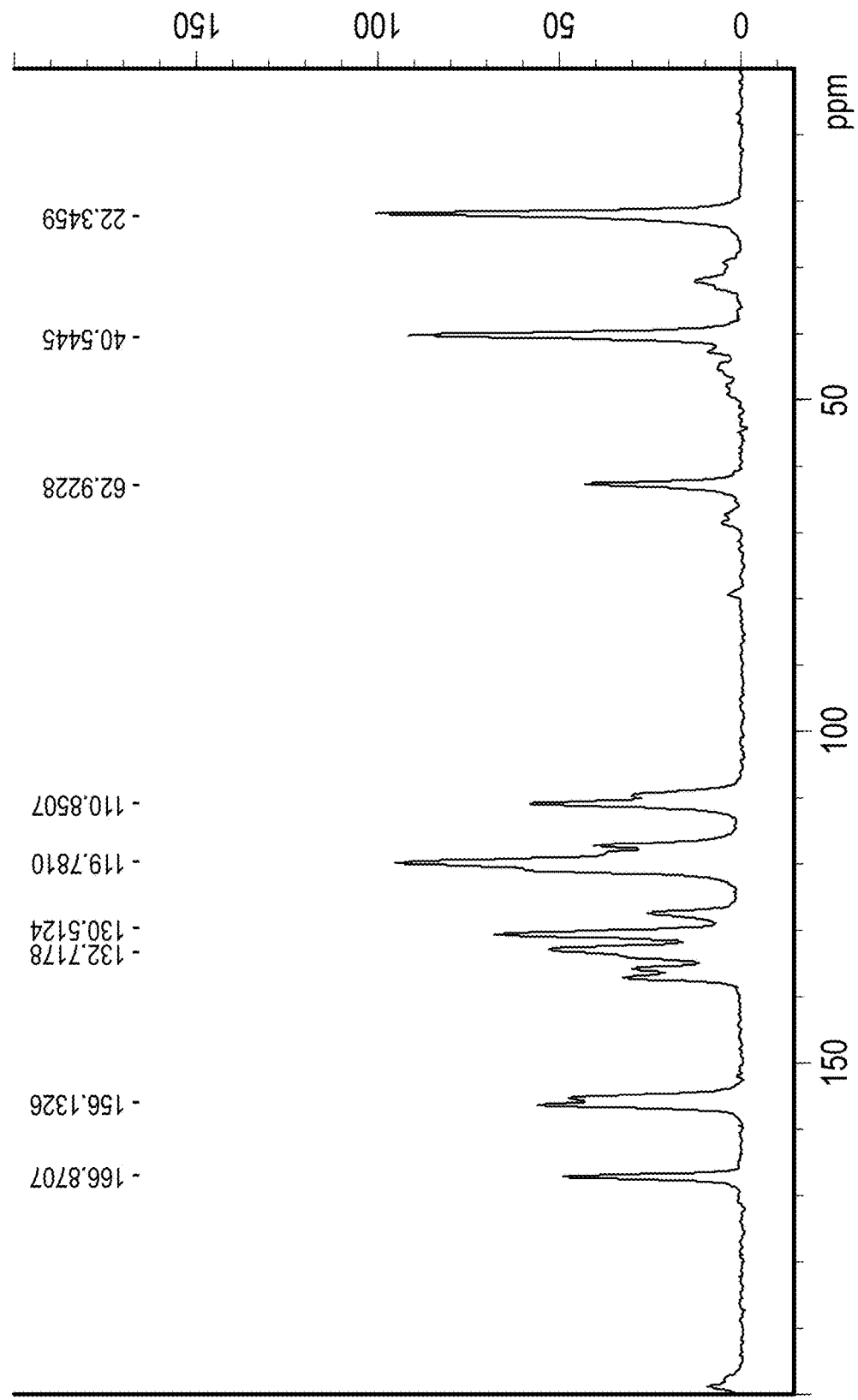
FIG. 19 shows a characteristic solid state $^{13}$C NMR spectrum of Form M2 of Belumosudil Mesylate (full range 200-0 ppm).
Figure 20:
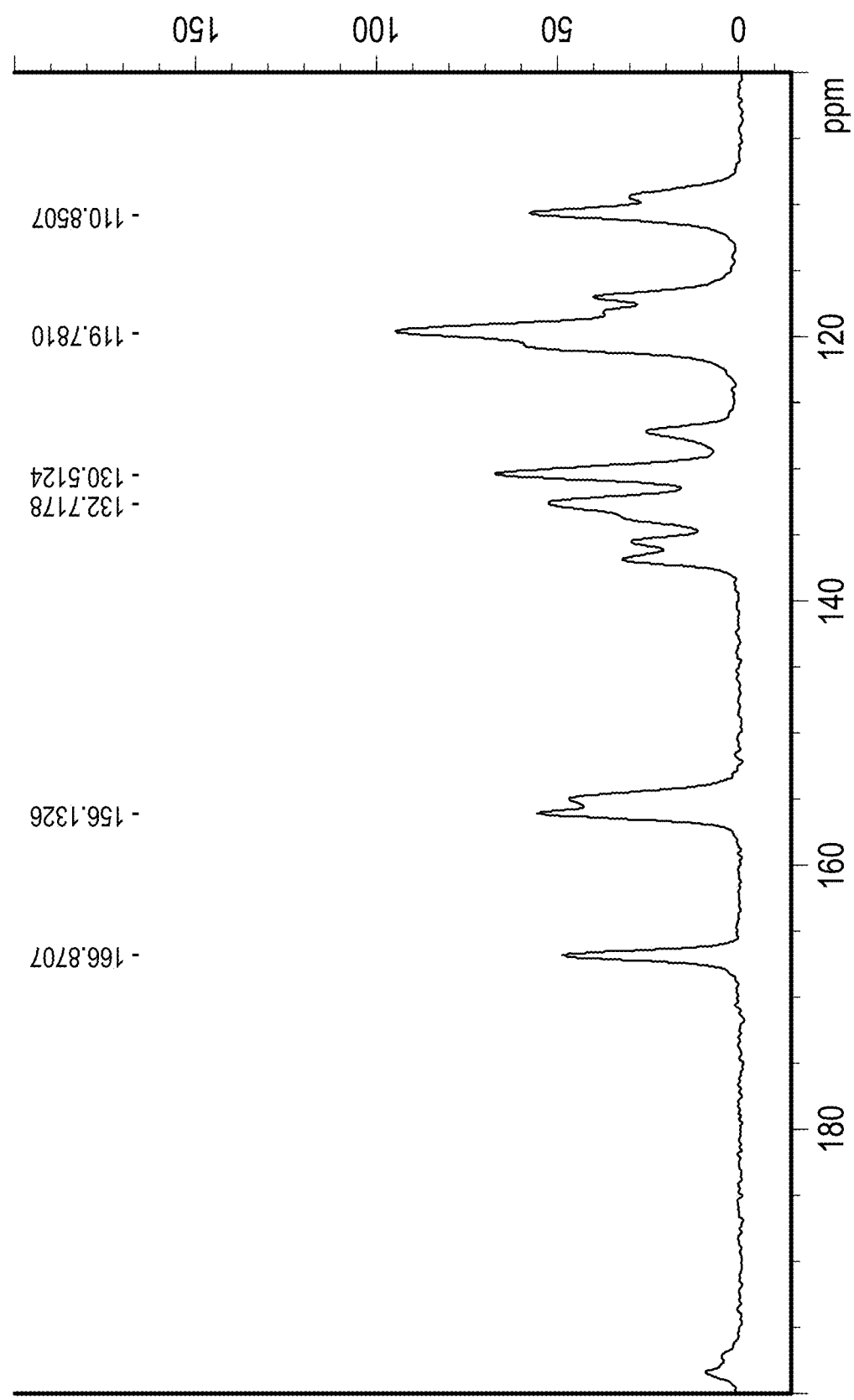
FIG. 20 shows a characteristic solid state $^{13}$C NMR spectrum of Form M2 of Belumosudil Mesylate 200-100 ppm).
Figure 21:
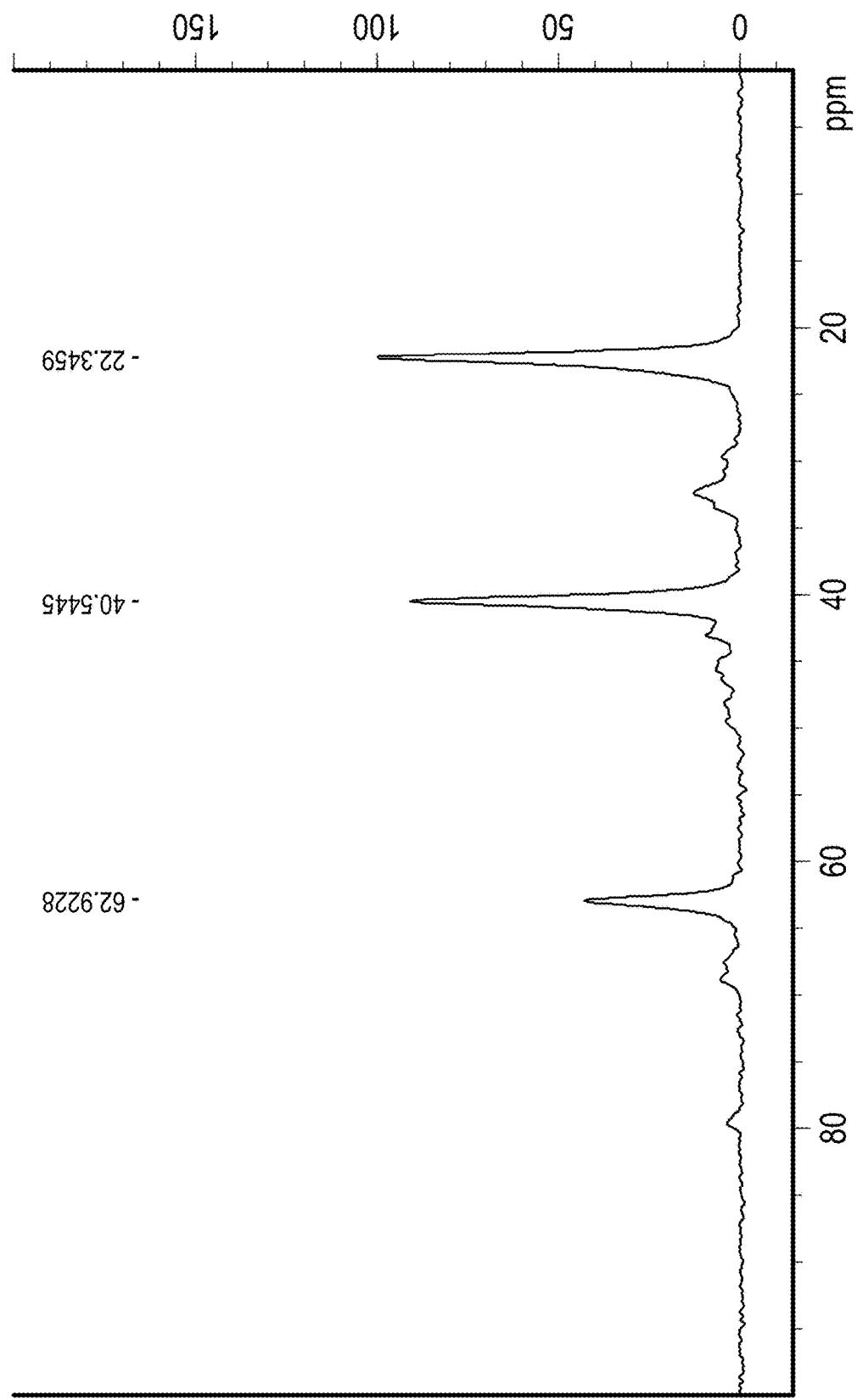
FIG. 21 shows a characteristic solid state $^{13}$C NMR spectrum of Form M2 of Belumosudil Mesylate (100-0 ppm).

The present disclosure includes a crystalline polymorph of Belumosudil Mesylate, designated form M2. The crystalline Form M2 of Belumosudil Mesylate may be characterized by data selected from one or more of the following: an X-ray powder diffraction pattern substantially as depicted in FIG. 7; an X-ray powder diffraction pattern having peaks at 6.3, 12.8, 15.8, 19.3 and 26.5 degrees 2-theta±0.2 degrees 2-theta; a solid state $^{13}$C NMR spectrum with characteristic peaks at 156.1, 132.7, 135.5, 119.8 and 110.9 ppm±0.2 ppm; a solid state $^{13}$C NMR spectrum having the following chemical shift absolute differences from reference peak at 166.9 ppm±1 ppm: 10.8, 34.2, 36.4, 47.1 and 56.0 ppm±0.1 ppm; a solid state $^{13}$C NMR spectrum substantially as depicted in any of FIGS. 19, 20 and 21; and combinations of these data.

Crystalline Form M2 of Belumosudil Mesylate may be further characterized by an X-ray powder diffraction pattern having peaks at 6.3, 12.8, 15.8, 19.3 and 26.5 degrees 2-theta±0.2 degrees 2-theta, and also having any one, two, three, four or five additional peaks selected from 7.8, 20.4, 23.7, 25.1 and 27.4 degrees 2-theta±0.2 degrees 2-theta.

Crystalline form M2 of Belumosudil Mesylate may be alternatively characterized by X-ray powder diffraction pattern having peaks at 6.3, 7.8, 12.8, 15.8, 19.3, 20.4, 23.7, 25.1, 26.5 and 27.4 degrees 2-theta±0.2 degrees 2-theta.

According to any aspect or embodiment of the disclosure, crystalline form M2 of Belumosudil Mesylate may be a hydrate, preferably a di-hydrate. Alternatively, according to any aspect or embodiment of the present disclosure, crystalline form M2 of Belumosudil Mesylate may contain about 1% to about 7% of water, preferably about 1.5 to about 6.1% of water by weight.

In one embodiment of the present disclosure, crystalline Form M2 of Belumosudil Mesylate is isolated. Particularly, crystalline form M2 of Belumosudil Mesylate according to any aspect or embodiment of the disclosure may be isolated.

According to any aspect or embodiment of the present disclosure, crystalline Form M2 of Belumosudil Mesylate is non-hygroscopic. Particularly, Form M2 of Belumosudil Mesylate according to any aspect or embodiment is polymorphically stable at up to 100% relative humidity at room temperature for at least 7 days.

Crystalline Form M2 of Belumosudil Mesylate may be characterized by each of the above characteristics alone/or by all possible combinations, e.g., an XRPD pattern having peaks at 6.3, 12.8, 15.8, 19.3 and 26.5 degrees 2-theta±0.2 degrees 2-theta; an XRPD pattern as depicted in FIG. 7, and combinations thereof.

Crystalline form M2 of Belumosudil Mesylate may be prepared by crystallisation from a mixture comprising Belumosudil Mesylate and water, and optionally one or more polar organic solvents, preferably alcohols or mixtures thereof. Examples of suitable solvents include but are not limited to methanol, isopropanol, 1-propanol, n-butanol. The water may be present in an amount of: about 1 to about 60 ml per mmol of Belumosudil. In any embodiment, the process comprises:

(a) providing a mixture of Belumosudil Mesylate in water and optionally one or more polar organic solvents, optionally with heating,
(b) optionally stirring the mixture, optionally at elevated temperature;
(c) optionally cooling the mixture;
(d) optionally stirring the cooled mixture; and
(e) optionally isolating crystalline form M2 of Belumosudil Mesylate from the mixture.

In any of the embodiments of the process, the mixture in step (a) may be prepared by:

(i) providing a mixture of Belumosudil free base in water or a mixture of water and at least one polar organic solvent;
(ii) combining the mixture with Methanesulfonic acid; and
(iii) optionally heating the mixture.

According to any embodiment of the process for preparing Form M2 of Belumosudil Mesylate, the polar organic solvent in step (i) may preferably comprise an alcohol or mixtures thereof. Preferably the polar organic solvent in step (i) is selected from: methanol, isopropanol, 1-propanol and n-butanol, or mixtures thereof; more preferably the polar organic solvent in step (i) is methanol, ethanol, isopropanol, 1-propanol, or n-butanol, and most preferably ethanol.

According to any embodiment of the process for preparing Form M2 of Belumosudil Mesylate, the ratio of solvent to Belumosudil in step (i) may be: about 10 to about 40 ml per gram of Belumosudil, about 14 to about 35 ml per gram of Belumosudil or about 16 to about 28 ml per gram of Belumosudil, or about 18 to about 24 ml per gram of Belumosudil, and optionally about 20 ml per gram of Belumosudil. The mixture in step (i) may be a solution or a slurry.

According to any embodiment of the process for preparing Form M2 of Belumosudil Mesylate, in step (ii), the combining of Methanesulfonic acid to Belumosudil may be in any order. Preferably, methanesulfonic acid may be added to the mixture of Belumosudil in the solvent. The addition may be carried out portion-wise or dropwise. The Methanesulfonic acid is optionally added in an amount of: about 0.7 to about 1.5 molar equivalents, about 0.9 to about 1.3 molar equivalents, about 1.0 to about 1.2 molar equivalents, or about 1.1 molar equivalents relative to Belumosudil. Preferably, step (ii) comprises adding Methanesulfonic acid, to the mixture of Belumosudil and solvent.

In step (iii) of the process for preparing Belumosudil Form M2, the mixture may be optionally heated. The heating may be to a temperature of about 30° C. to about 70° C., about 40° C. to about 60° C., about 45° C. to about 55° C., or about 50° C. The heating may take place over any suitable period of time to form a solution of Belumosudil Mesylate.

Alternatively, in the process for preparing Belumosudil Form M2 according to any aspect or embodiment of the invention, the mixture in step (a) may be prepared by a process comprising:

(i-b) combining Belumosudil Mesylate with a polar organic solvent, optionally with heating to produce a solution; and
(ii-b) adding water as antisolvent.

According to any embodiment of the process for preparing Form M2 of Belumosudil Mesylate. The polar organic solvent in step (i-b) is preferably selected from the group consisting of TFE, DMSO and or mixtures thereof. Particularly, the solvent is selected from the group consisting of TFE and DMSO. The ratio of polar organic solvent in step (i-b) is preferably about 5 ml to 60 ml, about 7 ml to about 50 ml, about 10 ml to about 45 ml, or about 10 ml to about 40 ml, per gram of Belumosudil Mesylate.

Alternatively, in the process for preparing Belumosudil Form M2 according to any aspect or embodiment of the invention, the mixture in step (a) may be prepared by a process comprising: (i-c) combining Belumosudil Mesylate with water to produce a slurry. Preferably, the Belumosudil Mesylate is Form M1 as described according to any aspect or embodiment herein. Preferably, the ratio of water step (i-c) is preferably about 10 ml to 60 ml, about 20 ml to about 50 ml, about 30 ml to about 45 ml, or about 40 ml, per gram of Belumosudil Mesylate.

In any embodiment of the process, step (b) is carried out. Step (b) is preferably carried out under heating, preferably at a temperature of: about 30° C. to about 80° C., about 40° C. to about 75° C., about 45° C. to about 70° C., about 45° C. to about 65° C., about 45° C. to about 65° C., about 48° C. to about 62° C., or about 50° C. to about 60° C. The stirring may be carried out for any suitable period of time.

In any embodiment of the process for preparing Form M2, step (c) is carried out. Step (c) preferably comprises cooling the mixture to room temperature.

In any embodiment of the process for preparing Form M2, step (d) may be carried out. The stirring may be for any suitable time to prepare Form M2.

In any embodiment of the process for preparing crystalline Belumosudil Mesylate Form M2, step (e) may be carried out by any suitable method, for example by filtration, decantation or by centrifuge. Preferably the isolation of the solid is by filtration or by centrifuge, and more preferably by centrifuge.

In any embodiment the process may further comprise washing and/or drying steps.

Figure 8:
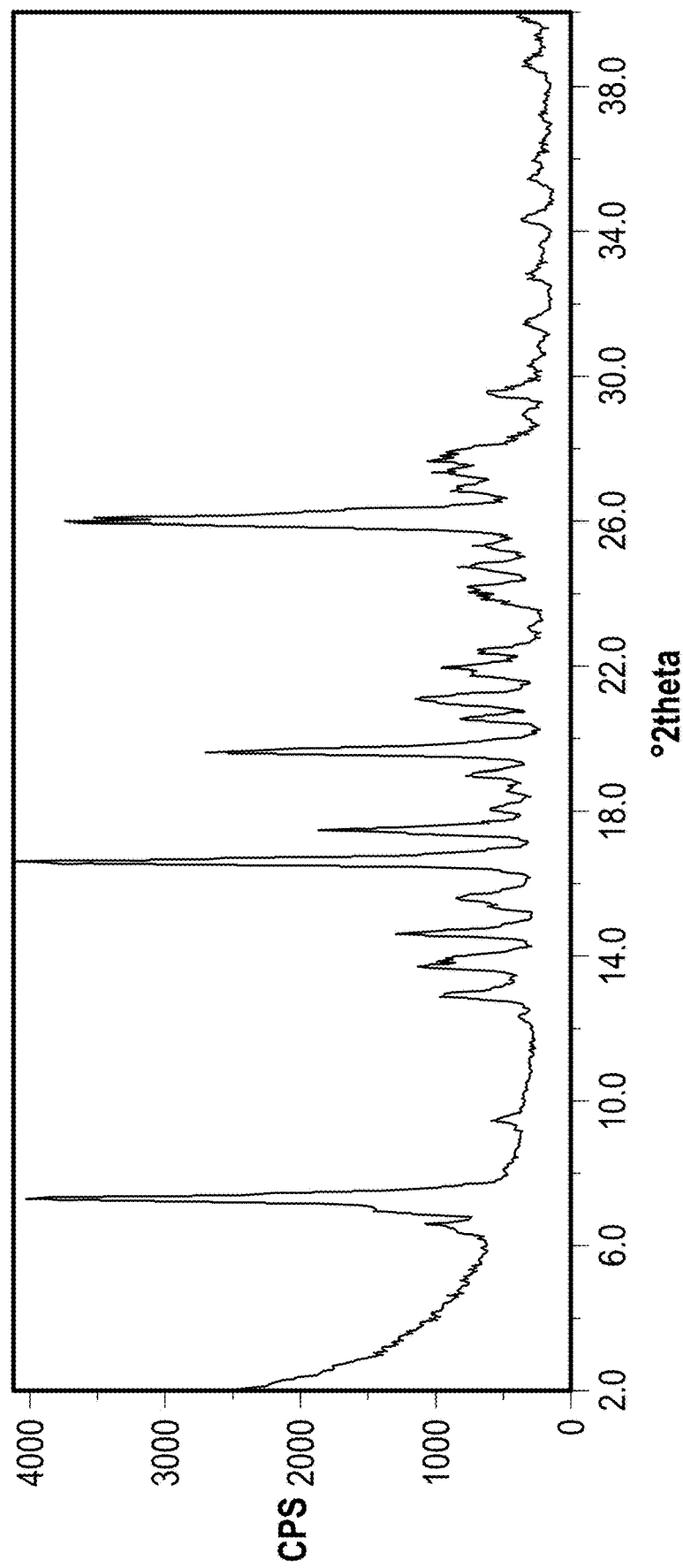
FIG. 8 shows a characteristic X-ray powder diffraction pattern (XRPD) of Belumosudil Mesylate form M3.

The present disclosure includes a crystalline polymorph of Belumosudil Mesylate, designated form M3. The crystalline Form M3 of Belumosudil Mesylate may be characterized by data selected from one or more of the following: an X-ray powder diffraction pattern substantially as depicted in FIG. 8; an X-ray powder diffraction pattern having peaks at 7.3, 14.6, 16.6, 17.5 and 19.6 degrees 2-theta±0.2 degrees 2-theta; and combinations of these data.

Crystalline Form M3 of Belumosudil Mesylate may be further characterized by an X-ray powder diffraction pattern having peaks at 7.3, 14.6, 16.6, 17.5 and 19.6 degrees 2-theta±0.2 degrees 2-theta, and also having any one, two, three, four or five additional peaks selected from 12.9, 13.7, 19.0, 20.6 and 26.0 degrees 2-theta±0.2 degrees 2-theta.

Crystalline form M3 of Belumosudil Mesylate may be alternatively characterized by X-ray powder diffraction pattern having peaks at 7.3, 12.9, 13.7, 14.6, 16.6, 17.5, 19.0, 19.6, 20.6 and 26.0 degrees 2-theta±0.2 degrees 2-theta.

In one embodiment of the present disclosure, crystalline Form M3 of Belumosudil Mesylate is isolated.

Crystalline Form M3 of Belumosudil Mesylate may be characterized by each of the above characteristics alone/or by all possible combinations, e.g., an XRPD pattern having peaks at 7.3, 14.6, 16.6, 17.5 and 19.6 degrees 2-theta±0.2 degrees 2-theta; an XRPD pattern as depicted in FIG. 8, and combinations thereof.

Figure 11:
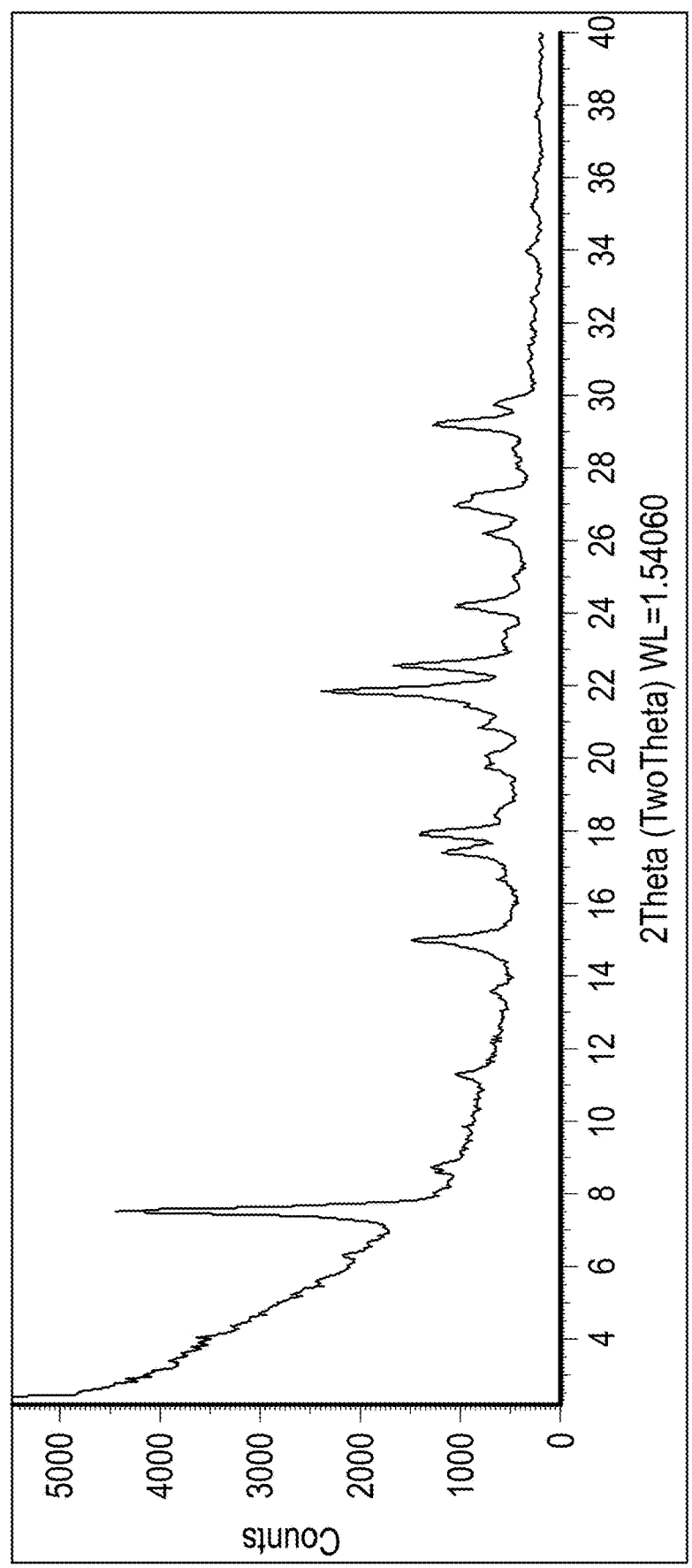
FIG. 11 shows a characteristic X-ray powder diffraction pattern (XRPD) of Belumosudil Mesylate form M4.

The present disclosure includes a crystalline polymorph of Belumosudil Mesylate, designated form M4. The crystalline Form M4 of Belumosudil Mesylate may be characterized by data selected from one or more of the following: an X-ray powder diffraction pattern substantially as depicted in FIG. 11; an X-ray powder diffraction pattern having peaks at 7.5, 15.0, 17.9, 21.8 and 22.6 degrees 2-theta±0.2 degrees 2-theta; and combinations of these data.

Crystalline Form M4 of Belumosudil Mesylate may be further characterized by an X-ray powder diffraction pattern having peaks at 7.5, 15.0, 17.9, 21.8 and 22.6 degrees 2-theta±0.2 degrees 2-theta, and also having any one, two, three, four or five additional peaks selected from 11.3, 17.4, 20.9, 24.2 and 29.2 degrees 2-theta±0.2 degrees 2-theta.

Crystalline form M4 of Belumosudil Mesylate may be alternatively characterized by X-ray powder diffraction pattern having peaks at 7.5, 11.3, 15.0, 17.4, 17.9, 20.9, 21.8, 22.6, 24.2 and 29.2 degrees 2-theta±0.2 degrees 2-theta.

In one embodiment of the present disclosure, crystalline Form M4 of Belumosudil Mesylate is isolated.

Crystalline Form M4 of Belumosudil Mesylate may be characterized by each of the above characteristics alone/or by all possible combinations, e.g., an XRPD pattern having peaks at 7.5, 15.0, 17.9, 21.8 and 22.6 degrees 2-theta±0.2 degrees 2-theta; an XRPD pattern as depicted in FIG. 11, and combinations thereof.

Figure 12:
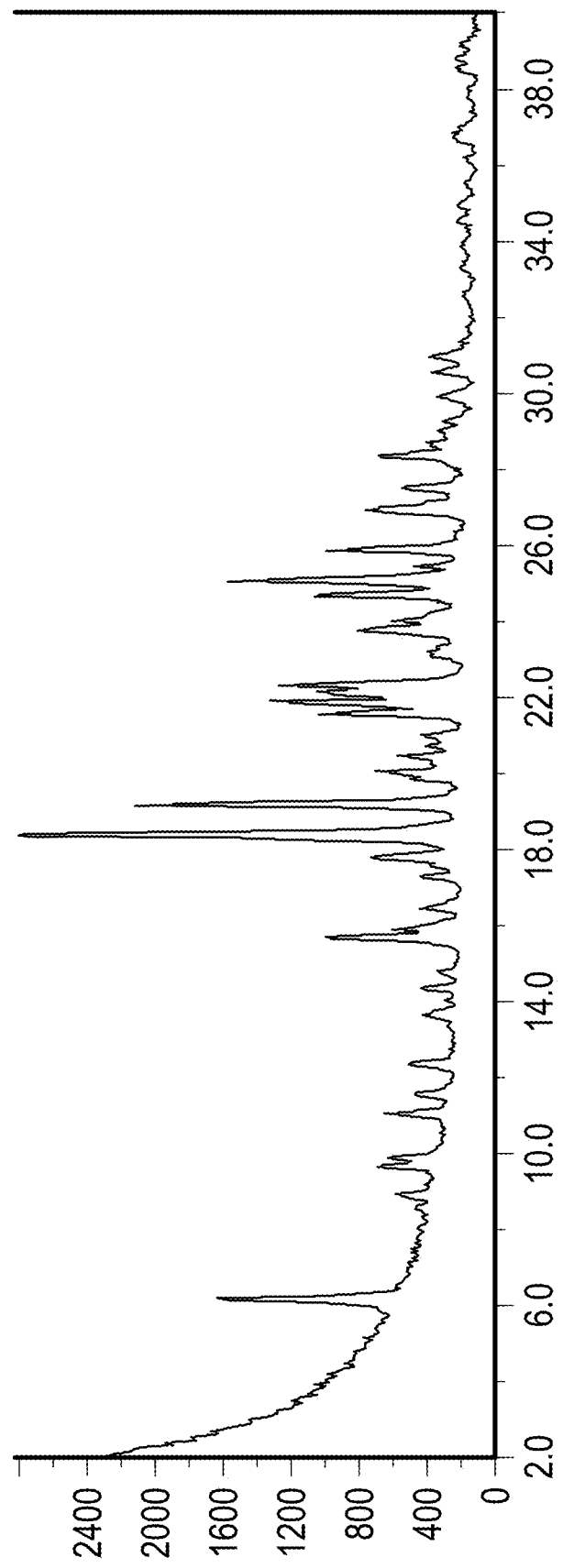
FIG. 12 shows a characteristic X-ray powder diffraction pattern (XRPD) of Belumosudil Mesylate form M5.

The present disclosure includes a crystalline polymorph of Belumosudil Mesylate, designated form M5. The crystalline Form M5 of Belumosudil Mesylate may be characterized by data selected from one or more of the following: an X-ray powder diffraction pattern substantially as depicted in FIG. 12; an X-ray powder diffraction pattern having peaks at 6.2, 15.7, 18.4, 19.2 and 25.1 degrees 2-theta±0.2 degrees 2-theta; and combinations of these data.

Crystalline Form M5 of Belumosudil Mesylate may be further characterized by an X-ray powder diffraction pattern having peaks at 6.2, 15.7, 18.4, 19.2 and 25.1 degrees 2-theta±0.2 degrees 2-theta, and also having any one, two, three, four or five additional peaks selected from 17.8, 21.6, 21.9, 24.7, 25.9 degrees 2-theta±0.2 degrees 2-theta.

Crystalline form M5 of Belumosudil Mesylate may be alternatively characterized by X-ray powder diffraction pattern having peaks at 6.2, 15.7, 17.8, 18.4, 19.2, 21.6, 21.9, 24.7, 25.1 and 25.9 degrees 2-theta±0.2 degrees 2-theta.

In one embodiment of the present disclosure, crystalline Form M5 of Belumosudil Mesylate is isolated.

Crystalline Form M5 of Belumosudil Mesylate may be characterized by each of the above characteristics alone/or by all possible combinations, e.g., an XRPD pattern having peaks at 6.2, 15.7, 18.4, 19.2 and 25.1 degrees 2-theta±0.2 degrees 2-theta; an XRPD pattern as depicted in FIG. 12, and combinations thereof.

Figure 13:
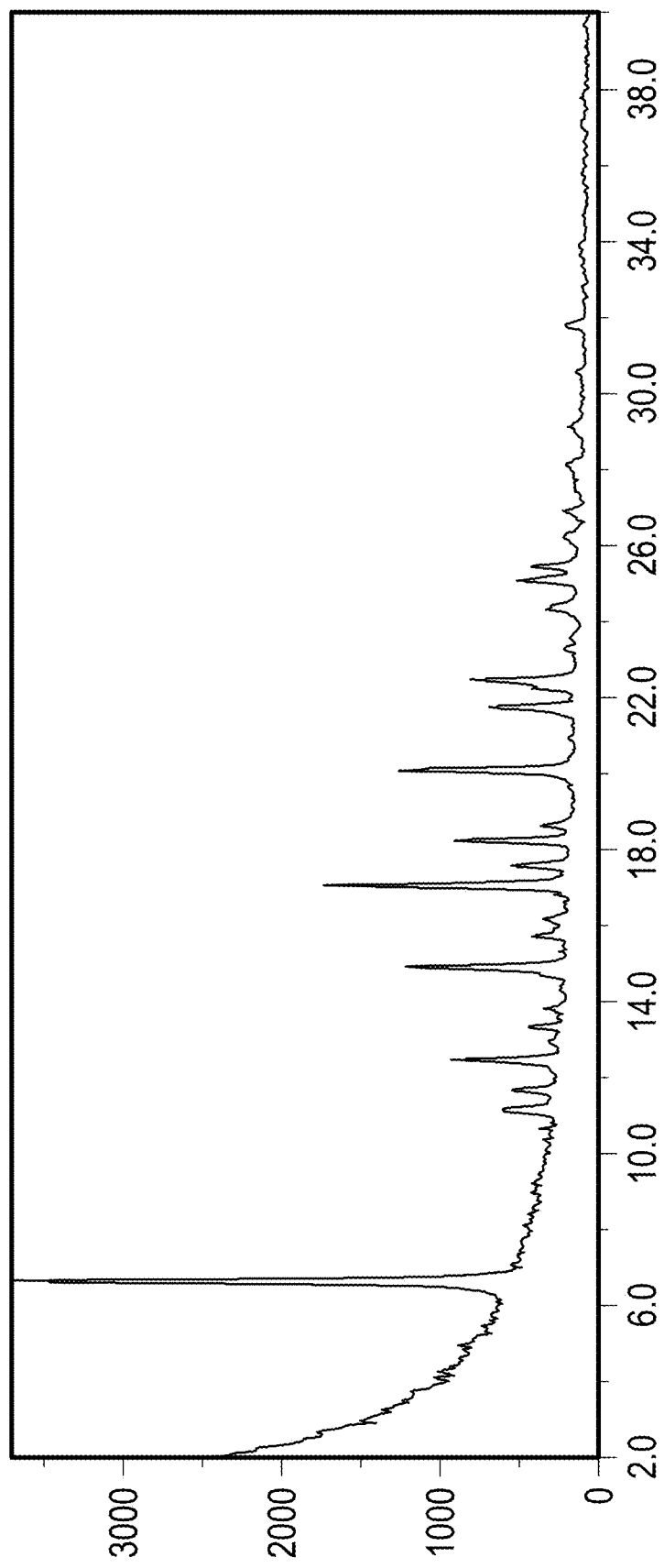
FIG. 13 shows a characteristic X-ray powder diffraction pattern (XRPD) of Belumosudil Besylate form BS1.
Figure 22:
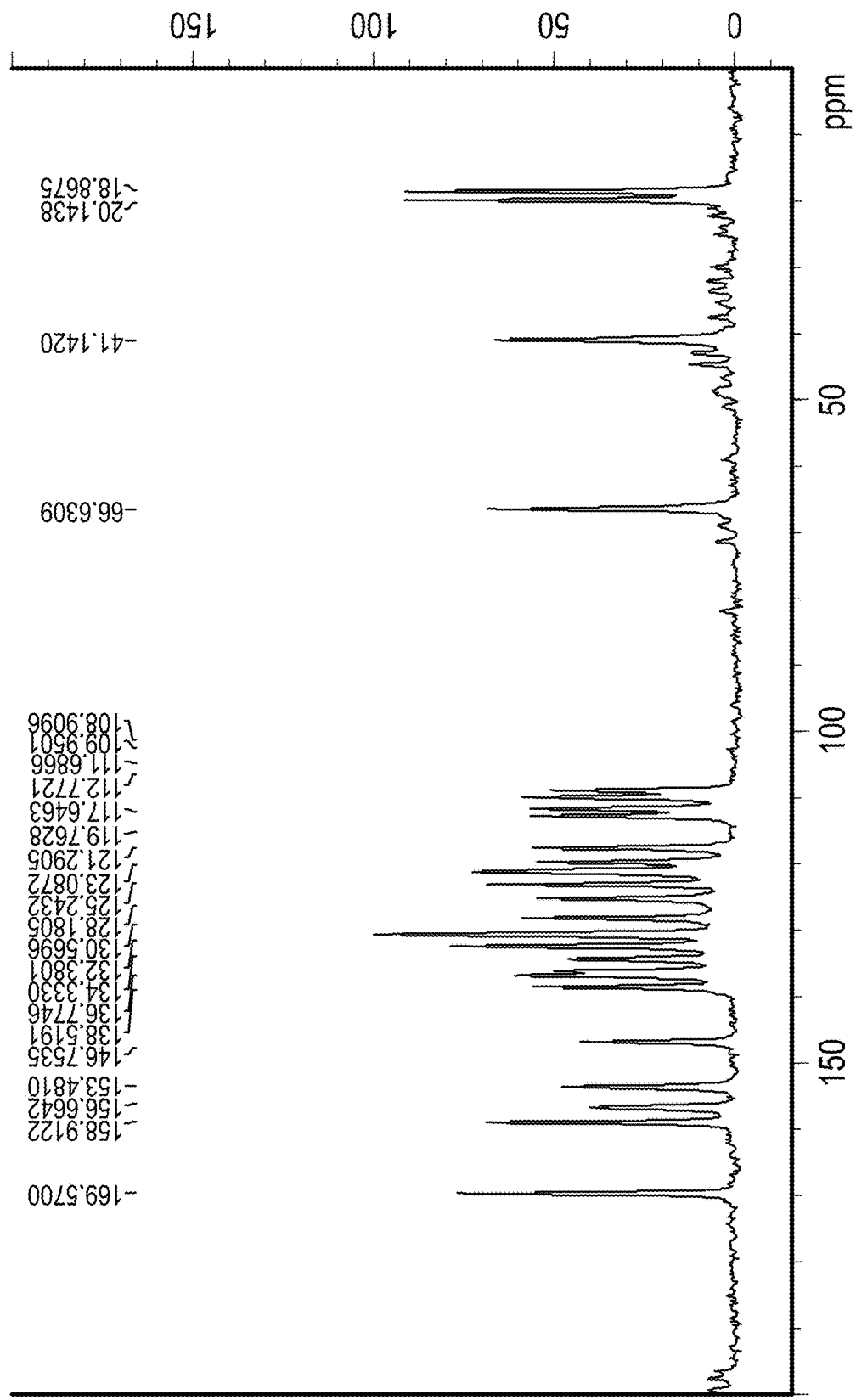
FIG. 22 shows a characteristic solid state $^{13}$C NMR spectrum of Form BS1 of Belumosudil Besylate (full range 200-0 ppm).
Figure 23:
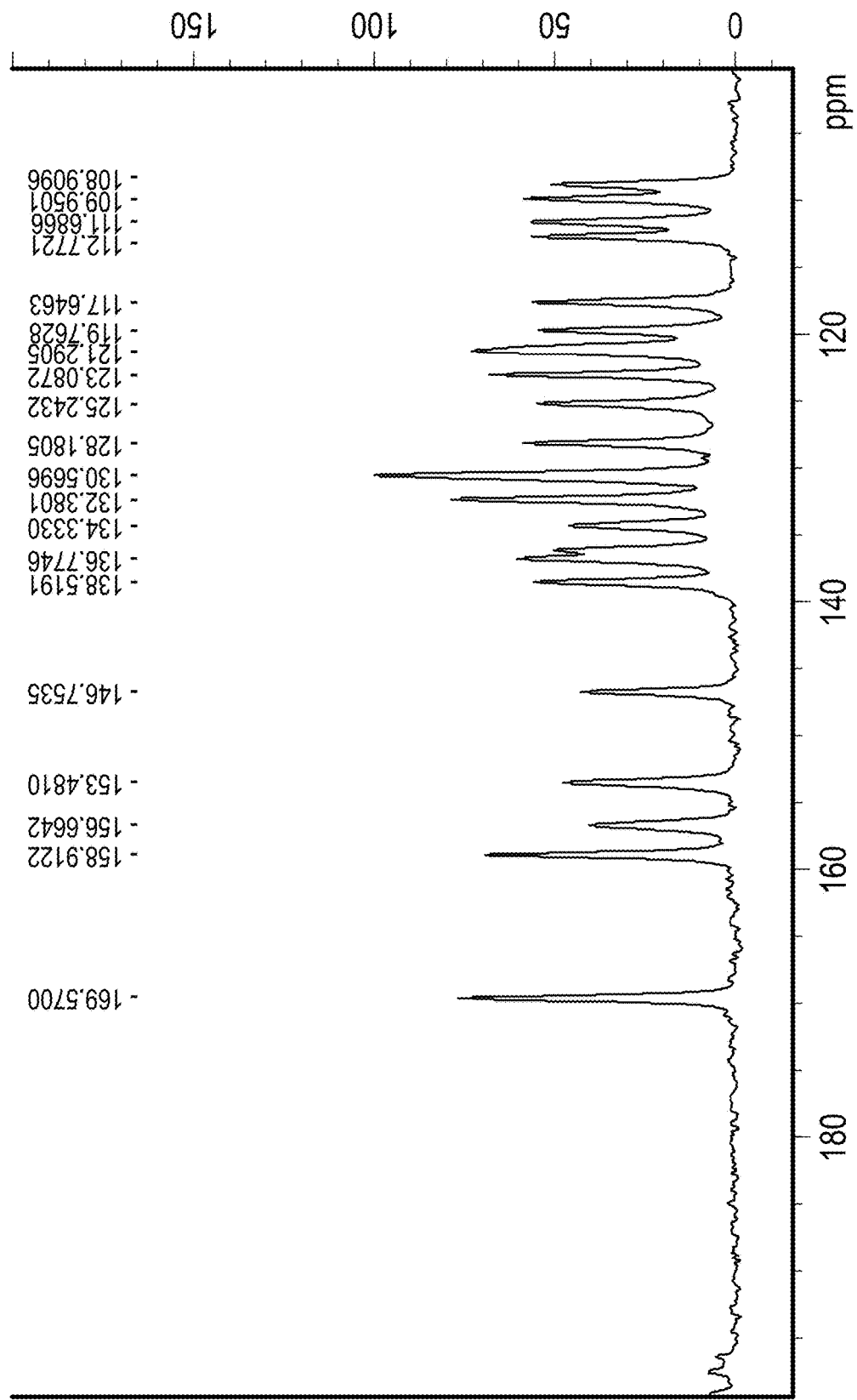
FIG. 23 shows a characteristic solid state $^{13}$C NMR spectrum of Form BS1 of Belumosudil Besylate 200-100 ppm).
Figure 24:
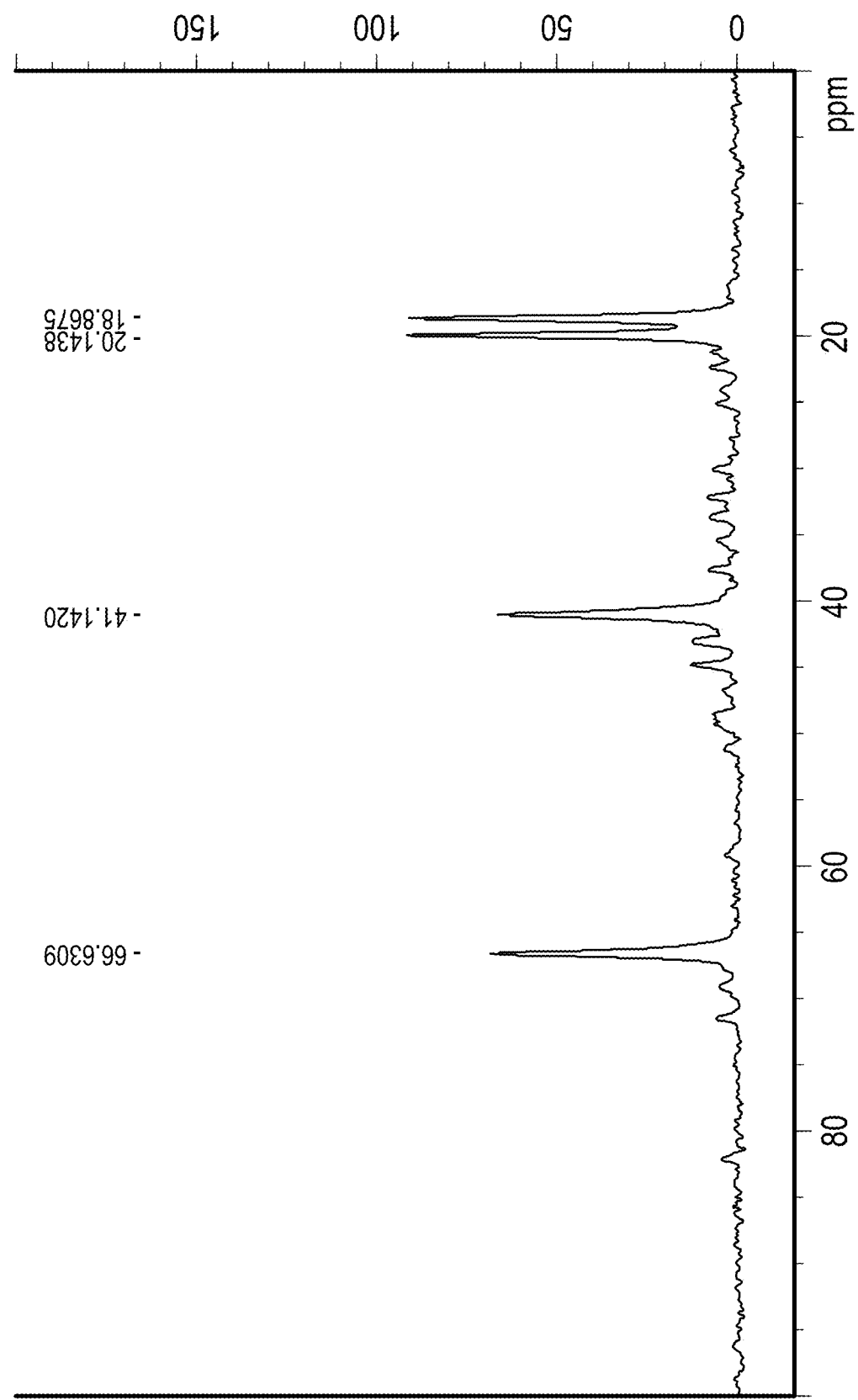
FIG. 24 shows a characteristic solid state $^{13}$C NMR spectrum of Form BS1 of Belumosudil Besylate (100-0 ppm).
Figure 25:
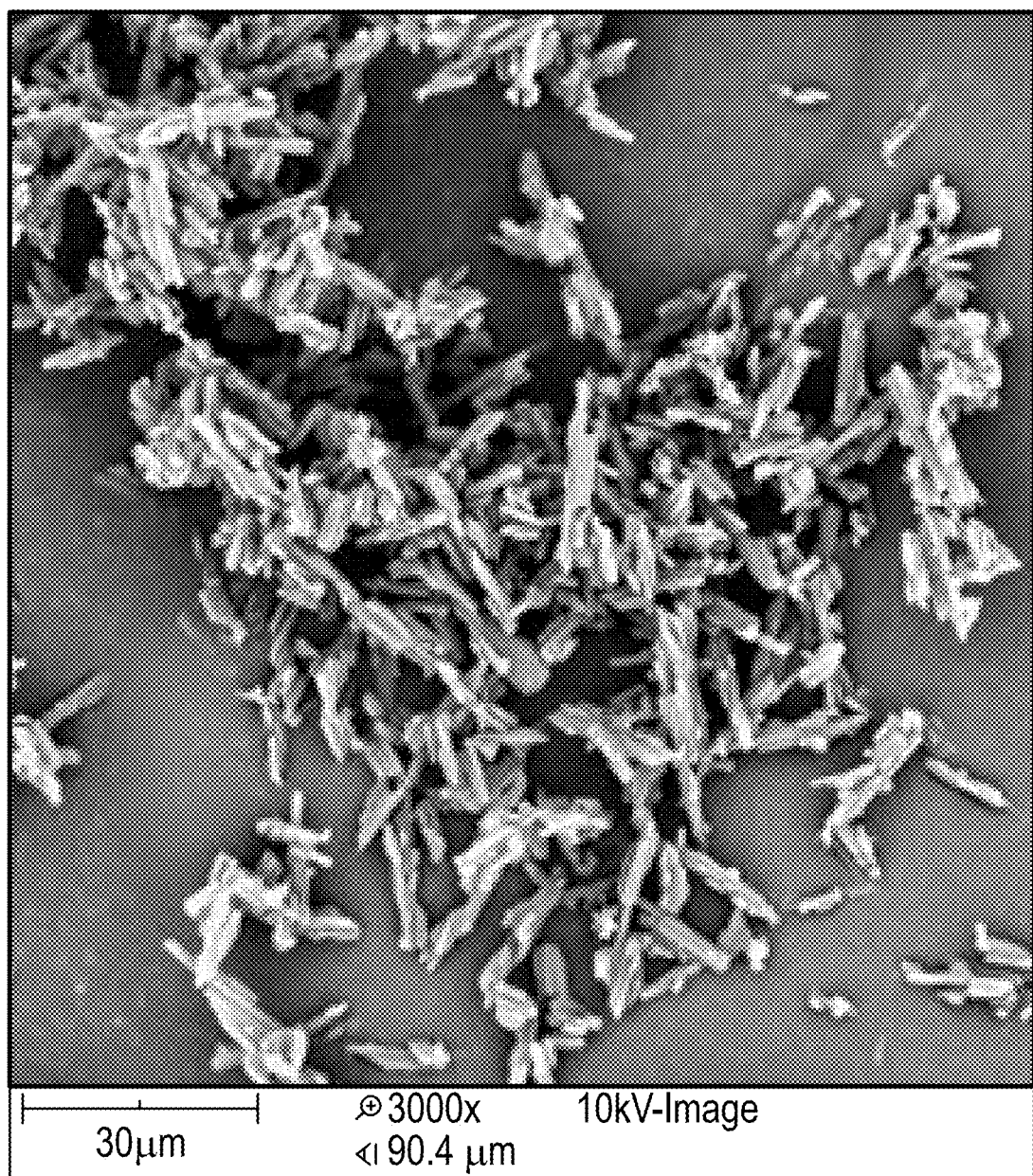
FIG. 25 shows a scanning electron microscopy (SEM) image of particles of Form BS1 of Belumosudil Besylate.

The present disclosure includes a crystalline polymorph of Belumosudil Besylate, designated form BS1. The crystalline Form BS1 of Belumosudil Besylate may be characterized by data selected from one or more of the following: an X-ray powder diffraction pattern substantially as depicted in FIG. 13; an X-ray powder diffraction pattern having peaks at 6.6, 12.5, 14.9, 17.0 and 20.1 degrees 2-theta±0.2 degrees 2-theta; a solid state $^{13}$C NMR spectrum with characteristic peaks at 158.9, 146.8, 134.3, 121.3 and 117.6 ppm±0.2 ppm; a solid state $^{13}$C NMR spectrum having the following chemical shift absolute differences from reference peak at 169.6 ppm±1 ppm: 10.7, 22.8, 35.3, 48.3 and 52.0 ppm±0.1 ppm; a solid state $^{13}$C NMR spectrum substantially as depicted in any of FIGS. 22, 23 and 24 and combinations of these data.

Crystalline Form BS1 of Belumosudil Besylate may be further characterized by an X-ray powder diffraction pattern having peaks at 6.6, 12.5, 14.9, 17.0 and 20.1 degrees 2-theta±0.2 degrees 2-theta, and also having any one, two, three, four or five additional peaks selected from 11.6, 17.6, 18.2, 21.7 and 25.1 degrees 2-theta±0.2 degrees 2-theta.

Crystalline form BS1 of Belumosudil Besylate may be alternatively characterized by X-ray powder diffraction pattern having peaks at 6.6, 11.6, 12.5, 14.9, 17.0, 17.6, 18.2, 20.1, 21.7 and 25.1 degrees 2-theta±0.2 degrees 2-theta.

Crystalline form BS1 of Belumosudil Besylate may be an anhydrous form, as can be determined by TGA. In certain embodiment, the present disclosure comprises crystalline form BS1 of Belumosudil Besylate having 0.5% w/w or less, or 0.2% w/w or less, or 0.1 wt % or less, of total residual solvent. According to any aspect or embodiment as described herein, crystalline form BS1 of Belumosudil Besylate may contain 0.5% w/w or less, or 0.2% w/w or less, or 0.1 wt % or less, of total residual solvent. The residual organic solvent may be one or more polar solvents, preferably water, alcohols (particularly $C_{1-4}$ alcohols, especially ethanol, methanol, isopropanol, 1-propanol, or n-butanol), and most preferably the residual organic solvent may be ethanol. Particularly, crystalline form BS1 of Belumosudil Besylate according to any aspect or embodiment of the disclosure may contain 0.5% w/w or less, or 0.2 w/w or less, or 0.1 wt % or less, of ethanol.

In one embodiment of the present disclosure, crystalline Form BS1 of Belumosudil Besylate is isolated. Particularly, crystalline form BS1 of Belumosudil Besylate according to any aspect or embodiment of the disclosure may be isolated.

In any aspect or embodiment of the present disclosure, crystalline Form BS1 of Belumosudil Mesylate is non-hygroscopic. Particularly, Form BS1 of Belumosudil Mesylate according to any aspect or embodiment is polymorphically stable at up to 100% relative humidity at room temperature for at least 7 days.

Crystalline Form BS1 of Belumosudil Besylate may be characterized by each of the above characteristics alone/or by all possible combinations, e.g., an XRPD pattern having peaks at 6.6, 12.5, 14.9, 17.0 and 20.1 degrees 2-theta±0.2 degrees 2-theta; an XRPD pattern as depicted in FIG. 13, and combinations thereof.

Crystalline form BS1 of Belumosudil Besylate may be prepared by crystallisation from a mixture comprising Belumosudil Besylate and a polar solvent such as ethanol. In any aspect or embodiment, the process comprises:
 (a) providing a mixture of Belumosudil Besylate in one or more polar solvents;
 (b) optionally stirring the mixture, optionally at elevated temperature;
 (c) optionally cooling the mixture; and
 (d) optionally isolating crystalline form BS1 of Belumosudil Besylate from the mixture.

In any of the embodiments of the process for preparing Form BS1, the mixture in step (a) may be prepared by:
 (i) providing a mixture of Belumosudil free base (preferably Form B1 as described herein) in a polar solvent; and
 (ii) combining the mixture with Benzenesulfonic acid.

In any of the embodiment of the process for preparing Form BS1, the polar solvent in step (i) is preferably an alcohol (particularly $C_{1-4}$ alcohols, especially ethanol, methanol, isopropanol, 1-propanol, or n-butanol). Preferably the polar solvent comprises ethanol or isopropanol and more preferably the polar solvent is ethanol. In step (i), the ratio of solvent to Belumosudil may be: about 10 to about 40 ml per gram of Belumosudil, about 14 to about 35 ml per gram of Belumosudil or about 16 to about 28 ml per gram of Belumosudil, or about 18 to about 24 ml per gram of Belumosudil, and optionally about 20 ml per gram of Belumosudil. The mixture may be a solution or a slurry.

In any aspect or embodiment of the process for preparing Form BS1, step (ii) comprises combining Benzenesulfonic acid to Belumosudil. The combining may be in any order. Preferably, benzenesulfonic acid may be added to the mixture of Belumosudil in the solvent. The addition may be carried out portion-wise or dropwise. The Benzenesulfonic acid is optionally added in an amount of: about 0.7 to about 1.5 molar equivalents, about 0.9 to about 1.3 molar equivalents, about 1.0 to about 1.2 molar equivalents, or about 1.1 molar equivalents relative to Belumosudil. Preferably, step (ii) comprises adding Benzenesulfonic acid to the mixture of Belumosudil and polar solvent.

Alternatively, in any of the embodiments of the process for preparing Form BS1, the mixture in step (a) may be prepared by combining Belumosudil Besylate with a polar solvent. Preferably the polar solvent is an alcohol (particularly $C_{1-4}$ alcohols, especially ethanol, methanol, isopropanol, 1-propanol, or n-butanol), and most preferably the polar solvent is ethanol.

In any embodiment of the process for preparing form BS1, step (b) is carried out, preferably by stirring at room temperature, more preferably at a temperature of: about 30° C. to about 70° C., about 40° C. to about 60° C., about 45° C. to about 55° C., or about 50° C. Preferably, the stirring is carried out at a temperature. The stirring may be carried out for any suitable time to form Belumosudil Besylate Form BS1. Typically, the stirring may be carried out over a period of about 10 minutes to about 2 hours, about 20 minutes to about 1 hour, or about 45 minutes.

In any embodiment of the process for preparing form BS1, step (c) is carried out, preferably wherein the cooling is to room temperature.

In any embodiment of the process for preparing form BS1, step (d) may be carried out by any suitable method, for example by filtration, decantation or by centrifuge. Preferably the isolation of the solid is by filtration or by centrifuge, and more preferably by centrifuge.

In any embodiment the process for preparing from BS1 may further comprise washing and/or drying steps.

Figure 14:
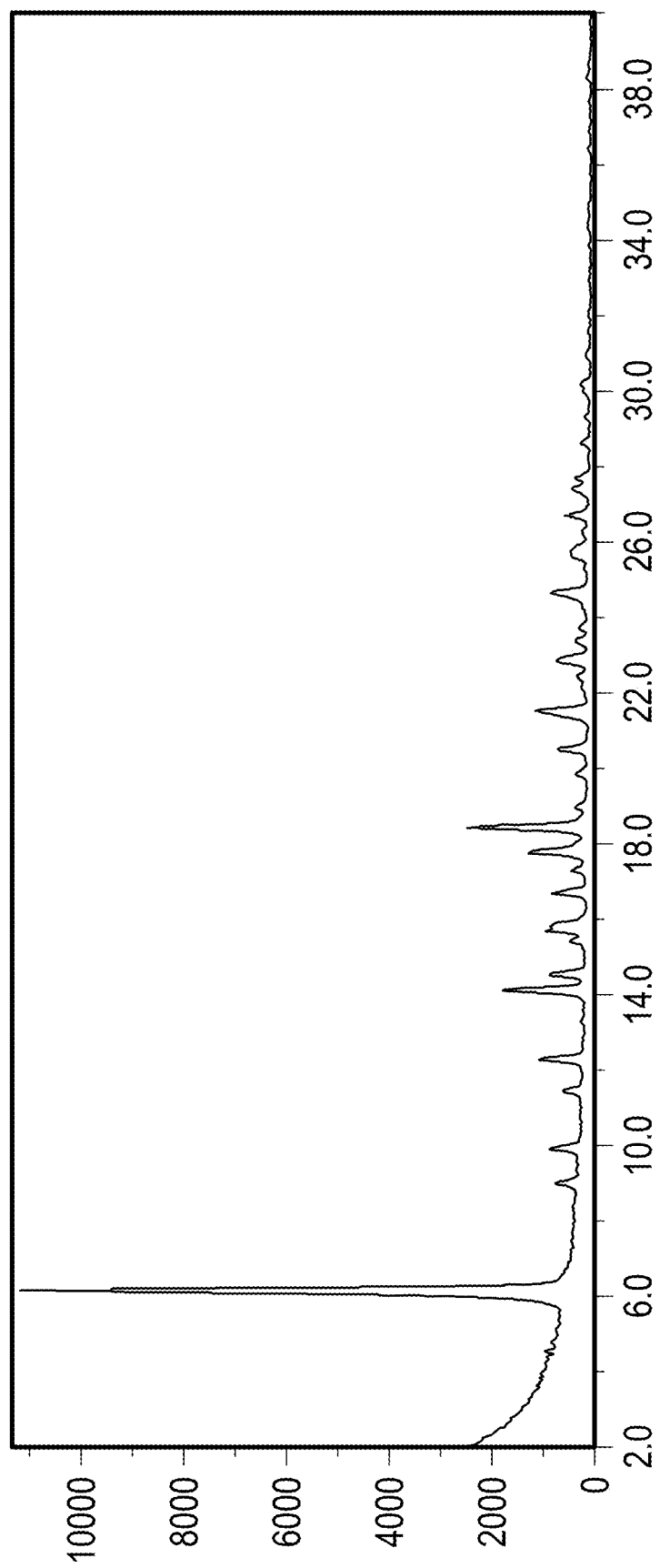
FIG. 14 shows a characteristic X-ray powder diffraction pattern (XRPD) of Belumosudil Tosylate form T1.
Figure 26:
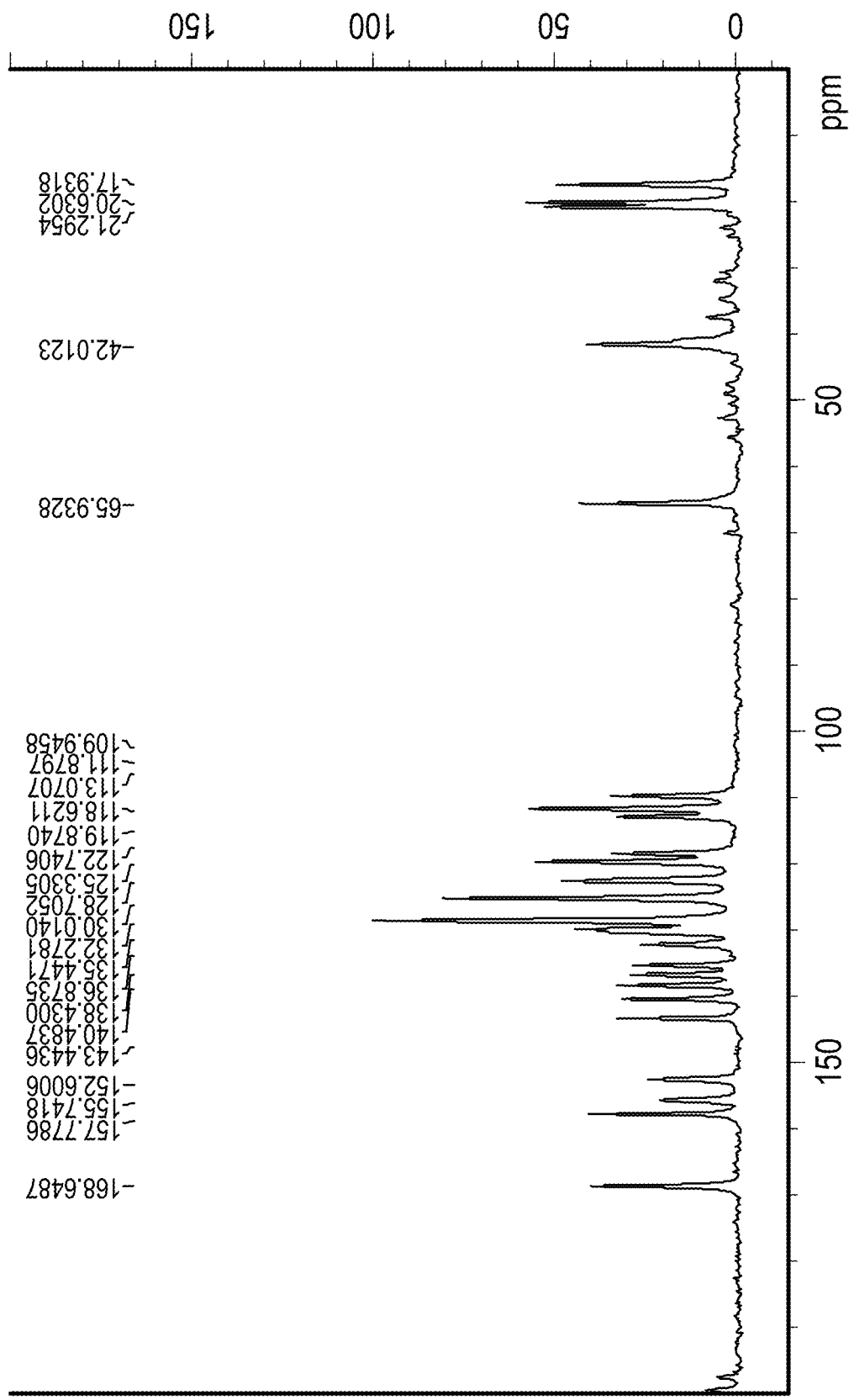
FIG. 26 shows a characteristic solid state $^{13}$C NMR spectrum of Form T1 of Belumosudil Tosylate (full range 200-0 ppm).
Figure 27:
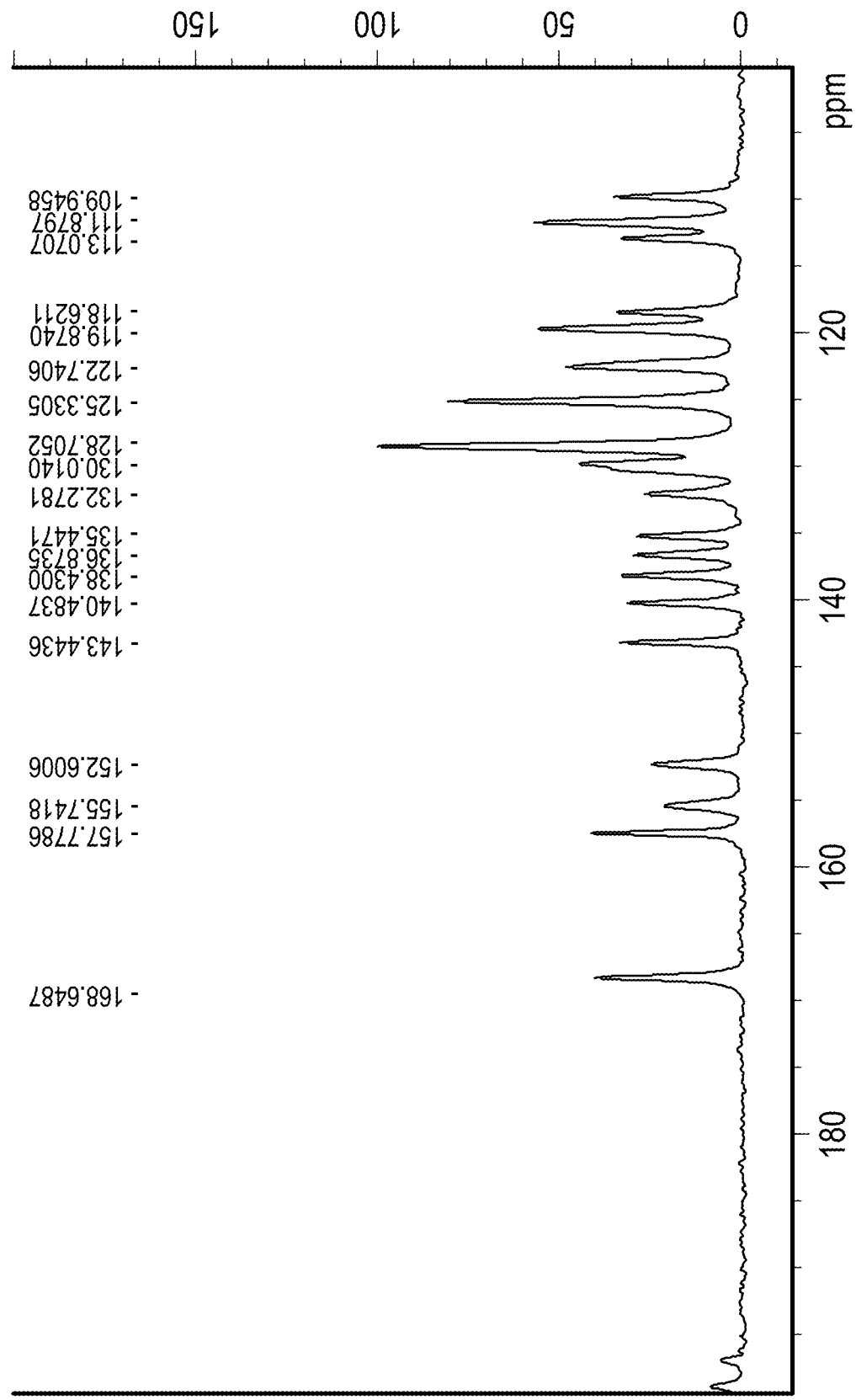
FIG. 27 shows a characteristic solid state $^{13}$C NMR spectrum of Form T1 of Belumosudil Tosylate 200-100 ppm).
Figure 28:
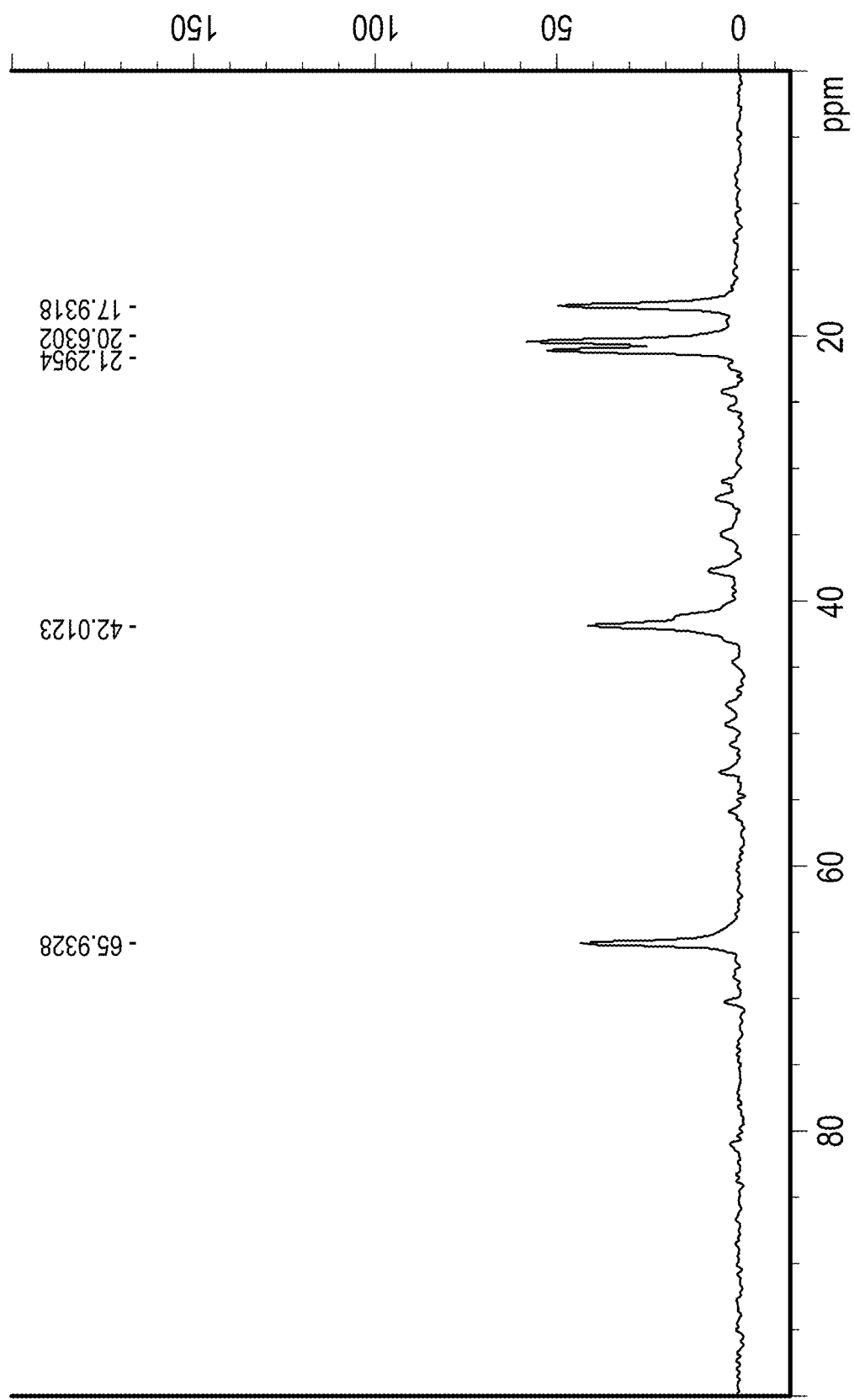
FIG. 28 shows a characteristic solid state $^{13}$C NMR spectrum of Form T1 of Belumosudil Tosylate (100-0 ppm).
Figure 29:
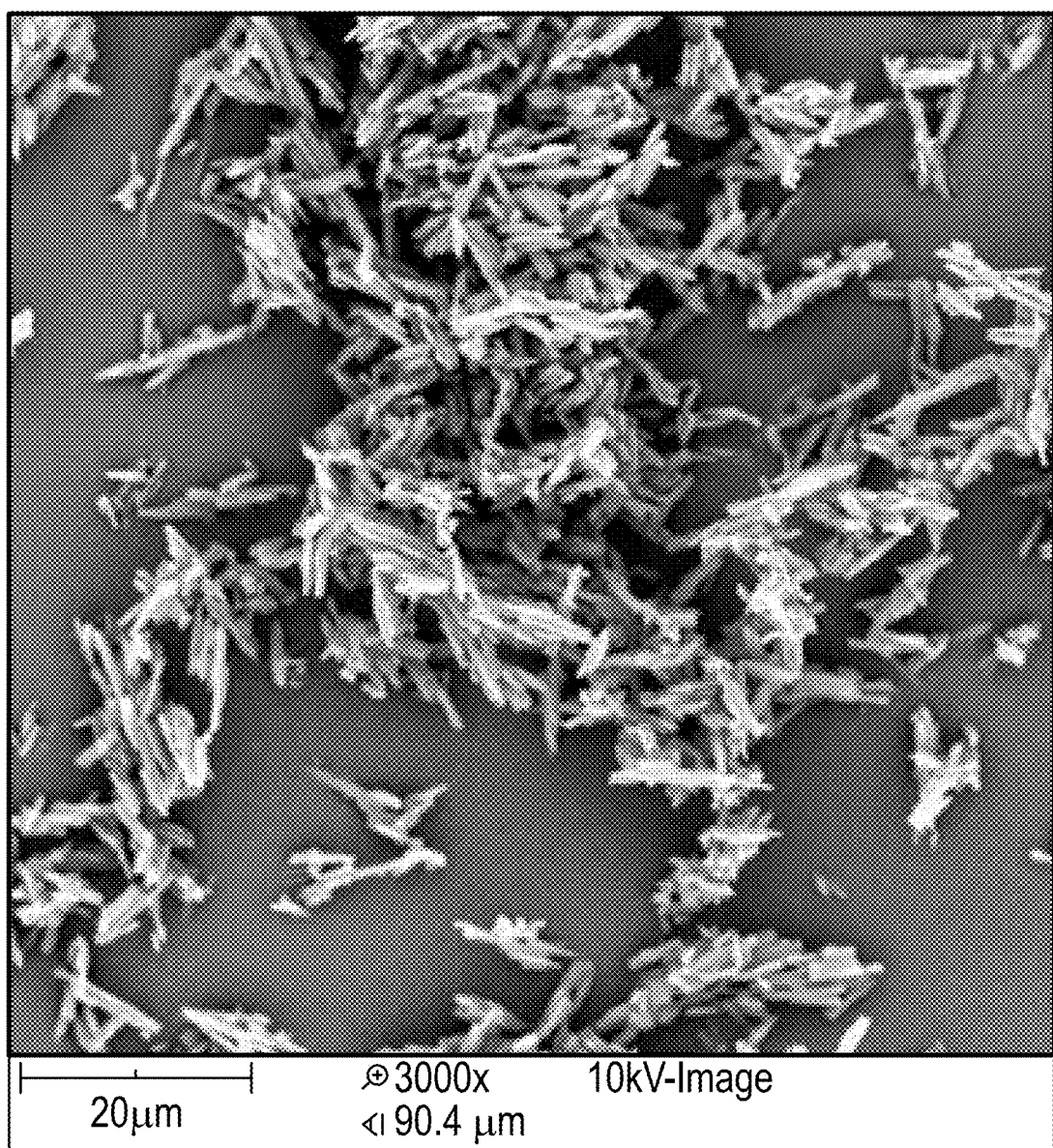
FIG. 29 shows a scanning electron microscopy (SEM) image of particles of Form T1 of Belumosudil Tosylate.

The present disclosure includes a crystalline polymorph of Belumosudil Tosylate, designated form T1. The crystalline Form T1 of Belumosudil Tosylate may be characterized by data selected from one or more of the following: an X-ray powder diffraction pattern substantially as depicted in FIG. 14; an X-ray powder diffraction pattern having peaks at 6.2, 12.3, 14.1, 17.7 and 18.4 degrees 2-theta±0.2 degrees 2-theta; a solid state $^{13}C$ NMR spectrum with characteristic peaks at 152.6, 143.4, 132.3, 125.3 and 119.8 ppm±0.2 ppm; a solid state $^{13}C$ NMR spectrum having the following chemical shift absolute differences from reference peak at 168.6 ppm±1 ppm: 16.0, 25.2, 36.3, 43.3 and 48.8 ppm±0.1 ppm; a solid state $^{13}C$ NMR spectrum substantially as depicted in any of FIGS. 26, 27 and 28; and combinations of these data.

Crystalline Form T1 of Belumosudil Tosylate may be further characterized by an X-ray powder diffraction pattern having peaks at 6.2, 12.3, 14.1, 17.7 and 18.4 degrees 2-theta±0.2 degrees 2-theta, and also having any one, two, three, four or five additional peaks selected from 9.9, 14.5, 16.7, 21.5 and 24.6 degrees 2-theta±0.2 degrees 2-theta.

Crystalline form T1 of Belumosudil Tosylate may be alternatively characterized by X-ray powder diffraction pattern having peaks at 6.2, 9.9, 12.3, 14.1, 14.5, 16.7, 17.7, 18.4, 21.5 and 24.6 degrees 2-theta±0.2 degrees 2-theta.

Crystalline form T1 of Belumosudil Tosylate may be an anhydrous form, as can be determined by TGA. In certain embodiment, the present disclosure comprises crystalline form T1 of Belumosudil Tosylate having 0.5% w/w or less, or 0.2% w/w or less, or 0.1 wt % or less, of total residual solvent. The residual solvent may be one or more polar solvents, preferably water and/or alcohols (particularly $C_{1-4}$ alcohols, especially ethanol, methanol, isopropanol, 1-propanol, or n-butanol), and most preferably the residual organic solvent may be methanol. Particularly, crystalline form T1 of Belumosudil Tosylate according to any aspect or embodiment of the disclosure may contain to 0.5% w/w or less, or 0.2% w/w or less, or 0.1 wt % or less, of methanol.

In one embodiment of the present disclosure, crystalline Form T1 of Belumosudil Tosylate is isolated. Particularly, crystalline form T1 of Belumosudil Tosylate according to any aspect or embodiment of the disclosure may be isolated.

In any aspect or embodiment of the present disclosure, crystalline Form T1 of Belumosudil Mesylate is non-hygroscopic. Particularly, Form T1 of Belumosudil Mesylate according to any aspect or embodiment is polymorphically stable at up to 100% relative humidity at room temperature for at least 7 days.

Crystalline Form T1 of Belumosudil Tosylate may be characterized by each of the above characteristics alone/or by all possible combinations, e.g., an XRPD pattern having peaks at 6.2, 12.3, 14.1, 17.7 and 18.4 degrees 2-theta±0.2 degrees 2-theta; an XRPD pattern as depicted in FIG. 14, and combinations thereof.

Crystalline form T1 of Belumosudil Tosylate may be prepared by crystallisation from a mixture comprising Belumosudil Tosylate and one or more polar solvents such as alcohols. Preferably, the solvent is methanol. In any embodiment, the process comprises:

(a) providing a mixture of Belumosudil Tosylate in one or more polar solvents, preferably comprising methanol;
(b) optionally stirring the mixture, optionally at elevated temperature;
(c) optionally cooling the mixture; and
(d) optionally isolating crystalline form T1 of Belumosudil Tosylate from the mixture.

In any of the embodiments of the process, the mixture in step (a) may be prepared by:

(i) providing a mixture of Belumosudil free base in a polar solvent; and
(ii) combining the mixture with Toluenesulfonic acid.

Preferably, the process for preparing Form T1 of Belumosudil Tosylate according to any embodiment described herein is carried out in the absence of water or substantially in the absence of water, particularly 2 wt % or less, 1 wt % or less, 0.5 wt % or less, 0.2 wt % or less, or 0.1 wt % or less of water.

In any aspect or embodiment of the process for preparing Form T1, the polar solvent is preferably an alcohol (particularly $C_{1-4}$ alcohols, especially ethanol, methanol, isopropanol, 1-propanol, or n-butanol), and most preferably the polar solvent is methanol. In step (i), the ratio of solvent to Belumosudil may be: about 10 to about 40 ml per gram of Belumosudil, about 14 to about 35 ml per gram of Belumosudil or about 16 to about 28 ml per gram of Belumosudil, or about 18 to about 24 ml per gram of Belumosudil, and optionally about 20 ml per gram of Belumosudil. The mixture may be a solution or a slurry In step (ii), combining of Toluenesulfonic acid to Belumosudil may be in any order. Preferably, Toluenesulfonic acid may be added to the mixture of Belumosudil in the solvent. The addition may be carried out portion-wise or dropwise. The Toluenesulfonic acid is optionally added in an amount of: about 0.7 to about 1.5 molar equivalents, about 0.9 to about 1.3 molar equivalents, about 1.0 to about 1.2 molar equivalents, or about 1.1 molar equivalents relative to Belumosudil. Preferably, step (ii) comprises adding Toluenesulfonic acid, to the mixture of Belumosudil and solvent.

Alternatively, in any of the embodiments of the process for preparing Form T1, the mixture in step (a) may be prepared by combining Belumosudil Tosylate with a polar solvent. Preferably the polar solvent is an alcohol (particularly $C_{1-4}$ alcohols, especially ethanol, methanol, isopropanol, 1-propanol, or n-butanol), and most preferably the polar solvent is methanol.

In any embodiment of the process for preparing Form T1, step (b) is carried out, preferably by stirring at a temperature of: about 30° C. to about 70° C., about 40° C. to about 60° C., about 45° C. to about 55° C., or about 50° C. The stirring may be carried out for any suitable time.

In any embodiment of the process for preparing form T1, step (c) is carried out, preferably wherein the cooling is to room temperature.

In any embodiment of the process for preparing form T1, step (d) may be carried out by any suitable method, for example by filtration, decantation or by centrifuge. Preferably the isolation of the solid is by filtration or by centrifuge, and more preferably by centrifuge.

In any embodiment of the process for preparing Form T1, the process may further comprise washing and/or drying steps.

Figure 15:
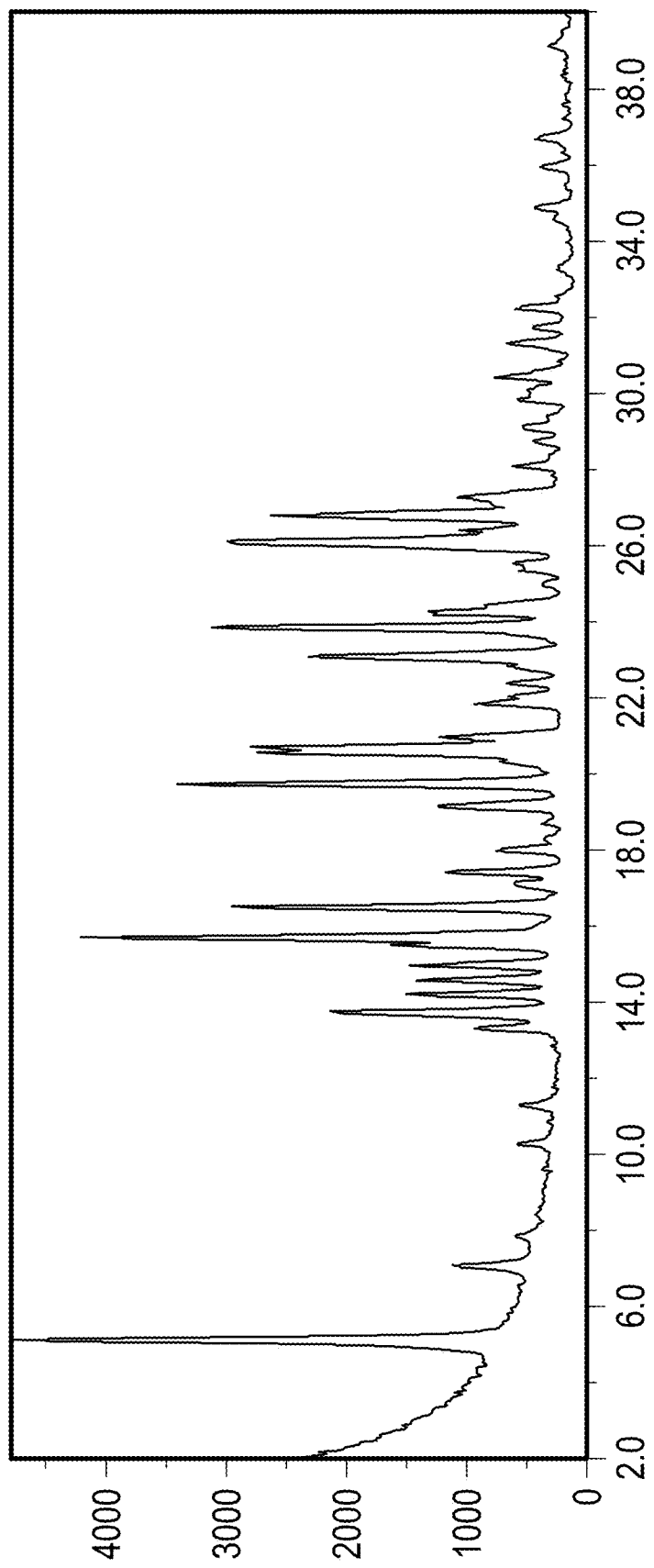
FIG. 15 shows a characteristic X-ray powder diffraction pattern (XRPD) of Belumosudil Tosylate form T2.
Figure 30:
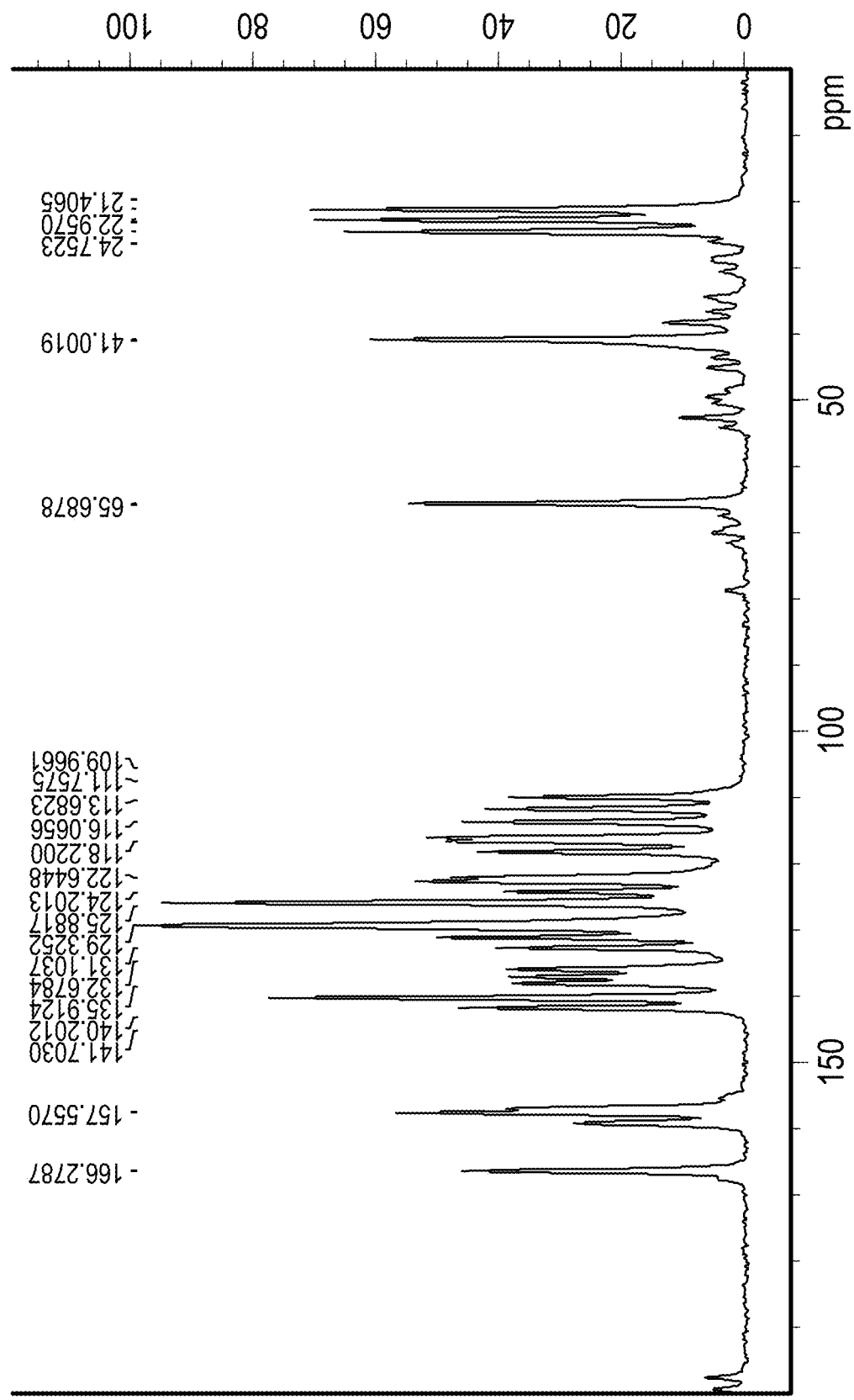
FIG. 30 shows a characteristic solid state $^{13}$C NMR spectrum of Form T2 of Belumosudil Tosylate (full range 200-0 ppm).
Figure 31:
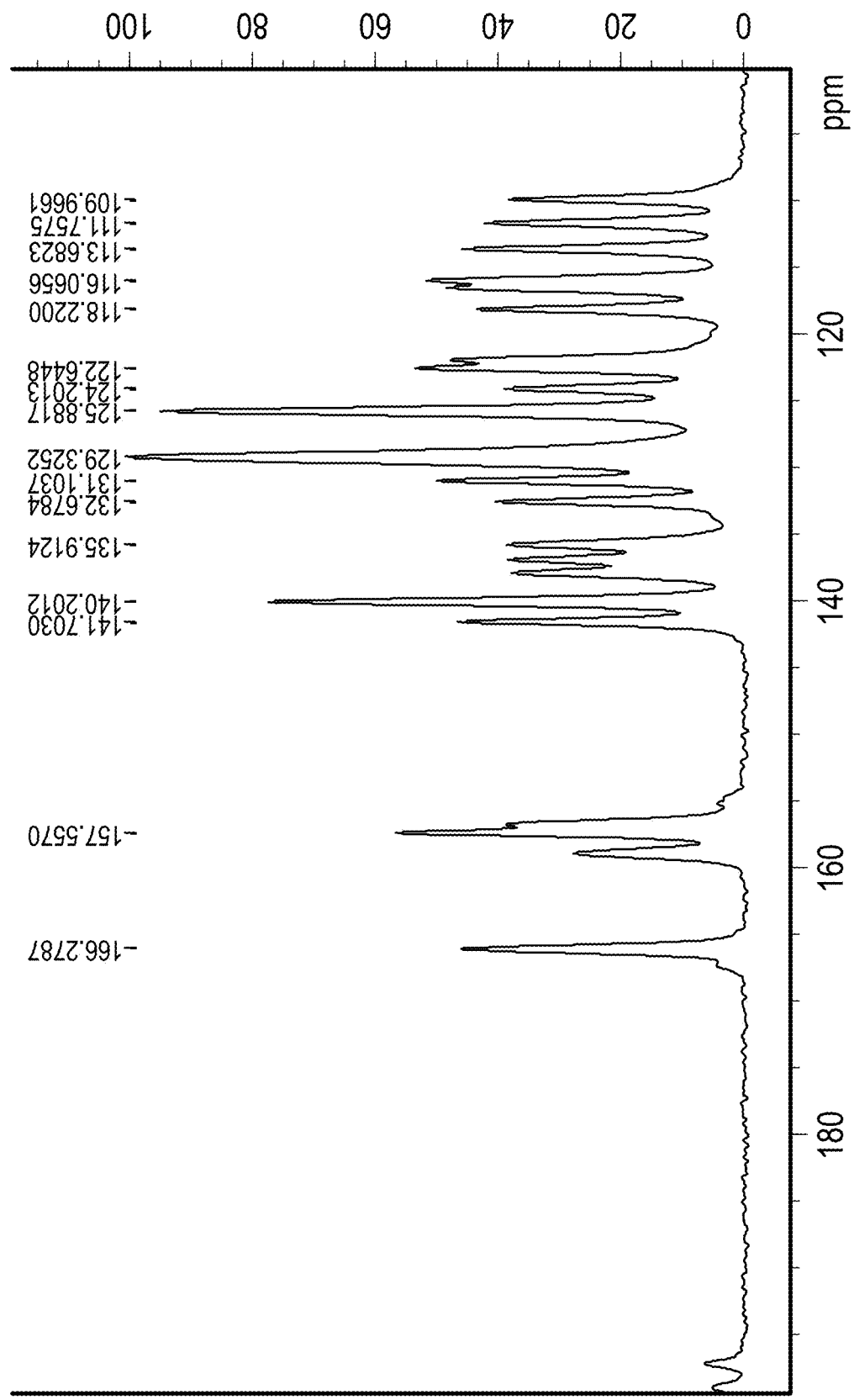
FIG. 31 shows a characteristic solid state $^{13}$C NMR spectrum of Form T2 of Belumosudil Tosylate 200-100 ppm).
Figure 32:
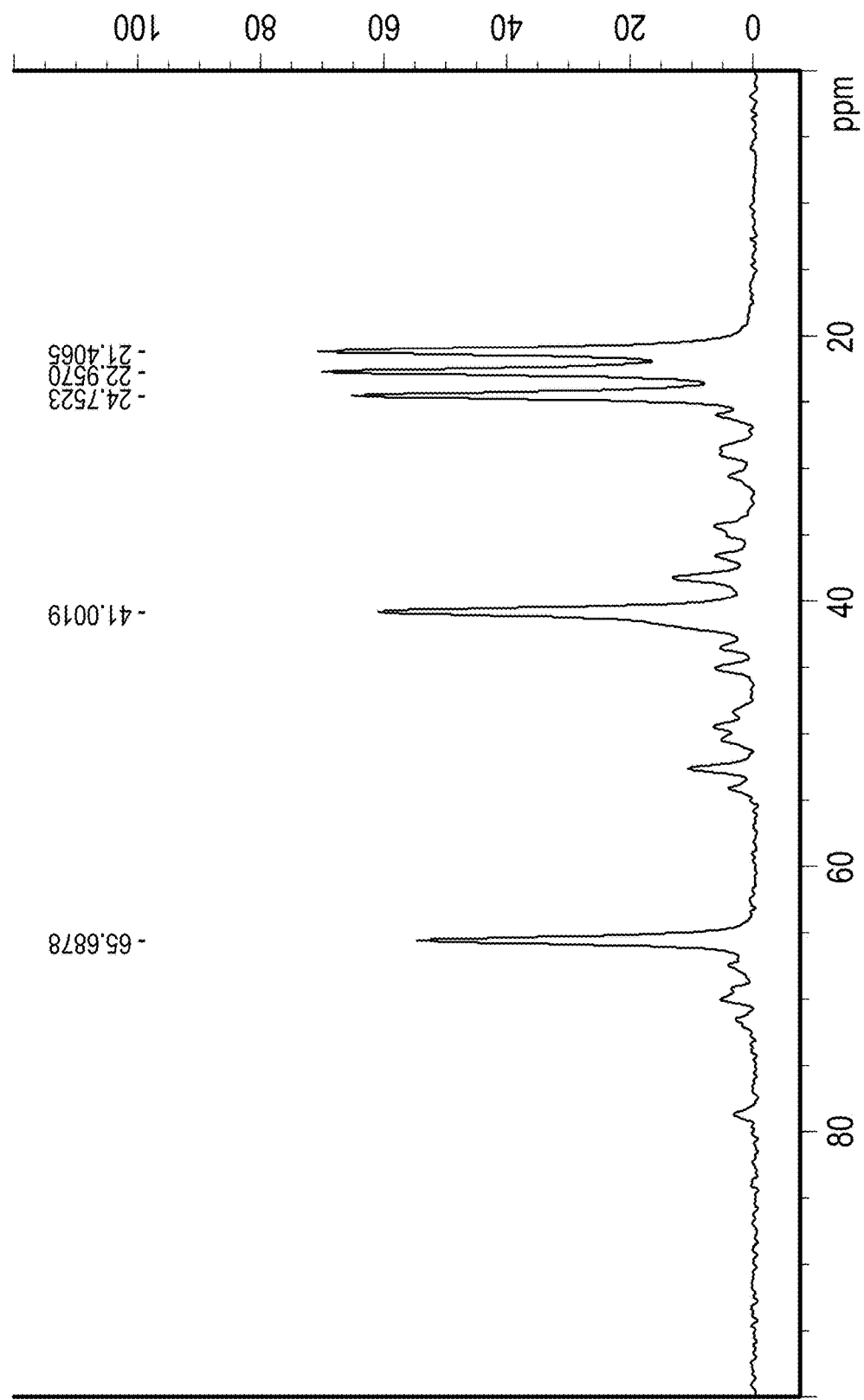
FIG. 32 shows a characteristic solid state $^{13}$C NMR spectrum of Form T2 of Belumosudil Tosylate (100-0 ppm).
Figure 33:
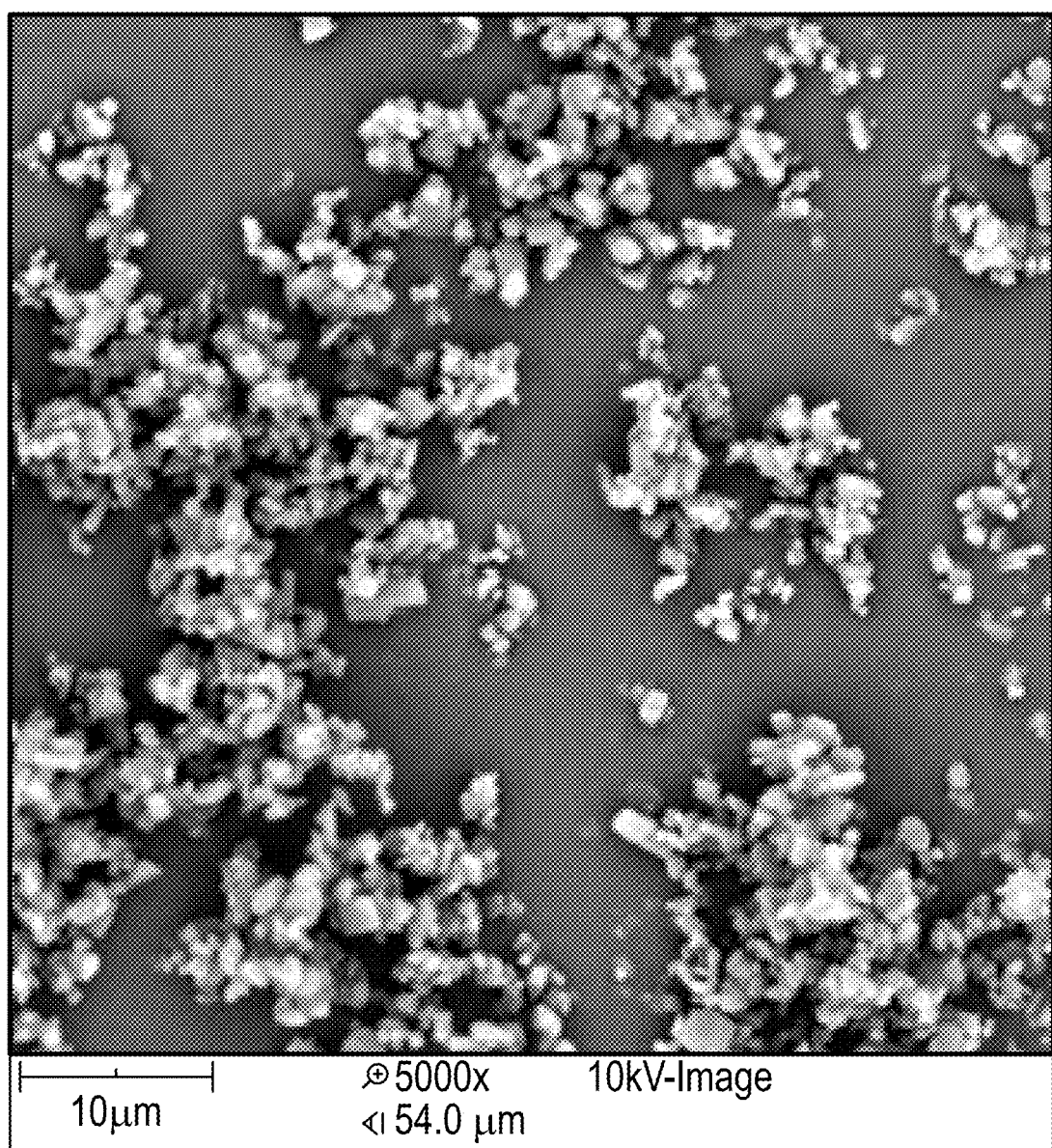
FIG. 33 shows a scanning electron microscopy (SEM) image of particles of Form T2 of Belumosudil Tosylate.

The present disclosure includes a crystalline polymorph of Belumosudil Tosylate, designated form T2. The crystalline Form T2 of Belumosudil Tosylate may be characterized by data selected from one or more of the following: an X-ray powder diffraction pattern substantially as depicted in FIG. 15; an X-ray powder diffraction pattern having peaks at 5.1, 15.7, 16.4, 19.7 and 23.7 degrees 2-theta±0.2 degrees 2-theta; a solid state $^{13}C$ NMR spectrum with characteristic peaks at 141.7, 140.2, 131.1, 125.9 and 124.2 ppm±0.2 ppm; a solid state $^{13}C$ NMR spectrum having the following chemical shift absolute differences from reference peak at 166.3 ppm±1 ppm: 24.6, 26.1, 35.2, 40.4 and 42.1 ppm±0.1 ppm; a solid state $^{13}C$ NMR spectrum substantially as depicted in any of FIGS. 30, 31 and 32; and combinations of these data.

Crystalline Form T2 of Belumosudil Tosylate may be further characterized by an X-ray powder diffraction pattern having peaks at 5.1, 15.7, 16.4, 19.7 and 23.7 degrees 2-theta±0.2 degrees 2-theta, and also having any one, two, three, four or five additional peaks selected from 13.7, 14.2, 14.6, 19.1 and 23.0 degrees 2-theta±0.2 degrees 2-theta.

Crystalline form T2 of Belumosudil Tosylate may be alternatively characterized by X-ray powder diffraction pattern having peaks at 5.1, 13.7, 14.2, 14.6, 15.7, 16.4, 19.1, 19.7, 23.0 and 23.7 degrees 2-theta±0.2 degrees 2-theta.

Crystalline form T2 of Belumosudil Tosylate may be an anhydrous form, as can be determined by TGA. In certain embodiment, the present disclosure comprises crystalline form T2 of Belumosudil Tosylate having 1% w/w or less, or 0.5% w/w or less or 0.2% w/w or less, or 0.1 wt % or less, of total residual solvent. The residual solvent may be one or more polar solvents, preferably water or alcohols (particularly $C_{1-4}$ alcohols, especially ethanol, methanol, isopropanol, 1-propanol, or n-butanol), and most preferably the residual organic solvent may be water and/or ethanol. Particularly, crystalline form T2 of Belumosudil Tosylate according to any aspect or embodiment of the disclosure may contain 0.5% w/w or less, or 0.2% w/w or less, or 0.1 wt % or less, of ethanol. In one embodiment of the present disclosure, crystalline Form T2 of Belumosudil Tosylate is isolated. Particularly, crystalline form T2 of Belumosudil Tosylate according to any aspect or embodiment of the disclosure may be isolated.

In any aspect or embodiment of the present disclosure, crystalline Form T2 of Belumosudil Mesylate is non-hygroscopic. Particularly, Form T2 of Belumosudil Mesylate according to any aspect or embodiment is polymorphically stable at up to 100% relative humidity at room temperature for at least 7 days.

Crystalline Form T2 of Belumosudil Tosylate may be characterized by each of the above characteristics alone/or by all possible combinations, e.g., an XRPD pattern having peaks at 5.1, 15.7, 16.4, 19.7 and 23.7 degrees 2-theta±0.2 degrees 2-theta; an XRPD pattern as depicted in FIG. 15, and combinations thereof.

Crystalline form T2 of Belumosudil Tosylate may be prepared by crystallisation from a mixture comprising Belumosudil Tosylate and one or more polar solvent such as water. In any embodiment, the process comprises:

(a) providing a mixture of Belumosudil Tosylate in one or more polar solvent;
(b) optionally stirring the mixture, optionally at elevated temperature;
(c) optionally cooling to room temperature; and
(d) optionally isolating crystalline form T2 of Belumosudil Mesylate from the mixture.

In any of the embodiments of the process for preparing Form T2, the mixture in step (a) may be prepared by:
(i) providing a mixture of Belumosudil free base (preferably Form B1 as described herein) in a polar solvent, preferably comprising water and/or ethanol; and
(ii) combining the mixture with Toluenesulfonic acid, optionally at elevated temperature; and
(iii) optionally adding a polar solvent.

In any aspect or embodiment of the process for preparing Form T2, the polar solvent in step (i) preferably comprises water, and more preferably the polar solvent in step (i) water. In step (i), the ratio of solvent to Belumosudil may be: about 10 to about 40 ml per gram of Belumosudil, about 14 to about 35 ml per gram of Belumosudil or about 16 to about 28 ml per gram of Belumosudil, or about 18 to about 24 ml per gram of Belumosudil, about 20 to about 30, and optionally about 20 ml per gram of Belumosudil. The mixture may be a solution or a slurry.

In any aspect or embodiment of the process for preparing Form T2, step (ii) comprises combining Toluenesulfonic acid to Belumosudil in any order. Preferably, Toluenesulfonic acid may be added to the mixture of Belumosudil in the solvent. The addition may be carried out portion-wise or dropwise. The Toluenesulfonic acid is optionally added in an amount of: about 0.7 to about 1.5 molar equivalents, about 0.9 to about 1.3 molar equivalents, about 1.0 to about 1.2 molar equivalents, or about 1.1 molar equivalents relative to Belumosudil. Preferably, step (ii) comprises adding Toluenesulfonic acid, to the mixture of Belumosudil and solvent.

In any aspect or embodiment of the process for preparing Form T2, in step (iii), the polar solvent is preferably selected from the group consisting of methanol, ethanol, isopropanol, 1-propanol, and n-butanol. More preferably, the polar solvent in step (iii) is ethanol. In step (iii), the ratio of total solvent to Belumosudil may be from: about 20 to about 50 ml, about 20 to about 40 ml, about 22 to about 35 ml, or about 25 ml, per gram of Belumosudil.

Alternatively, in any of the embodiments of the process for preparing Form T2, the mixture in step (a) may be prepared by combining Belumosudil Tosylate with one or more polar solvents. Preferably the polar solvent is water and/or an alcohol (particularly $C_{1-4}$ alcohols, especially ethanol, methanol, isopropanol, 1-propanol, or n-butanol). Preferably, the polar solvent is water and ethanol.

In any embodiment of the process for preparing Form T2, step (b) is carried out, preferably by stirring at a temperature of: about 30° C. to about 70° C., about 40° C. to about 60° C., about 45° C. to about 55° C., or about 50° C. The stirring may be carried out for any suitable time. Typically, the stirring may be carried out over a period of about 10 minutes to about 2 hours, about 20 minutes to about 1 hour, or about 50 minutes.

In any embodiment of the process for preparing Form T2, the mixture may be cooled, preferably to room temperature, and step (d) may be carried out by any suitable method, for example by filtration, decantation or by centrifuge. Preferably the isolation of the solid is by filtration or by centrifuge, and more preferably by centrifuge.

In any embodiment the process may further comprise washing and/or drying steps.

The above crystalline polymorphs of Belumosudil or salts thereof, including Belumosudil Mesylate, Belumosudil Tosylate and/or Belumosudil Besylate can be used to prepare other crystalline polymorphs of Belumosudil, Belumosudil salts and their solid state forms.

The present disclosure encompasses a process for preparing other solid state forms of Belumosudil, Belumosudil salts and their solid state forms thereof. The process includes preparing any one of the solid state forms of Belumosudil or salts thereof by the processes of the present disclosure, and converting that salt to said other Belumosudil salt. The conversion can be done, for example, by a process including basifying any one or a combination of the above described salts such as Belumosudil Mesylate Belumosudil Tosylate and/or Belumosudil Besylate and/or solid state forms thereof, and reacting the obtained Belumosudil base with an appropriate acid, to obtain the corresponding salt. Alternatively, the conversion can be done by salt switching, i.e., reacting a Belumosudil acid addition salt, with an acid having a pKa which is lower than the pKa of the acid of the first Belumosudil acid addition salt.

The present disclosure provides the above described crystalline polymorphs of Belumosudil or salts thereof, including Belumosudil Mesylate, Belumosudil Tosylate and/or Belumosudil Besylate for use in the preparation of pharmaceutical compositions comprising Belumosudil, salts thereof and/or crystalline polymorphs thereof.

The present disclosure also encompasses the use of crystalline polymorphs of Belumosudil or salts thereof, such as crystalline forms of Belumosudil Mesylate, Belumosudil Tosylate and/or Belumosudil Besylate of the present disclosure for the preparation of pharmaceutical compositions of crystalline polymorph Belumosudil or salts thereof, such as including Belumosudil Mesylate, Belumosudil Tosylate and/or Belumosudil Besylate and/or crystalline polymorphs thereof.

In any aspect or embodiment of the present disclosure, any of the solid state forms of Belumosudil, Belumosudil Mesylate, Belumosudil Tosylate and/or Belumosudil Besylate described herein may be polymorphically pure or may be substantially free of any other solid state forms of the subject compound (i.e., Belumosudil, Belumosudil Mesylate, Belumosudil Tosylate and/or Belumosudil Besylate, respectively). In any aspect or embodiment of the present disclosure, any of the solid state forms of Belumosudil, Belumosudil Mesylate, Belumosudil Tosylate and/or Belumosudil besylate may contain: about 20% (w/w) or less, about 10% (w/w) or less, about 5% (w/w) or less, about 2% (w/w) or less, about 1% (w/w) or less, about 0.5% (w/w) or less, about 0.2% (w/w) or less, about 0.1% (w/w) or less, or about 0%, of any other solid state forms of the subject compound, preferably as measured by XRPD. Thus, any of the disclosed crystalline forms of Belumosudil, Belumosudil Mesylate, Belumosudil Tosylate and/or Belumosudil besylate described herein may be substantially free of any other solid state forms of the subject compound, and may contain greater than about 80% (w/w), greater than about 90% (w/w), greater than about 95% (w/w), greater than about 98% (w/w), greater than about 99% (w/w), or about 100% of the solid state form of the Belumosudil, Belumosudil Mesylate, Belumosudil Tosylate and/or Belumosudil besylate.

The present disclosure includes processes for preparing the above mentioned pharmaceutical compositions. The processes include combining any one or a combination of the crystalline polymorphs of Belumosudil or salts thereof, of the present disclosure with at least one pharmaceutically acceptable excipient.

Pharmaceutical combinations or formulations of the present disclosure contain any one or a combination of the solid state forms of Belumosudil or salts thereof, of the present disclosure. In addition to the active ingredient, the pharmaceutical formulations of the present disclosure can contain one or more excipients. Excipients are added to the formulation for a variety of purposes. Preferably, the pharmaceutical composition or formulation according to any aspect or embodiment of the present disclosure is in the form of a tablet or a capsule, more preferably a tablet.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g., Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g., Ac-Di-Sol®, Primellose®), colloidal silicon dioxide, croscarmellose sodium, crospovidone (e.g., Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g., Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Belumosudil and any other solid excipients can be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, xanthan gum and combinations thereof.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and/or sorbitol, an opacifying agent and/or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of Belumosudil can be administered. Belumosudil may be formulated for administration to a mammal, in embodiments to a human, by injection. Belumosudil can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of Belumosudil and the pharmaceutical compositions and/or formulations of Belumosudil of the present disclosure can be used as medicaments, in embodiments in the treatment of Graft-Versus-Host Disease including Chronic Graft-Versus-Host Disease, Systemic Sclerosis including Diffuse Cutaneous Systemic Sclerosis, Fibrosis including Idiopathic Pulmonary Fibrosis, Plaque Psoriasis, Systemic Scleroderma, and particularly Chronic Graft-Versus-Host Disease and/or Systemic Sclerosis.

The present disclosure also provides methods of treating Graft-Versus-Host Disease including Chronic Graft-Versus-Host Disease, Systemic Sclerosis including Diffuse Cutaneous Systemic Sclerosis, Fibrosis including Idiopathic Pulmonary Fibrosis, Plaque Psoriasis, Systemic Scleroderma, and particularly Chronic Graft-Versus-Host Disease and/or Systemic Sclerosis by administering a therapeutically effective amount of any one or a combination of the crystalline polymorphs of Belumosudil of the present disclosure, or at least one of the above pharmaceutical compositions and/or formulations, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-Ray Diffraction ("XRPD") Method

For Examples 1-9 and 12-15: XRPD analysis was performed on ARL (SCINTAG) powder X-Ray diffractometer model X'TRA equipped with a solid state detector. Copper radiation of 1.5418 Å was used. Scanning parameters: range: 2-40 degrees two-theta; scan mode: continuous scan; step size: 0.05°, and a rate of 3 deg/min.

For examples 10 and 11: XRPD analysis was performed on a Bruker powder X-Ray diffractometer model D8 ADVANCE equipped with a solid state detector. Copper radiation of 1.54060 Å was used. Scanning parameters: range: 2-40 degrees two-theta; scan mode; step size: 0.05°.

The positions of the peaks were corrected respective to the silicon theoretical peak at 28.45 degrees two theta.

Solid State $^{13}$C-NMR Method

Solid-state 13C NMR spectra were recorded with variable amplitude cross polarization, magic angle spinning and high power proton decoupling using a BRUKER Avance II+ spectrometer operating at 125 MHz and controlled temperature at 0° C. A probe using 4 mm o.d. zirconia rotors was employed. The operation conditions were: contact time: 2 ms; recycle delay: 5 s; 1024 scans and spin rate of 11 kHz. Chemical shifts were referenced via a replacement sample of glycine (carboxyl carbon chemical shift assigned as 176.03 ppm relative to the signal of tetramethylsilane).

TGA Method

Thermogravimetric analysis was carried out Mettler Toledo TGA/DSC with the following scanning parameters:
Heating between 25-250° C.
Heating rate: 10° C./min.
Purging with 40 ml/min $N_2$ flow.
Sample weight: 7-15 mg.
Crucible: 150 μL alumina Crucible with standard aluminum lid.

SEM Method

SEM micrographs were taken on Phenom Pro, scanning microscope at 10 kV, low current. Samples were sputtered with gold by Denton Desk V sputter coater.

EXAMPLES

Preparation of Starting Materials

Belumosudil can be prepared according to methods known from the literature, for example according to International Publication No. WO 2006/105081.

Example 1: Preparation of Amorphous Belumosudil

Procedure A

Methanol (90 ml, 90V) was added to Belumosudil (1 gram, 2.21 mmol) to give a slurry. The slurry was magnetically stirred at 62° C. for 15 minutes to obtain clear solution followed by mechanical filtration. The solution was cooled to room temperature and then was dried in spray drier at Tin=140° C. (Tout=78° C.). The obtained solid was analyzed by X-ray powder diffraction and the XRPD pattern is presented in FIG. 1.

Procedure B

Methanol (3.5 ml, 70V) was added to Belumosudil (50 mg, 0.11 mmol) to give slurry. The slurry was magnetically stirred at 60° C. for 15 minutes to obtain clear solution followed by mechanical filtration. The obtained clear mother-liquor was evaporated upon 50° C./300-35 mbar to give a solid. The obtained solid was characterized by X-ray powder diffraction as Amorphous Belumosudil.

Example 2: Preparation of Crystalline Form B1 of Belumosudil

Procedure A

Acetone (7.5 ml, 250V) was added to Belumosudil (30 mg, 0.066 mmol) to obtain a clear solution. The solution was then mechanically filtered at room temperature and allowed to slowly evaporate at this temperature over a period of 6 days. The obtained solid was analyzed by X-ray powder diffraction and Belumosudil crystal form B1 was obtained. The XRPD pattern is presented in FIG. 2.

Procedure B

Ethanol (0.6 ml, 20V) was added to Amorphous Belumosudil (30 mg, 0.066 mmol) to give slurry. The slurry was magnetically stirred at 50° C. over a period of 5 hours. The solid was separated by centrifuge and dried in a vacuum oven at 45° C. over a period of 20 hours to afford an off white solid, which was identified as Belumosudil crystalline form B1.

Example 3: Preparation of Crystalline Form B2 of Belumosudil

Procedure A

Acetonitrile (12 ml, 400V) was added to Amorphous Belumosudil (30 mg, 0.066 mmol) at 80° C. to obtain clear solution. The solution was then mechanically filtered at room temperature and allowed to slowly evaporate at this temperature over a period of 5 days. The obtained solid was analyzed by XRPD and characterized as Belumosudil crystalline form B2. The XRPD pattern is presented in FIG. 3.

Procedure B

Amorphous Belumosudil (30 mg, 0.066 mmol) was heated by TGA to 160° C. over a period of 0.5 hours. The obtained solid was analyzed by X-ray powder diffraction and identified as Belumosudil crystalline form B2.

Procedure C

Methanol (12 ml, 400V) was added to Amorphous Belumosudil (30 mg, 0.066 mmol) to give a slurry at room temperature. The slurry was magnetically stirred at 50° C. over a period of 5 hours. The solid was separated by centrifuge and dried in a vacuum oven at 45° C. over a period of 20 hours. The obtained off white solid was analyzed by X-ray powder diffraction and characterized by X-ray powder diffraction as Belumosudil crystal form B2.

Example 4: Preparation of Crystalline Form B3 of Belumosudil

Tetrahydrofuran (5 ml, 50V) was added to Belumosudil (100 mg, 0.22 mmol) at 40° C. and stirred for 10 minutes to obtain clear solution. The solution was then mechanically filtered, cooled to room temperature and stirred over a period of 14 hours to afford a wet solid. The solid was separated by centrifuge. The obtained wet solid was analyzed by XRPD and characterized as Belumosudil crystalline form B3. The XRPD pattern is presented in FIG. 4.

Example 5: Preparation of Crystalline Form M1 of Belumosudil Mesylate

Procedure A

Ethanol (4 ml, 20V) was added to Belumosudil (200 mg, 0.44 mmol) to obtain a slurry at room temperature. Next, Methanesulfonic acid (31 µL, 1.1 eq) was added drop-wise to give clear solution. The solution was heated to 50° C. and precipitation was observed. Ethanol (3 ml, 15V) was added to the obtained massive precipitate followed by magnetically stirring over a period of 30 minutes at 50° C. Next, the precipitate was spontaneously cooled to room temperature. The solid was separated by centrifuge. The obtained solid was washed twice with ethanol (400 µL, 2V) and dried in a vacuum oven at 45° C. over a period of 16 hours to afford yellow solid. The obtained solid was analyzed by X-ray powder diffraction and characterized as Belumosudil Mesylate crystal form M1. The XRPD pattern is presented in FIG. 5.

Procedure B

DMSO (0.9 ml, 30V) was added to Belumosudil Mesylate salt (30 mg, 0.06 mmol) to give slurry. The slurry was heated to 50° C. for 10 minutes to obtain complete dissolution, followed by a hot mechanical filtration. Next, ethanol as anti-solvent (2.7 ml, 100V) was added drop-wise to obtain a solid precipitate. Next, the slurry was magnetically stirred at room temperature during 40 hours. Then, the solid was isolated by centrifuge. The obtained wet solid was analyzed by X-ray powder diffraction and identified as Belumosudil Mesylate crystal form M1.

Procedure C

Isopropyl alcohol (2 ml, 20V) was added to Belumosudil (100 mg, 0.2 mmol) to obtain a slurry at room temperature. Next, Methanesulfonic acid (161 µL, 1.1 eq) was added drop-wise to give clear solution. The solution was heated to 50° C. and precipitation was observed and magnetically stirring over a period of 30 minutes at 50° C. Next, the precipitate was spontaneously cooled to room temperature. The solid was separated by centrifuge. The obtained solid was washed twice with IPA (200 µL, 2V) to afford yellow solid. The obtained solid was analyzed by X-ray powder diffraction and identified as Belumosudil Mesylate crystal form M1.

Procedure D

N-butanol (2 ml, 20V) was added to Belumosudil (100 mg, 0.2 mmol) to obtain a slurry at room temperature. Next, Methanesulfonic acid (161 µL, 1.1 eq) was added drop-wise to give clear solution. The solution was heated to 50° C. and precipitation was observed and magnetically stirring over a period of 30 minutes at 50° C. Next, the precipitate was spontaneously cooled to room temperature. The solid was separated by centrifuge. The obtained solid was washed twice with N-butanol (200 µL, 2V) to afford yellow solid. The obtained solid was analyzed by X-ray powder diffraction and identified as Belumosudil Mesylate crystal form M1.

Procedure E 1-propanol (2 ml, 20V) was added to Belumosudil (100 mg, 0.2 mmol) to obtain a slurry at room temperature. Next, Methanesulfonic acid (161 µL, 1.1 eq) was added drop-wise to give clear solution. The solution was heated to 50° C. and precipitation was observed and magnetically stirring over a period of 30 minutes at 50° C. Next, the precipitate was spontaneously cooled to room temperature. The solid was separated by centrifuge. The obtained solid was washed twice with 1-propanol (200 µL, 2V to afford yellow solid.

The obtained solid was analyzed by X-ray powder diffraction and identified as Belumosudil Mesylate crystal form M1

Procedure F 2,2,2-Trifluoroethanol (0.3 ml, 10V) was added to Belumosudil Mesylate salt (30 mg, 0.06 mmol) to give slurry. The slurry was heated to 60° C. for 10 minutes to obtain complete dissolution, followed by a hot mechanical filtration. Next, ethanol as anti-solvent (1.2 ml, 40V) was added drop-wise to obtain a solid precipitate. Next, the slurry was magnetically stirred at room temperature during 17 hours. Then, the solid was isolated by centrifuge. The obtained wet solid was analyzed by X-ray powder diffraction and identified as Belumosudil Mesylate crystal form M1.

Example 6: Preparation of Crystalline Form B4 of Belumosudil

Procedure A

Methanol (0.6 ml, 20V) was added to Belumosudil form B1 (30 mg, 0.066 mmol) to obtain a slurry. The slurry was then magnetically stirred at 50° C. for 5 hours. Then, the slurry was cooled to room temperature and magnetically stirred for 16 hours. The solid was then isolated at room temperature by centrifuge. The obtained wet solid was dried in a vacuum oven at 45° C. over a period of 18 hours to afford an off white solid which was characterized by X-ray powder diffraction and the XRPD pattern is presented in FIG. 6.

Procedure B

Acetonitrile:MeOH (0.75 ml, 25V, 1:1 eq) was added to B1 (50 mg, 0.11 mmol) to give a slurry. The slurry was magnetically stirred at room temperature for a period of 1 week. The solid was then isolated at room temperature by centrifuge. The obtained wet solid was characterized by X-ray powder diffraction as Belumosudil crystal form B4.

Example 7: Preparation of Crystalline Form M2 of Belumosudil Mesylate

Procedure A

Water (2 ml, 20V) was added to Form B1 (100 mg, 0.22 mmol) to obtain a slurry at room temperature. Next, Methanesulfonic acid (16 µL, 1.1 eq) was added drop-wise to give a slurry. The slurry was heated to 50° C. over a period of 45 minutes to obtain a clear solution. Next, the solution was spontaneously cooled to room temperature and a precipitate was observed. The obtained solid was isolated using a centrifuge. The isolated solid was washed twice with water (0.2 ml, 2V) and dried in a vacuum oven at 45° C. over a period of 18 hours to afford a yellow solid. The obtained solid was analyzed by X-ray powder diffraction and the XRPD pattern is presented in FIG. 7.

Procedure B

A Water:Ethanol (2 ml, 20V, 1:3) mixture was added to Form B1 (100 mg, 0.22 mmol) to obtain a slurry at room temperature. Next, Methanesulfonic acid (16 µL, 1.1 eq) was added drop-wise to give a slurry. The slurry was heated to 50° C. over a period of 45 minutes to obtain a clear solution. Next, the solution was spontaneously cooled to room temperature and a precipitate was observed. The obtained solid was isolated using a centrifuge. The isolated solid was washed twice with water:ethanol (2.2 ml, 22V, 1:3) and dried in a vacuum oven at 45° C. over a period of 18 hours to afford yellow solid. The obtained solid was analyzed by X-ray powder diffraction and identified as Belumosudil Mesylate crystal form M2.

Procedure C

Water (2 ml, 40V) was added to Belumosudil Mesylate salt form M1 (50 mg, 0.11 mmol) to give a slurry. The slurry was magnetically stirred at 60° C. over a period of 1 week. Then, the solid was isolated at room temperature by centrifuge. The obtained wet solid was analyzed by X-ray powder diffraction and identified as Belumosudil Mesylate crystal form M2.

Procedure D

DMSO (2 ml, 40V) was added to Belumosudil Mesylate salt form M1 (50 mg, 0.11 mmol) to give a slurry. The slurry was heated to 50° C. for 10 minutes to obtain complete dissolution, followed by a hot mechanical filtration. The solution was spontaneously cooled to room temperature and magnetically stirred for 5 days. Next, cold water as anti-solvent (5 ml, 100V, 4° C.) was added drop-wise to obtain a solid precipitate. Next, the slurry was magnetically stirred at room temperature during 18 hours. Then, the solid was isolated by centrifuge. The obtained wet solid was analyzed by X-ray powder diffraction and identified as Belumosudil Mesylate crystal form M2.

Procedure E 2,2,2-Trifluoroethanol (0.3 ml, 10V) was added to Belumosudil Mesylate salt (30 mg, 0.06 mmol) to give slurry. The slurry was heated to 60° C. for 10 minutes to obtain complete dissolution, followed by a hot mechanical filtration. Next, water as anti-solvent (1.2 ml, 40V) was added drop-wise to obtain a solid precipitate. Next, the slurry was magnetically stirred at room temperature during 17 hours. Then, the solid was isolated by centrifuge. The obtained wet solid was analyzed by X-ray powder diffraction and identified as Belumosudil Mesylate crystal form M2.

Example 8: Preparation of Crystalline Form M3 of Belumosudil Mesylate

Procedure A

Belumosudil Mesylate salt form M2 (prepared according to procedure C of example 7) was dried in a vacuum oven at 200° C. over a period of 4 hours to afford a yellow solid. The obtained solid was characterized by X-ray powder diffraction as Belumosudil Mesylate crystal form M3.

Example 9: Preparation of Crystalline Form B5 of Belumosudil

Procedure A 2,2,2-Trifluoroethanol (TFE) (0.6 ml, 50V) was added to Belumosudil (12.5 mg, 0.03 mmol) to obtain clear solution. The solution was then magnetically stirred at 70° C. for 1 hour. Then, the solution was cooled to 4° C. at a rate of 20° C. every 10 minutes and a massive precipitate was observed. Additional TFE (0.1 ml, 10V) was added to give a slurry. Next, the solid was isolated using a centrifuge. Next, the mother liqueur was left for slow crystallization at 4° C. for 20 days. The obtained wet solid was filtered by Buchner and the solid was characterized by X-ray powder diffraction as Belumosudil crystal form B5 and the XRPD pattern is presented in FIG. 9.

Example 10: Preparation of Amorphous Belumosudil Mesylate

Procedure A

Figure 10:
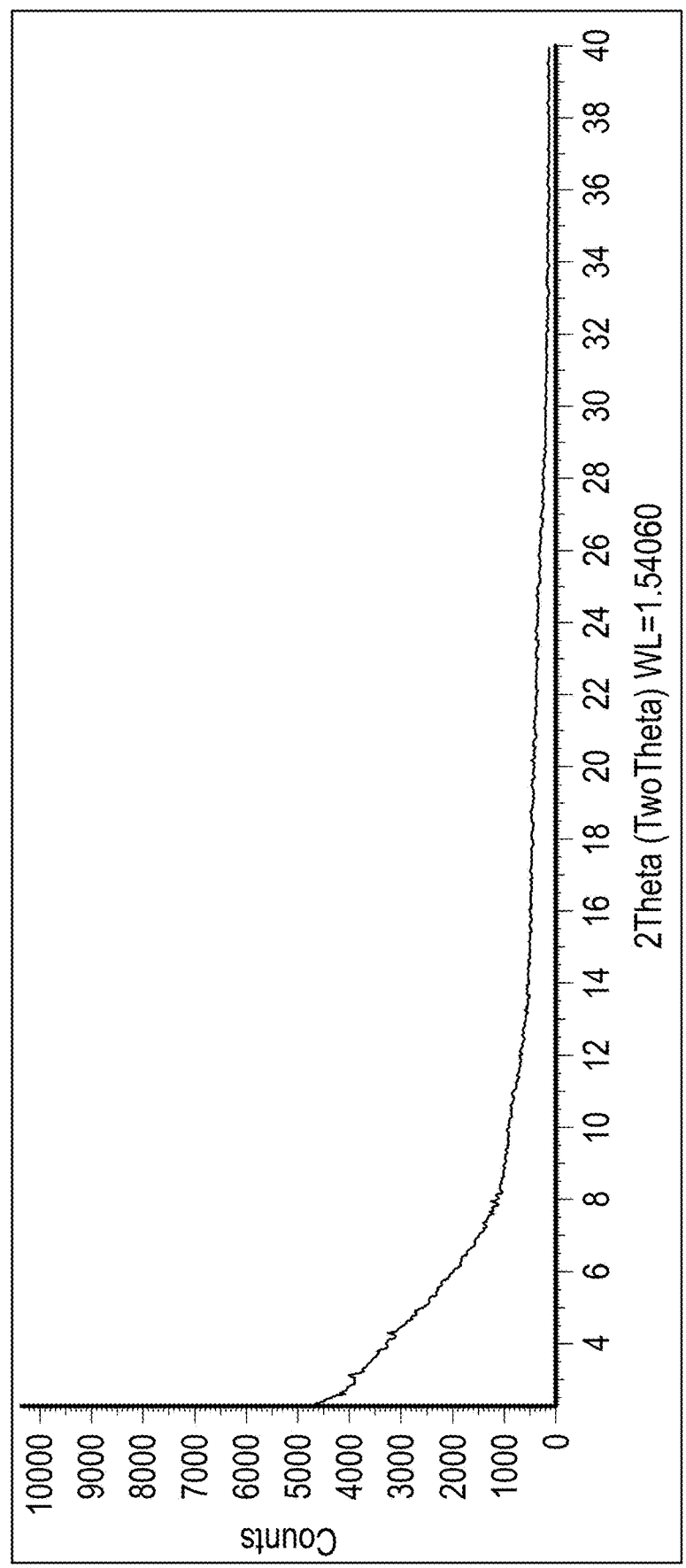
FIG. 10 shows a characteristic X-ray powder diffraction pattern (XRPD) of amorphous Belumosudil Mesylate.

Methanol (286 ml, 220 V) was added to Belumosudil Mesylate Form M1 (1.3 grams, 2.4 mmol) to give slurry. The slurry was magnetically stirred at 62° C. for 45 minutes to obtain a clear solution followed by mechanical filtration. The solution was cooled to room temperature and then was dried in spray drier at Tin=140° C. (Tout=63° C.). The obtained solid was analyzed by X-ray powder diffraction and identified as Amorphous Belumosudil Mesylate and the XRPD pattern is presented in FIG. 10.

Example 11: Preparation of Form M4 of Belumosudil Mesylate

Procedure A 2, 2, 2-Trifluoroethanol (TFE) (0.7 ml, 7V) was added to Belumosudil Mesylate form M1 (100 mg, 0.2 mmol) to obtain a clear solution. The clear solution was mechanically filtered and was added to Heptane (0.8 ml, 8V) that was precooled to 4° C. to obtain two phases. The solution was stirred at 4° C. for 4 days. Then, the mixture was seeded with Belumosudil Mesylate M3 (about 1 wt %) and after stirring for 1 day a solid precipitate was obtained. Next, the precipitate was isolated by centrifuge and dried in a vacuum oven at 45° C. over a period of 18 hours to afford yellow solid. The obtained solid was analyzed by X-ray powder diffraction and the XRPD pattern is presented in FIG. 11.

Procedure B

TFE (0.7 ml, 7V) was added to Belumosudil Mesylate form M1 (100 mg, 0.2 mmol) to obtain a clear solution. The clear solution was mechanically filtered and was added to Heptane (0.8 ml, 8V) that was precooled to 4° C. to obtain two phases. Then, the mixture was seeded with Belumosudil Mesylate form M4 (about 1 wt %) and after stirring for 1 day solid precipitate was obtained. Next, the precipitate was isolated by centrifuge and dried in a vacuum oven at 45° C. over a period of 18 hours to afford a yellow solid. The obtained solid was analyzed by X-ray powder diffraction and identified as Belumosudil Mesylate crystal form M4.

Procedure C

TFE (0.7 ml, 7V) was added to Belumosudil Mesylate form M1 (100 mg, 0.2 mmol) to obtain a clear solution. The clear solution was mechanically filtered and was added to cyclopentylmethyl ether (0.8 ml, 8V) that was precooled to 4° C. Then, the mixture was seeded with Belumosudil Mesylate form M4 (about 1 wt %) and after stirring for 18 hours a solid precipitate was obtained. Next, the precipitate was isolated by centrifuge and dried in a vacuum oven at 45° C. over a period of 18 hours to afford yellow solid. The obtained solid was analyzed by X-ray powder diffraction and identified as Belumosudil Mesylate crystal form M4.

Procedure D

TFE (0.7 ml, 7V) was added to Belumosudil Mesylate form M1 (100 mg, 0.2 mmol) to obtain a clear solution. The clear solution was added to cyclopentylmethyl ether (0.8 ml, 8V) that was precooled to 4° C. and massive slurry was obtained. Next, cyclopentylmethyl ether (0.4 ml, 4V) was added to obtain slurry. Then, the mixture was seeded with NaCl (about 1 wt %) and after stirring for 1 hour precipitate was obtained. Next, the precipitate was isolated by centrifuge and dried in a vacuum oven at 45° C. over a period of 18 hours to afford yellow solid. The obtained solid was analyzed by X-ray powder diffraction and identified as Belumosudil Mesylate crystal form M4.

Example 12: Preparation of Form M5 of Belumosudil Mesylate

Procedure A

DMSO (9 ml, 30V) was added to Belumosudil Mesylate form M1 (300 mg, 0.6 mmol) to obtain a clear solution. Next, the clear solution was added to cyclopentylmethyl ether (9 ml, 30V) containing seeds of Belumosudil Mesylate form M4 (about 1 wt %) that was precooled to about 4° C., then additional cyclopentylmethyl ether (18 ml, 60V) and seeds of Belumosudil Mesylate form M4 (about 1 wt %) were added and after 10 minutes some precipitant was observed. The mixture was stirred for a period of 18 hours at about 4° C. and massive precipitate was obtained. Next, the precipitate was isolated by centrifuge and dried in a vacuum oven at 45° C. over a period of 18 hours to afford yellow solid. The obtained solid was analyzed by X-ray powder diffraction and the XRPD pattern is presented in FIG. 12.

Example 13: Preparation of Form BS1 of Belumosudil Besylate

Procedure A

Ethanol (10 ml, 20V) was added to Belumosudil form B1 (500 mg, 1.1 mmol) to obtain a slurry at room temperature. Next, Benzenesulfonic acid (192.3 mg, 1.1 eq) was added and the slurry was heated to 50° C. over a period of 45 minutes with stirring. Next, the slurry was spontaneously cooled to room temperature and the obtained solid was isolated using centrifuge. The isolated solid was dried in a vacuum oven at 45° C. over a period of 18 hours to afford yellow solid. The obtained solid was analyzed by X-ray powder diffraction and the XRPD pattern is presented in FIG. 13.

Example 14: Preparation of Form T1 of Belumosudil Tosylate

Procedure A

Methanol (2 ml, 20V) was added to Belumosudil form B1 (100 mg, 0.22 mmol) and heated to 50° C. to obtain a slurry. Next, p-toluenesulfonic acid (46.2 mg, 1.1 eq) was added and a clear solution was obtained. After stirring for 10 minutes at 50° C. precipitation was observed. The solution was stirred at 50° C. over a period of 45 minutes. Next, the solution was spontaneously cooled to room temperature and massive precipitation was observed. The obtained solid was isolated using centrifuge and washed once with Methanol (200 µL, 2V). The solid was dried in a vacuum oven at 45° C. over a period of 18 hours to afford yellow solid. The obtained solid was analyzed by X-ray powder diffraction and the XRPD pattern is presented in FIG. 14.

Example 15: Preparation of Form T2 of Belumosudil Tosylate

Procedure A

Water (1 ml, 20V) was added to Belumosudil form B1 (50 mg, 0.11 mmol) and heated to 50° C. to obtain slurry. Next, p-toluenesulfonic acid (23.1 mg, 1.1 eq) was added and the sticky slurry was stirred at 50° C. over a period of 20 minutes. Then, ethanol (250 µl, 5V) was added to obtain a slurry. The slurry was stirred at 50° C. over a period of 50 minutes. Next, the slurry was spontaneously cooled to room temperature and the obtained solid was isolated using centrifuge. The isolated solid was washed once with Water: Ethanol (1 ml, 2V, 4:1) and dried in a vacuum oven at 45° C. over a period of 18 hours to afford yellow solid. The obtained solid was analyzed by X-ray powder diffraction and the XRPD pattern is presented in FIG. 15.

Figure 16:
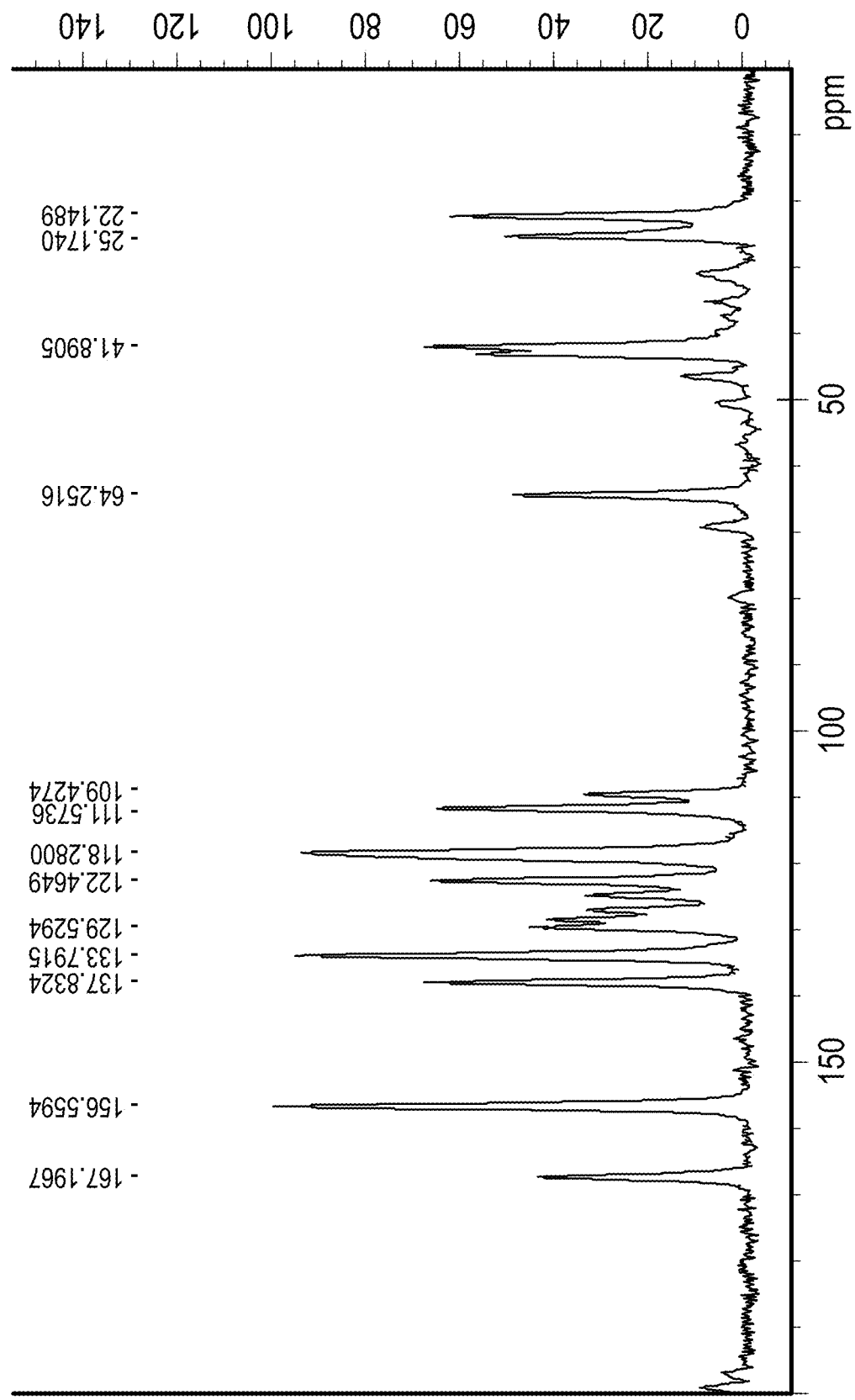
FIG. 16 shows a characteristic solid state $^{13}$C NMR spectrum of Form M1 of Belumosudil Mesylate (full range 200-0 ppm).
Figure 17:
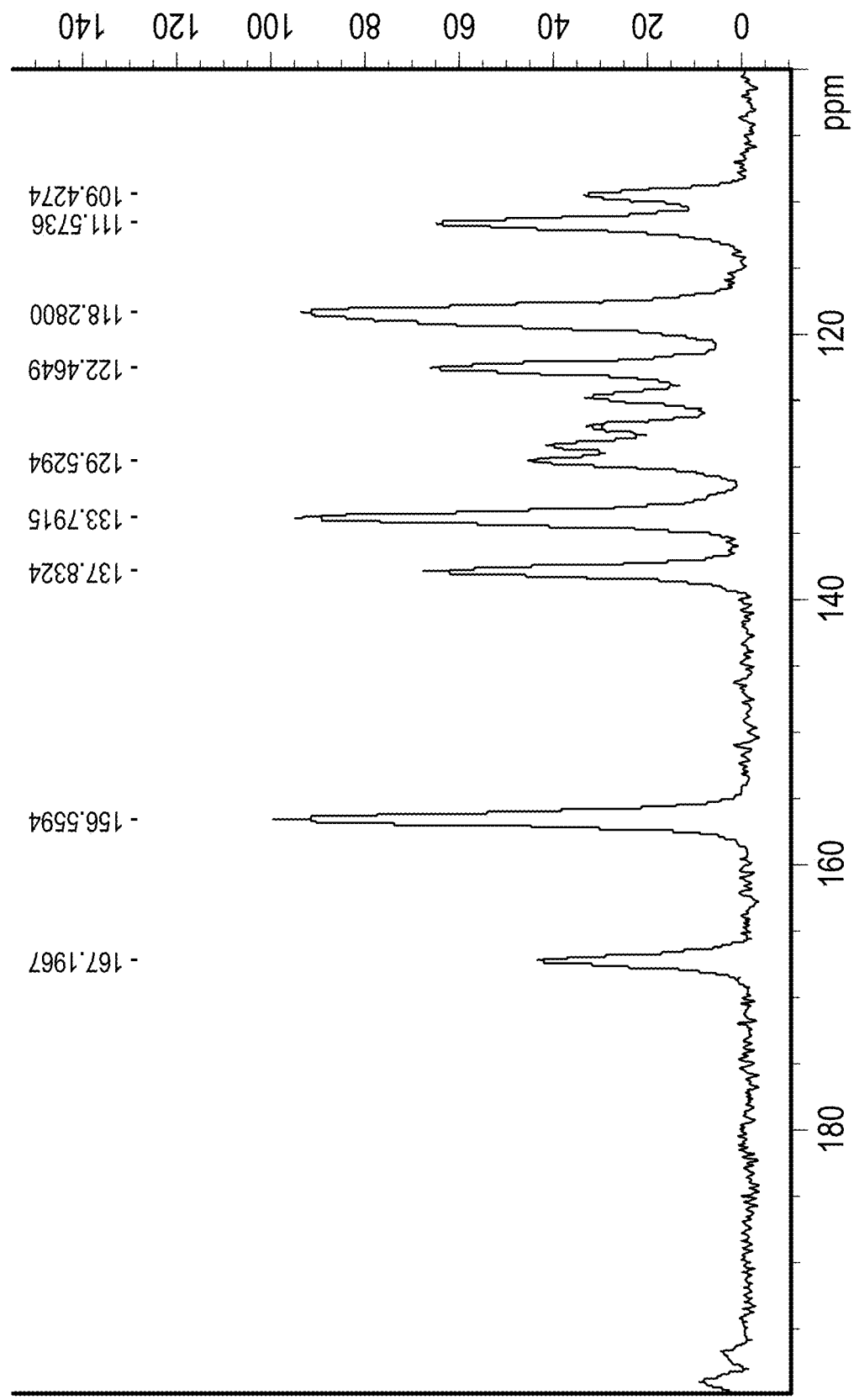
FIG. 17 shows a characteristic solid state $^{13}$C NMR spectrum of Form M1 of Belumosudil Mesylate 200-100 ppm).
Figure 18:
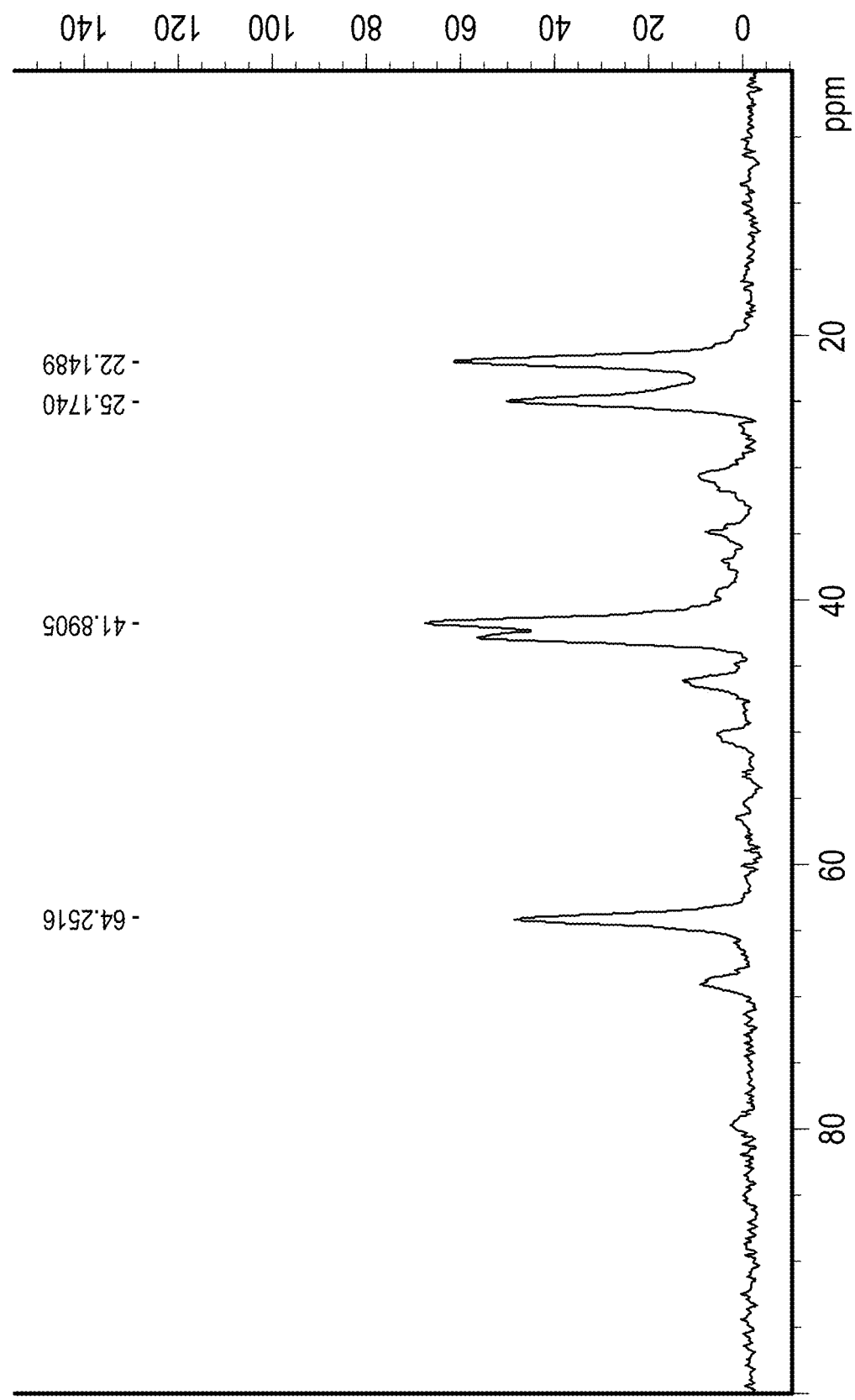
FIG. 18 shows a characteristic solid state $^{13}$C NMR spectrum of Form M1 of Belumosudil Mesylate (100-0 ppm).

The invention claimed is:

1. A crystalline form of Belumosudil Mesylate designated form M1, which is characterized by data selected from one or more of the following:
   (a) an XRPD pattern having peaks at 7.1, 17.2, 20.3, 21.5 and 25.5 degrees 2-theta±0.2 degrees 2-theta;
   (b) an XRPD pattern substantially as depicted in FIG. 5;
   (c) an XRPD pattern having peaks at 7.1, 17.2, 20.3, 21.5 and 25.5 degrees 2-theta±0.2 degrees 2-theta, and also having any one, two, three, four or five additional peaks selected from 8.4, 15.5, 16.8, 19.5 and 22.1 degrees two theta±0.2 degrees two theta;
   (d) an X-ray powder diffraction pattern having peaks at 7.1, 8.4, 15.5, 16.8, 17.2, 19.5, 20.3, 21.5, 22.1 and 25.5 degrees 2-theta±0.2 degrees 2-theta;
   (e) a solid state 13C NMR spectrum with characteristic peaks at 137.8, 133.8, 122.5, 118.3 and 111.6 ppm±0.2 ppm;
   (f) a solid state $^{13}$C NMR spectrum having the following chemical shift absolute differences from reference peak at 167.2 ppm±1 ppm: 29.4, 33.4, 44.7, 48.9 and 55.6 ppm±0.1 ppm; or
   (g) a solid state $^{13}$C NMR spectrum substantially as depicted in FIG. 16, 17 or 18.

2. The crystalline form according to claim 1, wherein the crystalline form is an anhydrous form.

3. The crystalline form according to claim 1, which contains no more than about 20% of any other crystalline forms of Belumosudil Mesylate.

4. The crystalline form according to claim 1, which contains no more than about 20% of amorphous Belumosudil Mesylate.

5. A pharmaceutical composition comprising the crystalline form according to claim 1 and at least one pharmaceutically acceptable excipient.

6. A process for preparing a pharmaceutical composition comprising combining the crystalline form according to claim 1 with at least one pharmaceutically acceptable excipient.

7. A method of treating Graft-Versus-Host Disease, Systemic Sclerosis, Fibrosis, Plaque Psoriasis, or Systemic Scleroderma, comprising administering a therapeutically effective amount of the crystalline form according to claim 1 to a subject in need of the treatment.

8. The method of claim 7, wherein the Graft-Versus-Host Disease is Chronic Graft-Versus-Host Disease.

9. The method of claim 7, wherein the Systemic Sclerosis is Diffuse Cutaneous Systemic Sclerosis.

10. The method of claim 7, wherein the Fibrosis is Idiopathic Pulmonary Fibrosis.

\* \* \* \* \*